United States Patent [19]

McAnalley

[11] Patent Number: 4,917,890

[45] Date of Patent: Apr. 17, 1990

[54] PROCESSES FOR PREPARATION OF ALOE PRODUCTS, PRODUCTS PRODUCED THEREBY AND COMPOSITIONS THEREOF

[75] Inventor: Bill H. McAnalley, Grand Prairie, Tex.

[73] Assignee: Carrington Laboratories, Inc., Irving, Tex.

[21] Appl. No.: 136,193

[22] Filed: Dec. 21, 1987

Related U.S. Application Data

[60] Division of Ser. No. 869,261, Jun. 5, 1986, Pat. No. 4,735,935, which is a continuation-in-part of Ser. No. 810,025, Dec. 17, 1985, abandoned, which is a continuation-in-part of Ser. No. 754,859, Jul. 12, 1985, abandoned, which is a continuation-in-part of Ser. No. 750,321, Jun. 28, 1985, abandoned, which is a continuation-in-part of Ser. No. 649,967, Sep. 12, 1984, abandoned, which is a continuation of Ser. No. 375,720, May 7, 1982, abandoned.

[51] Int. Cl.$^4$ ................. A61K 35/78; A61K 31/70
[52] U.S. Cl. ................ 424/195.1; 424/DIG. 13; 574/25; 574/458; 426/658
[58] Field of Search ............ 424/195.1, DIG. 13; 514/25, 458; 426/658

[56] References Cited

U.S. PATENT DOCUMENTS

| | | | |
|---|---|---|---|
| 145,062 | 12/1873 | Kappler | 424/195.1 |
| 149,262 | 3/1874 | Steelman | 424/127 |
| 150,129 | 4/1874 | Brewster | 424/127 |
| 153,683 | 8/1874 | Saalfeldt | 424/195.1 |
| 153,957 | 8/1874 | Hobson | 424/127 |
| 186,260 | 1/1877 | Margarit | 424/134 |
| 288,630 | 11/1883 | Green | 424/196.1 |
| 301,385 | 7/1884 | Mitchell | 424/195.1 |
| 327,847 | 10/1885 | Willis | 424/195.1 |
| 330,496 | 11/1885 | Kyte | 424/195.1 |
| 361,636 | 4/1887 | Laclaverie | 424/148 |
| 1,789,565 | 1/1931 | Sachs | 428/289 |
| 2,088,640 | 8/1937 | McIlvaine | 424/134 |
| 3,360,511 | 12/1967 | Farkas | 260/209 |
| 3,362,951 | 1/1968 | Farkas | 260/209 |
| 3,470,109 | 9/1969 | Marsh | 424/195.1 |
| 3,878,197 | 4/1975 | Maret | 424/195.1 |
| 3,892,853 | 7/1975 | Cobble | 424/195.1 |
| 3,920,816 | 11/1975 | Seegull et al. | 424/195.1 |
| 3,973,008 | 8/1976 | Sugiyama et al. | 424/195.1 |
| 4,143,162 | 3/1979 | Tanaka | 426/89 |
| 4,178,372 | 12/1979 | Coats | 424/195.1 |
| 4,369,180 | 1/1983 | Mihalovits | 424/177 |
| 4,395,942 | 2/1983 | Thompson | 100/37 |
| 4,408,364 | 10/1983 | Thompson | 15/21 |
| 4,446,131 | 5/1984 | Maughan | 424/195.1 |
| 4,465,629 | 8/1984 | Maughan | 424/195.1 |
| 4,474,763 | 10/1984 | Lubowe | 424/177 |
| 4,481,185 | 11/1984 | Grollier et al. | 424/59 |
| 4,488,482 | 12/1984 | Cottrell | 100/37 |
| 4,500,510 | 2/1985 | Goldstein | 424/80 |
| 4,505,902 | 3/1985 | Millard | 424/195.1 |
| 4,555,987 | 12/1985 | Tumlinson | 100/118 |

OTHER PUBLICATIONS

Brouse, "Aloe Vera Council Defends its Practices, Product", *FDA Consumer*, pp. 29–30, Nov., 1981.
Crewe, "The External Use of Aloes", *Minnesota Medicine*, pp. 670–673, Oct., 1937.
Bogaard, "Report on the Analysis of '*Aloe vera*' Gel", Unisearch Ltd., Jul. 1985, pp. 1–3.
Goldemberg, Compounder's Corner: News and Views, *D&CI*, Jun. 1984, pp. 22.

(List continued on next page.)

*Primary Examiner*—John W. Rollins
*Attorney, Agent, or Firm*—Robert H. Falk; Randall C. Brown

[57] ABSTRACT

Processes for producing aloe extracts including the separation of the leaves of the aloe plant into distinct portions. In particular, a first process is described for producing an aloe extract which is substantially free of anthraquinone-rich yellow sap and a second process is described for extracting the active chemical substance in the aloe plant.

The active chemical substance in the aloe plant is extracted from aloe leaves and its characteristic properties are described.

63 Claims, 28 Drawing Sheets

OTHER PUBLICATIONS

Suga et al., "The Efficacy of the Aloe Plants Chemical Constituents and Biological Activities", *Cosmetics & Toiletries*, 98: 105, (1983).

Leung, "Aloe Vera Standards Should Be Meaningful", *D&CI*, Jan. 1983, pp. 39, 80.

De Navarre, "Desiderata: Aloe and aloe", *Cosmetics & Toiletries*, 96: 12, (1981).

Gyanchandani, "Anthraquinone Drugs II: Inadvertent Acetylation of Aloe-Emodin During Preparation of Aglycones from Crude Drugs—UV, IR, and NMR Spectra of the Products, *Journal of Pharmaceutical Sciences*, 58(7): 833–835, (1969).

McCarthy, "The Metabolism of Anthracene Derivatives and Organic Acids in Selected Aloe Species", *Planta Medica*, 16(3): 348–56, (1968).

Hirata et al., "Biologically Active Constituents of Leaves and Roots of *Aloe arborescens* var. natalensis, *Z. Naturforsch*, 32c: 731–734, (1977).

Sapre, *Meiosis and Pollen Mitosis in Aloe barbadensis* Mill., *Cytologia*, 40: 525–533, (1975).

Plenge, "Aloin", *Am. Jour. Pharm.*, Oct., 1884, pp. 507–508.

Gyanchandani et al., "Anthraquinone Drugs I: Thin-Layer Chromatographic Identification of Aloes, Cascara, Senna, and Certain Synthetic Laxatives in Pharmaceutical Dosage Forms", *Journal of Pharmaceutical Sciences*, 58(2): 197–200, (1969).

Varro E. Tyler et al., Pharmacognosy, pp. 60–63, (Lea & Febiger, Philadelphia, 1981).

Arthur Osol et al., The U.S. Dispensatory and Physicians' Pharmacology, (J. B. Lippincott Co., Philadelphia, 1980), pp. 42–44.

Goodman & Gilman Eds., The Pharmacological Basis of Therapeutics, p. 984, (MacMillan Publishing Co., Inc., N.Y., 1975).

W. D. Winters et al., "Effects of Aloe Extracts on Human Normal and Tumor Cells in Vitro," Eco. Botany 35(1) at 89–95, (1981).

Ivan E. Danhof et al., "Stabilized Aloe Vera: Effect on Human Skin Cells," Drug and Cosmetic Ind. at 52–54, 105–106, (Aug., 1983).

David M. Morrow, M.D. et al., "Hypersensitivity to Aloe", Arch. Dermatol. 116 at 1064–1065, (9/80).

Melvin W. Green, "The Irritant Effect of Aloin Preliminary Note," Journal of the American Pharmaceutical Assn. 30, at 186–187, (1941).

E. R. Jansz et al., "The Aloin Content of Local Aloe Species," J. Nat'l. Sci. Coun. (Sri Lanka) 9(1) at 107–109, (1981).

F. R. Bharucha, "Effect of Prolonged Darkness on Acid Metabolism in the Leaves of Aloe Vera Linn," Sci & Cult. 22 (7) at 389–390, (1/57).

Published report submitted to the National Aloe Science Council on or about 11/11/82 by the Southwest Institute for Natural Sources, (inc. by ref.).

William F. Ganong, Review of Medical Physiology (Lange Medical Publications, Los Altos, CA) at 16–29, (1983).

Mandal et al., "Structure of the Glucomannan Isolated from the Leaves of *Aloe barbadensis* Miller," *Carbohydrate Research*, 87: 249–256, (1980).

Mandal et al., "Structure of the D-Galactan Isolated from *Aloe barbadensis* Miller," *Carbohydrate Research*, 86: 247–257, (1980).

Mandal et al., "Characterisation of Polysaccharides of *Aloe barbadenesis* Miller: Part III—Structure of an Acidic Oligosaccharide" *Indian Journal of Chemistry*, 22B: 890–893, (1983).

Zimmerman, The Essential Guide to Nonprescription Drugs (Harper & Row, NY, 1983).

James A. Duke, CRC Handbook of Medicinal Herbs, CRC Press, Inc., Boca Raton, Fla., p. 31, 1985.

R. Henry, Cosmetics and Toiletries, An Updated Review of *Aloe vera*: Allured Publishing Corp., vol. 94, pp. 42–50, 1979.

Julia F. Morton, Folk Uses and Commercial Exploitation of Aloe Leaf Pulp: Economic Botany, vol. 15, pp. 311–316, 1961.

University of California, Berkeley Wellness Letter, "Myth: Aloe Can Heal A Variety of Ailments", Published in Association with the School of Public Health, 1(6): 8, (1985).

Leung, "Aloe vera Update: A New Form Questions Integrity of Old", D & CI, Sep. 1985, pp. 42 and 44–46.

Leung, *Encyclopedia of Common Natural Ingredients Used in Food, Drugs and Cosmetics*, "Aloe (and *Aloe vera*)", pp. 24–25, (date unknown).

(List continued on next page.)

OTHER PUBLICATIONS

Cheney, "Aloe Drug in Human Therapy", *Quarterly Journal of Crude Drug Research*, 10 (1): 1523–1530, (1970).

Blomfield, "Honey for Decubitus Ulcers", *JAMA*, 224(6): 905, (1973).

Spoerke, "*Aloe vera*—Fact or Quackery", Intermountain Regional Poison Control Center, Department of Pharmacy Practice, University of Utah College of Pharmacy, Salt Lake City, UT, pp. 418–424, (1980).

Grindlay et al., "The *Aloe vera* Phenomenon: A Review of the Properties and Modern Uses of the Leaf Parenchyma Gel", *Journal of Ethnopharmacology*, 16: 117–151, (1986).

Yagi et al., "Structure Determination of Polysaccharides in *Aloe saponaria* (Hill.) Haw. (Liliaceae)", *Journal of Pharmaceutical Sciences*, 73(1): 62–65, (1984).

Radjabi-Nassab et al., "Further Studies of the Glucomannan from Aloe vahombe (Liliaceae), II, Partial Hydrolyses and JMR $^{13}$C Studies", *Biochimie*, 66: 563–567, (1984).

Rakhmanberdyeva et al., "Polysaccharides of Polygonatum. V. Isolation and Characterization of the Glucomannans of p. polyanthemum", *Khimiya Prirodnykh Soedineii*, 3: 393–394, (1982).

Chanzy et al., "Crystallization Behaviour of Glucomannan", *Biopolymers*, 21: 301–319, (1982).

Radjabi et al., "Structural Studies of the Glucomannan from *Aloe vahombe*", *Carbohydrate Research*, 116: 166–170, (1983).

Gowda et al., "Structural Studes of Polysaccharides from *Aloe vera*", *Carbohydrate Research*, 72: 201–205, (1979).

Paulsen et al., "Structural Studies of the Polysaccharide from *Aloe plicatilis* Miller, *Carbohydrate Research* 60:345–351, (1978).

Roboz et al., "A mucilage from *Aloe vera*", *Journal of the American Chemical Society*, 70: 3248–3249, (1948).

Yagi et al., "Aloe Mannan, Polysaccharide, from *Aloe arborescens* var. Natalensis", Planta Med. 31(1): 17–20, (1977).

Haq et al., "Studies of Glucogalactomannan from the Leaves of *Aloe vera*, Tourn. (Ex. Linn.)", *Bangladesh J. Sci. Ind. Res.*, 16: 68–72, (1981).

Marchessault et al., "Structural Studies on Triacetates of Mannan and Glucomannan", *Carbohydrate Polymers*, 1: 129–138, (1981).

Dea, "Specificity of Interactions between Polysaccharide Helices and $\beta$1,4—Linked Polysaccharides", *American Chemical Society*, 439–454, (1981).

Gowda, "Structural Studies of Polysaccharides from *Aloe saponaria* and Aloe Vanbalenii", *Carbohydrate Research*, 83: 402–405, (1980).

Shcherbukhin et al., "Aggregation of Glucomannans in Aqueous Solutions", *Applied Biochemistry and Microbiology*, 15(6): 892–896, (1979).

Kuznetsov et al., "Native Glucomannans of Eremarus", *Doklady Biochemistry Proceedings of the Academy of Sciences of the USSR*, 226(1): 214–216, (1976).

Rees et al., "Conformational Analysis of Polysaccharides: Stereochemical Significance of Different Linkage Positions in $\beta$-Linked Polysaccharides", *Chemical Communications*, 18: 1037–1038, (1969).

Matsuo et al., "Acetyl Groups in Native Glucomannan from Easter Lily Bulbs", *Agr. Biol. Chem.*, 38(2): 465–466, (1974).

Kato et al., "Studies on the Chemical Structure of Konjac Mannan Part I. Isolation and Characterization of Oligosaccharides from the Partial Acid Hydrolyzate of the Mannan", *Agr. Biol. Chem.*, 33(10): 1446–1453, (1969).

Segal et al., "A Reinvestigation of the Polysaccharide Material from *Aloe vera* Mucilage", *Lloydia Proceedings*, 31(4): 423–424, (1968).

Orr, "Infra-red Spectroscopic Studies of Some Polysaccharides", *Biochimica et Biophysica Acta*, 14: 173–181, (1954).

McKeown, "Aloe vera: The Quest for the 'Curvative' Missing Link", *Drug & Cosmetic Ind.*, 132: 30–32, 34–35, (1983).

Smothers, "*Aloe vera:* The Importance of Processing", *Drug & Cosmetic Ind.*, 40, 77–80, (Jan., 1983).

"The History of Aloe Vera", Reference origin unknown.

Duke et al., "Medicinal Plants of China", vol. 2, p. 396, Reference Publications, Inc. (1985).

Scarborough, Pharmacy in History: Roman Pharmacy and the Eastern Drug Trade, *American Institute of the History of Pharmacy* 24: 134–143, (1982).

(List continued on next page.)

OTHER PUBLICATIONS

Hutchens, *Indian Herbalogy of North America*, Merco, Ontario, Canada, pp. 8–10, (1981).

Spoerke, Jr., *Herbal Medications*, Woodbridge Press Publishing Company, Santa Barbara, CA, pp. 21–22, 185–186, (1981).

Gjerstad et al., "Current Status of Aloe as a Cure-All", *American Journal of Pharmacy*, 140: 58–64, (1968).

Hodge, "The Drug Aloes of Commerce, with Special Reference to the Cape Species", *Economic Botany*, 7: 99–129, (1953).

Goldberg, "The *Aloe vera* Plant", *Archives of Dermatology and Syphilology*, 49: 46, (1944).

Tchou, "*Aloe vera* (Jelly Leeks)", *Archives of Dermatology and Syphilogy*, 47: 249, (1943).

Schoff, "Aloes", *American Oriental Society Journal*, 42: 171–185, (1922).

Fantus, "Aloes as a Medicine", *Journal of the American Pharmaceutical Association*, 11: 614–619, (1922).

Day, "The Botany of Aloes; The Aloe Plant", *The Journal of the American Pharmaceutical Association*, 11: 620–621, (1922).

Snow, "Pharmaceutical Preparations of Aloes", *The Journal of the American Pharmaceutical Association*, 11: 621–623, (1922).

Stuart, "Vegetable Kingdom: Aloe Vulgaris", *Chinese Materia Medica*, The American Presbyterian Mission Press, pp. 29–30, (1911).

Wilbert, "Commercial Aloes", *The American Journal of Pharmacy*, 75: 201–214, 264–273, (1903).

Barnes, "Physiological Section", *American Journal of Botany*, 34: 10, p. 597, (1947).

Bland, "Effect of Orally Consumed Aloe Vera Juice on Gastrointesinal Function in Normal Humans", *Preventive Medicine*, Linus Pauling Institute of Science & Medicine, Palo Alto, CA, Mar./Apr., 1985.

Kandil et al., "Protection of Gastric Mucosa by *Aloe vera*, *J. Drug. Res. Egypt*, 11, No. 1–2, pp. 191–196, (1979).

Blitz et al., "*Aloe vera* Gel in Peptic Ulcer Therapy: Preliminary Report", *Journal of the American Osteopathic Association*, 62: 731–735, (1963).

United States Pharmacopedia Convention, Inc., "Compound Benzoin Tincture", *National Formulary*, USP 21, 17th Edition, pp. 99–100, 1985.

Saunders, Concanavilin: Dorland's Illustrated Medical Dictionary, 26th Edition, pp. 295, (1981).

Rubel, "Possible Mechanisms of the Healing Actions of Aloe Gel", Botanicals in Cosmetics, Terry Corporation, Melbourne, FL, vol. 98, (1983).

Fujita et al., "Bradykininase Activity of Aloe Extract", *Biochemical Pharmacology*, 25: 205, (1976).

Brasher et al., "The Effects of Prednisolone, Indonethacin, and *Aloe vera* Gel on Tissue Culture Cells", *Oral Surgery, Oral Medicine, and Oral Pathology*, 27: 122–128, (1969).

Robson et al., "Myth, Magic, Witchcraft, or Fact? *Aloe vera* Revisited", *J. Burn Care Rehab.*, 3: 157–163, (1982).

Cera et al., "The Therapeutic Efficacy of *Aloe vera* Cream (Dermaide Aloe®) in Thermal Injuries: Two Case Reports", *Journal of the American Animal Hospital Association*, 16: 768–772, (1980).

Ship, "Is Topical *Aloe vera* Plant Mucus Helpful in Burn Treatment?", *JAMA*, 238: 1770, (1977).

Goff et al., "Measuring the Effects of Topical Preparations Upon the Healing of Skin Wounds", *Journal of the Society of Cosmetic Chemists*, 15: 509–518, (1964).

Ashley, "The Use of *Aloe vera* in the Treatment of Thermal and Irradiation Burns in Laboratory Animals and Humans", *Plastic and Reconstructive Surgery*, 20: 383–396, (1957).

Lushbaugh et al., "Experimental Acute Radiodermatitis following Beta Irradiation V. Histopathological Study of the Mode of Action of Therapy with *Aloe vera*, *Cancer*, 6: 690–698, (1953).

Rowe et al., "Further Observations on the Use of *Aloe vera* Leaf in the Treatment of Third Degree X-Ray Reactions", *Journal of the American Pharmaceutical Association*, 30: 266–269, (1941).

Rowe, "Effect of Fresh *Aloe vera* Jell in the Treatment of Third-Degree Roentgen Reactions on White Rats", *Journal of the American Pharmaceutical Association*, 29: 348–350, (1940).

Mandeville, "Aloe vera in the Treatment of Radiation Ulcers of Mucous Membranes", *Radiology*, 32: 598–599, (1939).

(List continued on next page.)

OTHER PUBLICATIONS

Crewe, "Aloes in the Treatment of Burns and Scalds", *Minnesota Medicine*, 21: 538-539, (1939).

Loveman, "Leaf of *Aloe vera* in Treatment of Roentgen Ray Ulcers", *Archives of Dermatology and Syphilology*, 36: 838-843, (1937).

Wright, "*Aloe vera* in the Treatment of Roentgen Ulcers and Telangiectasis", *JAMA*, 106: 1363-1364, (1936).

Collin et al., "Roentgen Dermatitis Treated with Fresh Whole Leaf of *Aloe vera*", *American Journal of Roentgenology and Radium Therapy*, 33: 396-397, (1935).

Collins, "Alvagel as a Therapeutic Agent in the Treatment of Roentgen and Radium Burns", *The Radiological Review and Chicago Medical Recorder*, 57: 137-138, (1935).

Cock, "Aloes as a Local Sedative", *The British Medical Journal*, 2: 255, (1918).

Gjerstad, "Chemical Studies of *Aloe vera* Juice—I: Amino Acid Analysis", *The University of Texas at Austin College of Pharmacy*, 28: 311-315, (1971).

Bouchey et al., "Chemical Studies of *Aloe vera* Juice II: Inorganic Ingredients", *Quarterly Journal of Crude Drug Research*, 9: 1445-1454, (1969).

Report of the Joint Committee of the Pharmaceutical Society and the Society for Analytical Chemistry, "Recommended Methods for the Evaluations of Drugs: The Chemical Assay of Aloes", *Analyst*, 90: 593-596, (1965).

Fairbairn et al., "The Quantitative Conversion of Barbaloin to Aloe-Emodin and its Application to the Evaluation of Aloes", *The Journal of Pharmacy and Pharmacology*, 15: 325-328, (1963).

Makino et al., "Studies on the Constituents of *Aloe arborescens* Mill. var. natalensis Berger. I. The Structure of Aloearbonaside, a Glucoside of a New Type Naturally Occurring Chromene", *Chem. Pharm. Bull.*, 21: 149-156, (1973).

Makino et al., "Studies on the Constituents of *Aloe arborescens* Mill. var. Natalensis Berger II, The Structures of Two New Aloesin Esters", *Chem. Pharm. Bull.*, 22: 1565-1570, (1973).

Tilden, "Preliminary Notice of Some Products from Natal Aloes", *The Pharmaceutical Journal and Transactions*, Series 3, vol. 2: 951-952, (1872).

Bovik, "Aloe vera: Panacea or Old Wives' Tale?", *Texas Dental Journal*, 84: 13-16, (1966).

Zawahry et al., "Use of Aloe in Treating Leg Ulcers and Dermatoses", *International Journal of Dermatology*, 12(1): 68-73, (1973).

Hegazy et al., "The Use of *Aloe vera* Extract in the Treatment of Experimental Corneal Ulcers in Rabbit", *J. Drug. Res. Egypt*, 10 (1-2): 199-209, (1978).

Galal et al., "*Aloe vera* and Gastrogenic Ulceration", *J. Drug Res. Egypt*, 7(2): 73-77, (1975).

Soeda et al., "Studies on the Effect of Cape Aloe for Irradiation Leucopenia", 24, 1109-1110, (1964).

Jhaveri et al., "Clinical Evaluation of Infertility Associated with Irregular Menstrual Cycles Treated with an Indigenous Preparation", *Recent Advances in Human Reproduction*, Arthur Campos da Paz, et al., Eds., Exerpta Medica, 1976, pp. 61-65.

Barondes, "Lectins: Their Multiple Endogenous Cellular Functions", *Ann. Rev. Biochem.*, 50: 207-231, (1981).

Suzuki et al., "Purification and Characterization of Two Lectins from *Aloe arborescens* Mill *J. Biochem.*, 85: 163-171, (1979).

Fujita et al., "Specific Reaction of Aloe Extract with Serum Proteins of Various Animals", *Experientia*, 34: 523-524, (1978).

Gordon et al., "The Role of Concanavalin A Dissociation on Positive Cooperativity of Binding with Native and Fixed Erythrocytes", *The Journal of Biological Chemistry*, 254(6): 1932-1937, (1978).

Reeke et al., "The Covalent and Three-Dimensional Structure of Concanavalin A", *The Journal of Biological Chemistry*, 250(4): 1525-1547, (1975).

Agrawal et al., "Protein-Carbohydrate Interaction, IVIII, The Preparation and Properties of Acetylated Concanavalin A, the Hemogglutinin of the Jack Bean", *Biochemistry*, 7(12): 4211-4218, (1968).

Sharon, "Lectins", *Scientific American*, 236: 108-119, (1977).

Northway, "Experimental Use of *Aloe vera* Extract in Clincal Practice", *Veterinary Medicine/Small Animal Clinican*, Jan. 1975, p. 89.

Clinical Data, "The Local Action of Aloes on Regeneration", *Journal of the American Veterinary Medical Association*, 99: 296, (1941).

McLaughlin, "Roentgen Ray Dermatitis Treated with Ointment Containing Viosterol", *Archives of Dermatology and Syphilogy*, 34: 901-903, (1936).

(List continued on next page.)

OTHER PUBLICATIONS

Flagg, "*Aloe vera* Gel in Dermatological Preparations", *American Perfumes and Aromatics*, 74: 27–28, 61, (1959).

Fine, "Cultivation and Clinical Applications of *Aloe vera* Leaf", *Radiology*, 31: 735–736, (1938).

Hamilton, "Acute Vesicular Dermatitis Caused by Curacao Aloes", *The Medical Journal of Australia*, 1: 302–303, (1932).

Anderson, "*Aloe vera* Juice: A Veterinary Medicament?", *The Compendium on Continuing Education for the Practicing Veterinarian*, 5: 364–368, (1983).

Grieve, "Aloes", *A Modern Herbal*, vol. I, Dover Publications, Inc. New York, 1971, pp. 26–29.

Ivy et al. (I), "The Effect of Aloes and Podophyllum (Resin) (Carter's Little Liver Pills) on the Output of Bilirubin and Cholic Acid in Duodenal Drainage in Constipated Human Subjects, *Quaterly Bulletin, Northwestern University Medical School*, 19: 189–193, (1945).

Ivy et al. (II), "Do Aloes and Podophyllum (Carter's Little Liver Pills) Increase the Flow of Bile into the Duodenum?", *Gastroenterology*, 5: 27–33, (1945).

Hazleton, "The Influence of Aloe and Podophyllum on the Flow of Hepatic Bile in the Dog", *Journal of the American Pharmaceutical Association*, 31: 53–56, (1942).

Ivy et al. (III), "The Effect of Aloes and Podophyllum and Carter's Little Liver Pills on Bile Formation", *Quarterly Bulletin, Northwestern University Medical School*, 16: 197–202, (1942).

Viehoever, "Evaluation of Aloe", *Am. Jour. Pharm.*, 107:47–72, (1935).

Munch, *Bioassays: A Handbook of Quantitative Pharmacology*, The Williams and Wilkins Company, Baltimore, 1931, pp. 769–781.

Gathercoal et al., "What is Aloes, U.S.P.?, *Journal of the American Pharmaceutical Association*, 11: 523–526, (1922).

Day et al., "Botany of Aloes", Pharmacognosy of Aloes", Therapeutics of Aloes, and Preparations of Aloes, *Journal of The American Pharmaceutical Association*, 11: 462–463, (1922).

Nosokomos, "On the Use and Abuse of Aloes", *London Medical Gazette*, 4: 139–143, (1829).

Meadows, "Formulating Cosmetics with Aloe Vera", *Drug & Cosmetic Ind.*, 132: 36–40, (1983).

Noll, "Today's and Tomorrow's Cosmetics with Aloe Vera Gel", *Journal of the Society of Cosmetic Chemists*, 34: 174–175, (1983).

Moroni, "Aloe in Cosmetic Formulations", *Cosmetic Technology*, Sep. 1982, pp. 40–45.

Schoen, "Aloe vera Cosmetics", *The AMA Book of Skin and Hair Care*, J. B. Lippincott Company, New York, 1977, pp. 41–42.

Leung, "Aloe Vera in Cosmetics", *Drug & Cosmetics Ind.*, 1977, pp. 34–35, 154–155.

Hoffenberg, "*Aloe vera* An Old Herbal Medication—New in Cosmetics", *Soaps-Oils-Fats-Waxes*, 17: 499–502, (1979).

Trachtenberg, "Cytochemical and Morphological Evidence for the Involvement of the Plasma Membrane and Plastids in Mucilage Secretion in *Aloe arborescens*", *Annals of Botany*, 53: 227–236, (1984).

Vij et al., "Cytogenetical Investigations into Some Garden Ornamentals II. The Genus Aloe L.", *Cytologia*, 45: 515–532, (1980).

Abraham et al., "Occurrence of Triploidy in *Aloe vera* Tourn. ex Linn.", *Current Science*, 48: 1001–1003, (1979).

Bartakke et al., "Crassulacean Acid Metabolism and Photosynthesis in *Aloe barbadensis* Mill", *Photobiology*, 42B(4&5):227–233, (1976).

Lu et al., "Lateral Thickening in the Stem of *Agave rigida* Mill. and *Aloe vera* L., *Taiwania*, 21(2): 204–219, (1976).

Groenewald et al., "Callus Formation and Plant Regeneration from Seed Tissue of *Aloe pretoriensis* Pole Evans", *Z. Pflanzenphysiol. Bd.* 75, S. 270–272, (1975).

Gupta et al., "Chromosomal Aberrations Induced by Maleic Hydrazide in *Aloe vera*", *Acta Botanica Academiae Scientiarum Hungaricae*, 17: 51–58, (1971).

Gunther, "The Greek Herbal of Dioscorides", Hafner Publishing Company, New York, 1968, pp. 257–258.

Vig, "Spontaneous Chromosome Abnormalities in Roots and Pollen Mother Cells in *Aloe vera* L.", *Bulletin of the Torrey Botanical Club*, 95(3): 254–261, (1968).

Vyas, "Staminal Abnormalities in *Aloe vera* Linn.", *Science and Culture*, 30: 145–146, (1964).

Rowe et al., "A Phytochemical Study of *Aloe vera* Leaf", *Journal of the American Pharmaceutical Association*, 30: 262–265, (1941).

(List continued on next page.)

OTHER PUBLICATIONS

Marshak, "Chromosomes and Compatibility in the Aloinae", *American Journal of Botany*, 21(9): 592–597, (1934).

Holdsworth, "Chromones in Aloe Species", Department of Chemistry, University of Papua and New Guinea, pp. 322–325.

Excerpt from Brochure of Dr. Madis Laboratories, Inc., South Hackensack, NJ, "Veragel".

Waller et al., "A Chemical Investigation of *Aloe barbadensis* Miller", Proc. Okla. Acad. Sci. 58: 69–76, (1978).

Rauwald et al., "7-Hydroxyaloin: the Leading Substance from *Aloe barbadensis* in Ph. Eur. III", *Arch. Pharm. (Weinheim)*, 315: 477–478, (1982).

Rauwald, "Preparative Separation of the Diastereomeric Aloins by Droplet Counter-Current Chromatography", *Arch. Pharm.* (Weinheim), 315: 769–772, (1982).

Yagi et al., "Effect of Aloe Lectin on Deoxyribonucleic Acid Synthesis in Baby Hamster Kidney Cells", *Experientia*, 41: 669–671, (1985).

*Physiological Effects of Food Carbohydrates*, Jeanes et al., Ed., American Chemical Society, Washington, DC 1975, pp. 296–311.

Flesch, "Mucopolysaccharides in Human Epidermis," *Journal of the Society of Cosmetic Chemists*, 10(1): 154–158, (1959).

Gorin, "Assignment of Signals of the Carbon-13 Magnetic Resonance Spectrum of a Selected Polysaccharide: Comments on Methodology", *Carbohydrate Research*, 39: 3–10, (1975).

Bible, *Interpretation of NMR Spectra An Empirical Approach*, Plenum Press, New York, 1965, pp. 7–48.

N, Veragel Bulletin issued 1982, (South Hackensack, NJ), Madis Laboratories.

Harding, Aloes of the World: A Checklist, Index and Code, *Excelsa* 9: 57–59, (1979).

Reynolds, *Aloes of Tropical Africa and Madagascar*, The Trustees The Aloe Book Fund, Mbabane Swaziland.

Bruce, *South African Medical Journal*, 41: 984, (1967).

Morrow et al., *Archives of Dermatology*, 116: 1064–1065, (1980).

Saleh et al., *Corrosion Prevention and Control*, 9–10, (1983).

Mapp et al., *Planta Medica*, 18: 361–365, (1970).

Rauwald, *Archives Pharmazie*, 315: 477–478, (1982).

Bruce, *Excelsa* 5: 57–68, (1975).

Suga et al., *Cosmetics and Toiletries*, 98: 105–108, (1983).

Danof et al., Stabilized Aloe Vera: Effect on Human Skin Cells, *Drug and Cosmetic Ind.* at 52–54, 105–106, (Aug. 1983).

Mandal et al., Structure of the Glucomannan Isolated from the Leaves of Aloe barbadensis Miller, *Carbohydrate Research*, 87: 249–256, (1980).

Mandal et al., Structure of the D-Galactan Isolated from Aloe barbadensis Miller, *Carbohydrate Research*, 86: 247–257, (1980).

Mandal et al., Characterisation of Polysaccharides of Aloe barbadensis Miller: Part III-Structure of an Acidic Oligosaccharide, *Indian Journal of Chemistry*, 22B: 890–893, (1983).

Yagi et al., Structure Determination of Polysaccharides in Aloe Saponaria (Hill.) Haw. (Liliaceae), *Journal of Pharmaceutical Sciences*, 73(1): 62–65, (1984).

Yagi et al., Aloe Mannan, Polysaccharide, from Aloe Arborescens var. Natalensis, *Planta Med.* 31(1): 17–20, (1977).

Haq et al., Studies on Glucogalactomannan from the Leaves of Aloe vera, Tourn. (Ex. Linn), *Bangladesh J. Sci. Ind. Res.*, 16: 68–72, (1981).

Kato et al., Studies on the Chemical Structure of Konjac Mannan Part I. Isolation and Characterization of Oligosaccharides from the Partial Acid Hydrolyzate of the Mannan, *Agr. Biol. Chem.*, 33(10), 1446–1453, (1969).

Fujita et al., Bradykininase Activity of Aloe Extract, *Bio-Chemical Pharmacology*, 25: 205, (1976).

Yagi et al., "Effect of Aloe Lectin on Deoxyribonucliec Acid Synthesis in Baby Hamster Kidney Cells", *Experientia*, 41: 669–671, (1985).

Tyler et al., *Pharmacognosy* at pp. 60–63, (Lea and Febinger, Philadelphia, 1981).

Osol et al., *The United States Dispensatory and Physician's Pharmacology*, at pp. 42–43, (J. B. Lippencott Co., Philadelphia, 1980).

Goodman and Gilman, Eds., *The Pharmacological Basis of Therapeutics*, at 984, (MacMillan Publishing Co., New York, 1975).

Cole et al., *Glossary of Indian Medicinal Plants*, Council of Scientific and Industrial Research, New Delhi.

(List continued on next page.)

OTHER PUBLICATIONS

Ship, *Journal of the American Medical Association*, 238: 1770–1772, (1977).

Morton, *Atlas of Medicinal Plants of Middle American Bahamas to Yucatan*, Charles C. Thomas, Publisher, 78–80, (1981).

Diez-Martinez, La Zabila, *Communicado No. 46 Sobre Recursos Bioticos Potenciales del Pais*, INIREB, Mexico, (1981).

Dastur, *Medicinal Plants of India and Pakistan*, D. B. Taraporevala Sons & Co., Private Ltd., Bombay 16–17, (1962).

Mackee, *X-Rays and Radium in the Treatment of Diseases of the Skin*, 3rd Ed., Lea and Febiger, Philadelphia, 319–320, (1938).

Rovatti et al., *Industrial Medicine and Surgery*, 28: 364–368, (1959).

Zawahry et al., *Quotations from Medical Journals on Aloe Research*, Ed. Max. B. Skousen, Aloe Vera Research Institute, Cypress, Calif., 18–32, (1977).

Cera et al., *Journal of the American Animal Hospital Association*, 18: 633–638, (1982).

Grindley and Reynolds, *Journal of Ethnopharmacology*, 16: 117–151, (1986).

*U.S. Pharmacopeia*, 20th Revision, The National Formulary, 14th Edition, United States Pharmacopeial Convention, Inc., Rockville, Md., Jul. 1, 1980.

Robson et al., *Journal of Burn Care Rehabilitation*, 3: 157–163, (1982).

Rowe et al., *Journal of the American Pharmaceutical Association*, 30: 263–266, (1941).

Roboz et al., *Journal of the American Chemical Society*, 70: 3248–3249, (1948).

Waller et al., *Proceedings of Oklahoma Academy of Science*, 58: 69–76, (1978).

Eberendu et al., *The Chemical Characterization of Carrisyn* (in preparation).

Mandal et al., *Carbohydrate Research*, 87: 249–256, (1980b).

Gowda et al., *Carbohydrate Research*, 72: 201–205, (1979).

Segal et al., *Lloydia Proceedings*, 31, 423–424, (1968).

Leung, *Excelsa*, 8: 65–68, (1978).

Henry, *Cosmetics and Toiletries*, 94: 42–50, (1979).

Freytag, *Pharmazie* 9: 705–712, (1954).

Kawashima et al., *Chemical Abstracts*, 93: 13075, (1979).

Goto et al., *Gann* 63: 371–374, (1972).

Gialdroni-Grassi, G. *International Archives of Allergy and Applied Immunology*, 76, (Suppl. 1): 119–127, (1985).

Ohno et al., *Chemical and Pharmaceutical Bulletin*, 33: 2564–2568, (1985).

Leibovici et al., *Chemico-Biological Interactions*, 60: 191–200, (1986).

Ukai et al., *Chemical and Pharmaceutical Bulletin*, 31(2): 741–744, (1983).

Leibovici et al., *Anticancer Research*, 5: 553–558, (1985).

Trowell et al., Editors *Refined Carbohydrate Foods and Diseases*, London, Academic Press, 207–209, (1975).

Trowell et al., Editors, *Refined Carbohydrate Foods and Disease*, London, Academic Press, 207–209, (1975).

Kay et al., *American Journal of Clinical Nutrition*, 30: 171–175, (1977).

Zavoral et al., *American Journal of Clinical Nutrition*, 38: 285–294, (1983).

Jenkins et al., *Lancet*, 2: 779–780, (1977).

Kuhl et al., *Diabetes Care*, 6(2): 152–154, (1983).

Rethy et al., *Annales Immunologiae Hungaricae*, 21: 285–290, (1981).

Chihara et al., *Nature*, 222: 687–689, (1969).

Schwartzman, *Proceedings of the Society for Experimental Biology and Medicine*, 29: 737–741, (1932).

Rethy, *X. International Congress of Microbiology; Moscow*, 642, (1966).

Suzuki et al., *Journal of Pharmacbio-Dynamics*, 7: 492–500, (1984).

Chihara, "The antitumor Polysaccharide Lentinan: An Overview, "Manipulation of Host Defense Mechanisms", ed. by Aoki et al., *Excerpta Medica*, North Holland, 1–16, (1981).

Sasaki et al., *Carbohydrate Research*, 47: 99–104, (1976).

Matsuzaki et al., *Makromol. Chem.*, 186: 449, (1985).

Matsuzaki et al., *Makromol. Chem.*, 187: 325–331, (1986).

Hara et al., *Carbohydrate Research*, 111: 143, (1982).

Baba et al., *Journal of Immunopharmacology*, 8 (6): 569–572, (1986).

Ishizuka et al., *Journal of Antibiotics*, 33: 642–652, (1980).

(List continued on next page.)

OTHER PUBLICATIONS

Jolles et al., *Acta. Univ. Int. Cancer*, 16: 682–685, (1960).

Suemasu et al., *Gann*, 61: 125–130, (1970).

Jolles et al., *British Journal of Cancer*, 17: 109–115, (1963).

Yamamoto et al., *Japanese Journal of Experimental Medicine*, 54(4): 143–151, (1984).

Sugawara et al., *Microbiological Immunology, 28(7): 831–839, (1984)*.

Dorries et al., *European Journal of Immunology*, 4: 230–233, (1974).

Sugawara et al., *Cell Immunology*, 74: 162–171, (1982).

Wooles et al., *Science*, 142: 1078–1080, (1963).

Pospisil et al., *Experientia*, 38: 1232–1234, (1982).

Burgaleta et al., *Cancer Research*, 37: 1739–1742, (1977).

Maisin et al., *Radiation Research*, 105: 276–281, (1986).

Lackovic et al., *Proceedings for the Society for Experimental Biology and Medicine*, 134: 874–879, (1970).

Seljelid et al., *Experimental Cell Research*, 131: 121–129, (1981).

Bogwald et al., *Scandanavian Journal of Immunology*, 20: 355–360, (1984).

Wirz et al., *Clinical Immunology and Immunopathy*, 33: 199–209, (1984).

Suzuki et al., *Journal of Antibiotics*, 32(12): 1336–1345, (1979).

Suzuki et al., *Proceedings of the Society for Experimental Biology and Medicine*, 149: 1069–1075, (1975).

Saito et al., *Antimier, Agent & Chemotherapy*, 10(1): 14–19, (1976).

Rubel, *Cosmetics and Toiletries*, 98: 109–114, (1983).

Ukai et al., *Journal of Pharmaco-bio-Dynamics*, 6: 983–990, (1983).

Saeki et al., *Japanese Journal of Pharmacology*, 24: 109–118, (1974).

Arita et al., *Journal of Pharmacology*, 24: 861–869, (1974).

Rocha et al., *Biochemical Phamacology*, 18: 1285–1295, (1969).

Yagi et al., *Planta Medica*, 31: 17–20, (1977).

Ovodova, *Khim. Prior. Soedin*, 83: 93833, (1975).

Winters et al., "Effects of Aloe Extract on Human Normal and Tumor Cells in Vitro", *ECO. Botany*, 35(1) at 89–95, (1981).

Danhoff et al., "Stabilized Aloe Vera: Effect on Human Skin Cells", *Drug and Cosmetic Ind.* at 52–54, 10–106, (Aug., 1983).

Green, Melvin, "The Irritant Effect of Aloin Preliminary Note", *Amer. Pharm. Assoc.* 30: at 186–187, (1941).

Jansz et al., "The Aloin Content of Local Aloe Species", *J. Natn. Sci. Coun.* (Sri Lanka), 9(1): at 107–109, (1981).

Bharucha, "Effect of Prolonged Darkness on Acid Metabolism in the Leaves of Aloe vera Linn", *Sci. and Cult.* 22(7): at 389–390.

National Aloe Science Council Report Submitted by the Southwest Institute for Natural Sources, (Nov. 11, 1982).

Ganong, "Review of Medical Physiology", (Lange Medical Publications, Los Altos, CA) at 16–29, 984, (1983).

Fischer, John, *U.S. Pharmacist*, at pp. 37–45, (Aug. 1982).

Gaurhari et al., "Structure of the D-Galactan Isolated from Aloe Barbadensis Miller", (Elsevier Scientific Publishing Company, Amsterdam, 1980), 86 at 247–257.

Gaurhari et al., "Characterisation of Polysaccharides of Aloe Barbadnesis Miller: Part III—Structure of an Acidic Oligosaccharide", (*Indian Journal of Chemistry*, Sep. 1983), 22B at 890–893.

NO STATISTICALLY RELEVANT FUNCTION CAN
FIT THE DATA BECAUSE OF RANDOMNESS

BEST FIT: % YIELD = 0.048 LOG(1/$T_{GEL}$) +0.314
$R^2$ = 0.565

PROCESSES FOR PREPARATION OF ALOE PRODUCTS, PRODUCTS PRODUCED THEREBY AND COMPOSITIONS THEREOF

RELATED APPLICATIONS

This application is a division of parent application Ser. No. 869,261, filed June 5, 1986 now U.S. Pat. No. 4,735,935, which is a continuation-in-part of an application filed Dec. 17, 1985, now abandoned, Ser. No. 810,025, which is a continuation-in-part of an application filed July 12, 1985, now abandoned, Ser. No. 754,859, which is a continuation-in-part of an application filed June 28, 1985, now abandoned, Ser. No. 750,321, which is a continuation-in-part of an application filed Sept. 12, 1984, now abandoned, Ser. No. 649,967, which is a continuation of an application filed May 7, 1982, now abandoned, Ser. No. 375,720 now abandoned. Said application Ser. No. 810,025 being entitled "Processes for Preparation of Aloe Products and Products Produced Thereby". Said applications Ser. Nos. 754,859; 750,321; 649,967; and 375,720 being entitled "Process for Preparation of Aloe Vera Products".

BACKGROUND OF THE INVENTION

1. Field of the Invention

This invention pertains to the field of processing aloe plants and removing portions of said plant for processing same into compositions for topical and internal applications, and compositions of matter comprising said portions of aloe.

2. Description of the Prior Art, and Other Information

Approximately 325 species of Aloe are known, and most are indigenous to Africa. *Aloe barbadensis* is native to northern Africa, and was introduced into the island of Barbados about 1630. A variety of *Aloe barbadensis* (called *Aloe chinensis* Baker) was introduced by William Anderson into Curacao in 1817 from China. It was cultivated in Barbados for its laxative fraction until the middle of the nineteenth century, when the industry began to wane. Curacao aloe, which is often called Barbados aloe, comes from the Dutch islands of Aruba and Bonaire. The market for laxative aloe diminished as better and safer laxatives were developed.

The plant contains two separate juice materials. One is made from the clear cellular gel and the second, a yellow juice, is contained in the pericyclic cells of the vascular bundles located at the junction between the rind (cortex) and the internal fillet (FIGS. 1 and 2-1 is the clear cellular gel, 2 the yellow juice containing anthraquinones, 3 is the rind).

For centuries the yellow juice has been dried and used as a laxative. For example, in the Dutch islands of Aruba and Bonaire, leaves are cut in March and April, then placed cut end downward on a V-shaped trough which is inclined so that the latex can be fed into a cooking vessel. Varro E. Tyler, PHARMACOGNOSY at pp. 60-63 (Lea and Febiger, Philadelphia, 1981). The dried latex of the leaves of *Aloe barbadensis* Miller or other Aloes ranges in color from reddish-black to brownish-black to dark brown in color. The taste of each variety of dried latex is nauseating and bitter; also the odor is characteristic and disagreeable. It contains a number of anthraquinone glycosides; the principal one is called barbaloin (aloe-emodin anthrone C-10 glucoside). This dried latex, that has been sold for centuries as a laxative, is commonly called aloe or aloes.

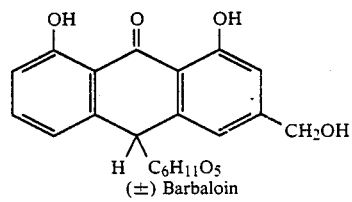

(±) Barbaloin

The active laxative constituents vary quantitatively and qualitatively according to the species and environment growing conditions. For example, Curacao aloe contains two and one half times as much aloe-emodin when compared to Cape Aloe, and Curacao aloe contains an appreciable amount of free chrysophanic acid not present in other types of aloe (Tyler, op. cit.). Many companies sell Aloe products that contain a large amount of the yellow sap even claiming them to be beneficial. Both juices become mixed together by the juice extraction process which is used by many producers.

The following species of Aloe have been used commercially for their yellow sap, which was dried and used as a laxative. Arthur Osol et al., THE UNITED STATES DISPENSATORY AND PHYSICIANS' PHARMACOLOGY, (J. B. Lippencott Co., Philadelphia, 1980) at pp. 42-43:

"1. *Aloe Perryi* Baker.—The true Socotrine aloe is a perennial herb, growing abundantly on the island of Socotra especially in the limestone tracts, from the seal level to an altitude of 3,000 feet and also found in eastern Africa and in Arabia. It has a trunk one foot high which bears on its summit a dense rosette of pale green or reddish, succulent, lanceolate leaves with brown-tipped marginal spines.

"2. *Aloe barbadensis* Mill.—(A. vera "L"; A. vulgaris Lamarck).—This species, which is the source of Curacao aloe, has a very short, woody stem, and lanceolate embracing leaves, of glaucous green color, with hard, pale spines. It has bright yellow flowers arranged in a species inflorescence. *A. barbadensis* is a native of southeastern Europe, northern Africa, and Madagascar. It is cultivated in Italy, Sicily, Malta, and especially in the West Indies.

"3. *Aloe ferox* Miller, and one of the three South African, tree-like species yielding Cape aloe, is one of the tallest species of the genus. [sic] It has a forked stem 5 to 15 feet long, 4 to 6 inches in diameter; furnished at the top with a dense rosette containing 30 to 50 lanceolate leaves 1.5 to 2 feet long, with prickles.

4. *Aloe Africana* Mill., an aborescent South African species, has a simple tall trunk which bears on its summit a few triangular-oblong, glaucous, green leaves with large, horny marginal teeth. It is a native of the Cape Colony.

"5. *Aloe spicata* baker. (A. Eru var. cornuta Berger) is a tall, branched aloe indigenous to tropical southern Africa. It possess pale, glossy, fleshy leaves with white blotches and a panicle of campanulate yellow flowers."

The current status of the yellow sap portion of Aloe as a laxative is best summarized by the text of Goodman and Gilman, as follows:

"The yellow sap has not been subjected to controlled clinical comparison with the other anthraquinones but has the reputation of being the most irritating of these cathartics. It produces considerable griping and pelvic congestion, and excessive doses may cause nephritis. It is still described in the U.S.P., but only for pharmaceutical reasons. Both aloe and aloin, a mixture of active glycosides, should be abandoned."

Goodman and Gilman, Eds., THE PHARMACOLOGICAL BASIS OF THERAPEUTICS, at 984, (MacMillan Publishing Co., Inc. New York 1975.)

Aloe is a tropical or subtropical plant characterized by lance-shaped leaves with jagged edges and sharp points. For centuries, this plant has been considered to have, and as been used for its medicinal and therapeutic properties without any clear understanding or scientific analysis of the bases for such properties. Note U.S. Pat. Nos. 3,892,853 to Cobble and 4,178,372 to Coats, both of which teach a process for producing an alleged stabilized (i.e. bacteriologically stable) aloe juice by extracting the mucilage from the aloe leaves and adding a mild oxidant ($H_2O_2$). No reference is made in these patents to removing yellow sap, or to adverse properties in aloe juice due to the presence of yellow sap. In fact, both the '853 and '372 patents attribute adverse properties prior to processing to beta "and perhaps" alpha globulin proteins (col. 3, lines 41–43 of the '853; col. 3, lines 42–47 of the '372). Furthermore, attempts to produce various commercial products from extracts and derivatives of the aloe plant have met with varying degrees of success and failure.

THE PROBLEMS TO WHICH THE INVENTION IS ADDRESSED

Because of this lack of knowledge about the aloe plant and its characteristics, previous methods employed for the processing of the plant and its components resulted in end products which did not consistently achieve desired results because of the presence of yellow sap, which was known to have a laxative effect, Goodman and Gilman, op cit. For example, conventional state of the art processes for the production of various aloe products typically involve crushing (pressure rollers), grinding (e.g., use of Thompson aloe leaf slitter), or pressing (TCX) pressure extruder) of the entire leaf of the aloe plant to produce an aloe vera juice, followed by various steps of filtration and stabilization of the juice. The resulting solution was then incorporated in, or mixed with, other solutions or agents to produce the desired end use product which could be, for example, a cosmetic, a health food drink, or a topical ointment.

The principal disadvantage of such state of the art processes is the failure to recognize, and to take into account, that different components of the aloe leaf have characteristics that may not only be inconsistent with the intended use of the final product, but in many instances are deleterious to such use. For example, research conducted incident to the process of the present invention revealed that certain components of the aloe leaf produce cytotoxic activity, U.S. Pat. No. 3,892,853, while other components stimulate cell growth. In other instances it was discovered that components of the aloe leaf which are advantageously used in the production of a skin ointment can actually be harmful if used in the production of a drink to be ingested. Winters et al. concluded that "The cytotoxic effects of commercially prepared *aloe vera* gel fractions on normal human and tumor cells in culture suggest that these commercial preparations contain substances introduced during commercial processing which can alter the levels of lectin-like activities and can markedly disrupt the in vitro attachment and growth of human cells". Id at 95. Winters et al. reported to the instant applicant that he used material received from Coats as a commercial stabilized aloe preparation.

Winters et al. found that freshly extracted aloe juice was beneficial to growth of human skin (fibroblast) cells while state-of-the art commercial aloe preparations were actually toxic: "In contrast, fractions of 'stabilized' aloe vera gel were equally cytotoxic for human normal and tumor cells in vitro". W. D. Winters et al., "Effects of aloe Extract on Human Normal and Tumor Cells In Vitro", ECO. BOTANY 35(1) at 89–95 (1981).

By using prior art processes which produced a juice or extract from essentially the entire leaf of the aloe vera plant (or at least a substantial portion thereof), containing an adulterated mixture or conglomeration of the different characteristic portions of such leaf, the resulting product necessarily included components which, while useful for certain end products, actually constituted contamination for certain other end uses. Even if the contamination that was present did not constitute a hazard, at the very least, the resulting juice constituted a diluted mixture of components, rather than a concentrate of desired properties for certain other end uses.

More recent studies indicate that the yellow sap is also toxic to human skin cells. Ivan E. Danhof et al., "Stabilized *Aloe Vera*: Effect on Human Skin Cells", DRUG AND COSMETIC IND. at 52–54, 105–106 (August, 1983) (not admitted to be prior art to the present invention) and should be minimized in topical products where it can come in contact with broken or damaged skin. Idiosyncratic hypersensitivity has been demonstrated in processed *Aloe vera* gel that consists of a variable mixture of yellow sap. David M. Morrow, M.D., et al, "Hypersensitivity to Aloe", ARCH. DERMATOL. 116, at 1064–1065 (Sept. 1980). The untoward effects of yellow sap aloin on human tissue culture is consistent with the inflammatory responses on the intestinal mucosa reported over forty years ago. Melvin W. Green, "The Irritant Effect of Aloin Preliminary Note", AMER. PHAR. ASSOC. 30, at 186–187 (1941). This problem is further compounded by the fact that the yellow sap (aloin) content of individual plants is variable and can vary several hundred percent. E. R. Jansz et al, "The Aloin Content Of Local Aloe Species", J. NATN. SCI. COUN. (Sri Lanka) 9(1) at 107–109 (1981). Jansz et al. specifically report that Aloin [yellow sap] was "commonly used as a laxative".

A second problem associated with processing *Aloe vera* plants is the effect of darkness on the acid content of the leaves. In the field, leaves are collected and stacked, awaiting processing. The Aloe leaves on the bottom are maintained in darkness. Some leaves may be in darkness for days to weeks before processing. In a matter of hours, the acid content can increase several times. See F. R. Bharucha, "Effect on Prolonged Darkness on Acid Metabolism in the Leaves of *Aloe Vera Linn*", SCI. AND CULT. 22(7) at 389–390. This affects the taste and effectiveness of the *Aloe vera* products (too much acid can cause burning or skin irritation).

Coats '372 taught that the aloe plant should be grown under "conditions" to minimize variation in gel substances. However, even under controlled conditions, these substances can vary by more than a hundred percent. Varying mineral content in processed aloe juice, i.e., varying salt content is deleterious to final product preparation in many applications because of lack of consistency of density (e.g. thickness) and even health reasons (burning and irritation because of substantial salt deviations in final product, e.g., hair shampoo formulations). Chemical stability of aloe products is also affected by varying mineral content of extracted aloe juice. Too much salt in extracted aloe juice can produce separation of phases in final topical aloe formulations. This third problem—consistency in aloe juice composition because of seasonal variations in raw aloe plant mineral content—is brought out by a published report submitted to the National Aloe Science Council on or about Nov. 11, 1982 by The Southwest Institute For Natural Sources, which report is incorporated herein by reference in its entirety, which demonstrates the variable mineral concentration found in Aloe leaves collected from the Rio Grande Valley grown under even controlled conditions. Sodium and chloride ion concentrations vary hundreds of percent, depending on the time of collection. Aloe is a succulent plant and takes up minerals from the soil. During rainy seasons the plants are watered by rain, which is low in minerals. However, during dry seasons, the fields are irrigated with water containing a much higher mineral content. Also, fertilizer adds minerals to the soil and can affect the mineral content. The present invention overcame this problem by dialyzing out the salts in excess concentrations, if they occurred, in order to produce a consistent, final product.

A fourth problem—undesired variations in tonicity of products produced from extracted aloe juice—results from the first three problems just described: (1) The *Aloe vera* leaves may have a varying yellow sap concentration that can vary in amount and content, (2) acid content, i.e., maleic acid content, within the leaf varies depending on the time the leaf is exposed to light and darkness after cutting, and (3) the mineral content varies with the rainfall and treatment, i.e. fertilizer. These variables affect all the constituents of the *Aloe vera* gel, such as the Aloe mucilage content. The rate of degradation of the mucilage varies with the acid content, which variation, in turn, causes the size of the mucilage polymers to vary upon processing. All of these variables affect the osmotic pressure of the extracted *Aloe vera* juice. Tonicity determines the degree of moisture transfer of a product to or from skin. Osmotic pressure affects tonicity of Aloe juice (William F. Ganong, REVIEW OF MEDICAL PHYSIOLOGY (Lange Medical Publications, Los Altos, CA) at 16–29, 984 (1983), which can result, in turn, in Aloe products that are isotonic, hypertonic or hypotonic, depending on the nature of the leaves used.

A fifth problem associated with *Aloe vera* is the degradation of the active substance by hydrolysis. This degradation can take place with time in the presence of water which is the form of the stabilized gel.

It is clear that Henry H. Cobble (U.S. Pat. No. 3,892,853) and Billy C. Coats (U.S. Pat. No. 4,178,372) in their state-of-the-art processes for processing aloe leaves with the following common characteristics failed to address the aforementioned problems:

1. They added a catalytic amount of a mild oxidant to fresh Aloe vera gel which is brought from about 35° C. to about 80° C.
   Cobble, col. 2, line 65–68
   Coats, col. 2, line 13–16
2. The preferred or oxidant material used for catalytic oxidation is hydrogen peroxide.
   Cobble, col. 3, line 16–18
   Coats, col. 3, line 43–45
3. Both prefer four to five year old plants.
   Cobble, col. 2, line 31–33
   Coats, col. 2, line 39–40
4. A non-toxic antioxidant is used to arrest catalytic oxidation, such as tocopherol.
   Cobble, col. 10, line 8–9
   Coats, col. 5, line 28–31
5. Their mild oxidation is allowed to take place for a period of time to oxidize completely certain gel substances believed to be beta globulin proteins and perhaps alpha globula proteins.
   Cobble, col. 3, line 41–44
   Coats, col. 3, line 43–47
6. Bill Coats used a commercially available extruder designed for orange juice processing in his process.
   Coats, col. 3, line 5–9
7. Neither the Cobble nor Coats process collects and preserves the yellow sap.
8. If the yellow sap contaminates the product, the disclosed process(es) provide(s) no means of removing it.
9. Laboratory analysis of *Aloe vera* gel prepared by both the Coats and Cobble processes, revealed stabilized *Aloe vera* gel that varied hundreds of percent in yellow sap content, mineral content, color, taste, gel consistency and osmolarity (tonicity).

In general, both the Cobble and Coats *Aloe vera* processes do not provide a means for collecting, storing and preserving the yellow sap separately from the mucilage portion. Therefore, when the mucilage is separated from the leaf, it is more prone to be contaminated with yellow sap. Their process(es) require(s) heat and oxidation which can oxidize desirable fractions of the *Aloe vera* gel, as well as undesirable fractions. Additionally, heat accelerates the degradation of the gel. They cannot adjust for the variable mineral content, nor can they select and separate by size, the *Aloe vera* gel matrix molecule, a substantially acetylated mannan, which affects the moisturizing properties of the gel. Also, the process works best on mature, four to five year old leaves. This is a handicap because a freeze will destroy mature leaves, which has happened in the Rio Grande Valley in three of the last five years. Domestically grown mature leaves are now virtually unattainable in the United States in the present state of the aloe processing industry.

In addition, a problem in the art is that the fraction or chemical substance in *Aloe vera* that is responsible for its uses has never been definitively identified. For example, in a publication by John Fisher published in the *U.S. Pharmacist*, August, 1982, at page 37–45, "In contrast to aloe latex, aloe gel normally does not contain an anthraquinone glycoside except in small amounts. However, a number of substances have been identified in the gel. These substances include mono- and polysaccharides, tannins, steroid compounds, various organic acids and enzymes, saponins, vitamins and minerals such as iron, copper, calcium, magnesium, sodium and potassium. The contribution of these substances to the plant's reputed activity remains unclear". Recently, this has been reported in the Berkeley Medical Newsletter and currently no one has been able to identify any use and associate that with any particular substance in *Aloe vera*. There is a need to know what the active substance is and to isolate that substance so that one can quantitatively administer a prescribed amount of that substance. For example, aspirin can be obtained from willow bark, but one would not know how much willow bark to chew to get a consistent dosage of aspirin, whereas if the aspirin is extracted out of the willow bark, then one can consistently take the same amount and aspirin in that form is stable.

Fractionation of aloe leaves has not been the source of a great number of publication in the art. Purely academic articles not related to utility of using fractionated portions of aloe have been published by the Indian team of Mandal and Das:

(1) Gaurhari Mandal and Amalendu Das, "Structure of the Glucomannan Isolated from the Leaves of *Aloe Barbadensis* Miller", (Elsevier Scientific Publishing Company, Amsterdam, 1980) 87 at 249-256.

(2) Gaurhari Mandal and Amalendu Das, "Structure of the D-Galactan Isolated from *Aloe barbadensis* Miller", (Elsevier Scientific Publishing Company, Amsterdam, 1980) 86 at 247-257.

(3) Gaurhari Mandal, Rina Ghosh and Amalendu Das, "Characterisation of Polysaccharides of *Aloe barbadensis* Miller: Part III—Structure of an Acidic Oligosaccharide", (Indian Journal of Chemistry, September 1983) 22B at 890-893. Item (3) is not admitted to be prior art to the present invention.

SUMMARY OF THE INVENTION

The present invention generally relates to the production of refined aloe products, more particularly to the improved processing of aloe plants by separating the various components of the leaves of the aloe plant, and even more particularly to a process for producing an improved mucilaginous substantially anthraquinone-free extract of the aloe plant which is pH stable, substantially consistent in salt content, and capable of achieving a predetermined level of tonicity.

The present invention is also directed to a second process whereby the active chemical substance in the aloe plant is physically extracted from whole leaves or the improved mucilaginous substantially anthraquinone-free extract. According to this process, the chemical substance is further freeze dried or lyophilized and optionally sterilized by irradiating it with either gamma or microwave radiation. In this form, the chemical substance is substantially non-degradable and can be given in a prescribed amount.

The present invention is also directed to the active chemical substance in the aloe plant in the form produced by the second process described above. The active chemical substance has been found to be substantially non-degradable lyophilized ordered linear polymer of acetylated mannose-monomers. The mannose monomers are preferably bonded together by $\beta(1\rightarrow4)$ bonds. The active chemical substance has been measured, standardized and characterized by analytical chemistry and bioassay techniques.

By "substantially anthraquinone-free" as that term is applied to gel, fillet(s), extract, or the like, I mean less than about 0.05 percent by weight. The mucilaginous substantially anthraquinone-free extract of my invention preferably has less than about 0.001 percent by weight of anthraquinone. By "pH stable" I mean for an extract from a predetermined Aloe fraction grown in a predetermined locale and Aloe species having a reproducible pH within one-half pH unit over a three year period. By the term "substantially free in salt content" I mean that property for an extract (from a like predetermined aloe fraction grown in a predetermined locale and aloe species) a reproducible salt content within ±20 ppm over a three year period. By "predetermined tonicity" I mean that tonicity for an extract from a predetermined aloe fraction having a reproducible osmotic pressure of ±20 mOsm over a three year period. By "active chemical substance" I mean that substance which is responsible for the wound healing and other beneficial properties of *Aloe vera*. By "substantially non-degradable" I mean a product which decreases in molecular weight by less than 5 percent over a period of two years and a product which maintains more than 95 percent of its biological activity over a period of two years. By "substantially acetylated mannan" I mean partially or substantially completely acetylated mannose monomers.

For example, for a topical product, it is desired to have a pH stable product that matches the natural acid mantle of the skin (pH from about 4 to about 6). For broken skin, the pH should more closely resemble serum or plasma (pH about 7.4). This level is adjusted for each skin care product based upon intended use. Total salt content should be such to produce an osmotic pressure between about 100 or about 500 milliosmoles (mOsm). Oily skin, for example, needs isotonic to hypertonic solutions (280-500 mOsm); normal skin from 180-380 mOsm; dry skin from 100-280 mOsm.

More particularly, the process of my invention is one for "that property extracting substantially anthraquinone-free" aloe gel from a leaf of the aloe plant, which process comprises the following steps:

(a) washing an aloe leaf in a bacteriacidal solution to remove substantially all surface dirt and bacteria;

(b) removing at least a first end portion from said washed leaf;

(c) draining and collecting anthraquinone rich sap from said cut and washed leaf; and (d) removing rind from said leaf to produce a substantially anthraquinone-free gel.

Removal of "substantially all surface dirt and bacteria" means (1) removal of dirt to the extent that remaining dirt is less than 0.1% by weight of the weight of the leaf and (2) killing such surface bacteria that the remaining surface bacteria are less than 100 count per gram of leaves.

One skilled in the art will appreciate that instead of steps (b), (c) and (d), one may instead (b) crush the washed aloe leaves and (c) dialyze the crushed leaves chemically removing unwanted fractions, i.e., anthraquinones, minerals and acids and the rind to produce a substantially anthraquinone-free gel. More preferably, aloe leaves or whole plants may be collected from the field sufficiently clean to eliminate a washing step; the juice is extracted by crushing, squeezing and/or extrusion, and the desired aloe fraction components, e.g. free of anthraquinones, extracted from the whole juice using dialysis or ultrafiltration as described herein. The juice fractions can be separated into individual components and subsequently remixed in any desired combination, an optionally stabilized as described herein.

Preferably, my process for producing substantially anthraquinone-free juice from the leaf of an aloe plant comprises the following steps:

(a) washing an aloe leaf in a bacteriacidal solution to remove substantially all surface dirt and bacteria;

(b) removing a first end portion and a second portion from said washed leaf;

(c) draining and collecting anthraquinone rich sap from said washed and cut leaf;

(d) removing rind from said leaf to produce a substantially anthraquinone-free aloe gel fillet; and (e) grinding and homogenizing said substantially anthraquinone-free aloe gel fillet to produce substantially anthraquinone-free juice.

Furthermore, my preferred process may further comprise the step of ultrafiltration in order to osmotically adjust the aloe juice or aloe vera fraction, or to reduce even further the levels of anthraquinones to less than 5 ppm, even down to less than 100 parts per billion by weight.

These steps enable the processor to use large or small leaves (even less than one year old) because the polymer size found in the mature leaves can be selected and processed out of smaller, immature leaves.

One of the advantages of the instant process is that damaged leaves previously considered unusable due to strong winds or poor collection techniques can be processed, and the undesirable contaminants can be dialyzed out.

Most preferably, my process envisions further filtering the aloe juice to remove fibrous material. In such form, the aloe juice may be incorporated in an abundant number of different products for internal or external use.

The process of my invention may further comprise, as a preferred embodiment, the addition of one or more members selected from the group consisting of preservatives, flavorants, or any FDA additives (generally recognized as safe, or "GRAS" additives) to said aloe gel fillet or said aloe juice or said Aloe vera fraction. Most preferably, the preservative is selected from the group consisting of benzoic acid, potassium sorbate, methylparaben and propylparaben or any other FDA approved additive for topical or internal uses.

The juice of my invention, optionally, may be irradiated, freeze dried, sonic sterilized or pasteurized, whereby said juice is preserved.

The ultrafiltration (dialysis) step incorporates membrane technology that allows the selection of filters with different pore sizes, depending on the condition of the cut aloe leaves, that can accomplish any combination of the following:

(1) A small pore size filter (preferably about 100 Daltons) that separates out water and salts from the *Aloe vera* gel, if needed.

(2) Larger pore size filters (preferably about 500 Daltons) that can separate out the acids from the *Aloe vera* gel, if needed.

(3) Even larger pore size filters (preferably about 2,000 Daltons) that can separate the yellow sap components from the *Aloe vera* gel, if needed.

(4) And even larger pore size filters (preferably from about 10,000–100,000 Daltons that can size the gel matrix polymers, and divide them out by molecular weight.

A Romicon TM 4-column (Romicon Co., 100 Cummings Park Woburn, MA 01801, Model No. HF4 SSS, Membrane Type PM50, Membrane Nos. H526.5-43-pm50) as an ultrafiltration device is recommended.

As an additional preferred embodiment, the washing step of the process may comprise washing the substantially anthraquinone-free aloe gel fillet in a tumbler washer prior to grinding said fillet.

An effective dermal wound gel may be produced by the process of my invention, and may preferably comprise 0.1 to 100 weight percent substantially anthraquinone-free aloe juice, 0 to 2 weight percent allantoin, 0 to 6 weight percent panthenol, and excipients or carriers. See Example 7. Levels of allantoin and/or panthenol are controlled by the FDA. See Zimmerman, THE ESSENTIAL GUIDE TO NONPRESCRIPTION DRUGS (Harper and Row, New York, 1983).

A second process of my invention is one for extracting the active chemical substance in the aloe plant from a leaf of the aloe plant, which process comprises the following steps:

(a) washing an aloe leaf in a bacteriacidal solution to remove substantially all surface dirt and bacteria;

(b) removing at least a first end portion from said washed leaf;

(c) draining, preserving and collecting anthraquinone rich sap from said cut and washed leaf;

(d) removing ring from said leaf to produce a substantially anthraquinone-free aloe gel fillet;

(e) grinding and homogenizing said substantially anthraquinone-free aloe gel fillet to produce substantially anthraquinone-free aloe juice having solubilized matter;

(f) adding a water soluble, lower aliphatic polar solvent to the aloe juice to precipitate the active chemical substance and thereby to form a heterogeneous solution;

(g) removing the water soluble, lower aliphatic polar solvent and the solubilized matter from the heterogeneous solution to isolate the precipitated active chemical substance; and (h) drying the precipitated active chemical substance.

One skilled in the art will appreciate that instead of steps (b), (c) and (d), one may instead (b) crush the washed aloe leaves and (c) dialyze the crushed leaves chemically removing unwanted fractions, i.e., anthraquinones, minerals and acids and the rind to produce a substantially anthraquinone-free gel that may then be subjected to steps (e), (f), (g) and (h) to extract the active chemical substance.

One skilled in the art will appreciate that one may simply obtain aloe juice having solubilized matter from aloe leaves and then subject this juice to steps (f), (g) and (h) to extract the active chemical substance.

Indeed, one skilled in the art will also appreciate that instead of steps (b), (c), (d) and (e), one may instead crush the washed aloe leaves and extrude anthraquinone-rich aloe juice having solubilized matter and then subject the aloe juice to steps (f), (g) and (h) to extract the active chemical substance. The active chemical substance is effectively separated from anthraquinones and deleterious ions by this process since all the anthraquinones and all the ions are water soluble and remain in the liquid solvent phase and do not precipitate.

One skilled in the art will also appreciate that instead of steps (b), (c), (d) and (e) one may instead grind the whole washed aloe leaves, filter out fibrous material, and homogenize the remainder to produce anthraquinone-rich aloe juice having solubilized matter. The aloe juice can then be subjected to steps (f), (g) and (h) to extract the active chemical substance. The active chemical substance is effectively separated from anthraquinones and deleterious ions by this process for the reasons noted above.

One skilled in the art will appreciate that an additional process for extracting the active chemical substance in the aloe plant from a leaf of the aloe plant comprises the following steps:

(a) washing an aloe leaf in a bacteriacidal solution to remove substantially all surface dirt and bacteria;

(b) removing rind from said leaf to produce an aloe gel fillet;

(c) grinding and homogenizing said aloe gel fillet to produce aloe juice having solubilized matter;

(d) adding a water soluble, lower aliphatic polar solvent to the aloe juice to precipitate the active chemical substance and thereby to form a heterogeneous solution;

(e) removing the water soluble, lower aliphatic solvent and the solubilized matter from the heterogeneous solution to isolate the precipitated active chemical substance; and (f) drying the precipitated active chemical substance.

As noted above, the active chemical substance is effectively separated from anthraquinones and deleterious ions by this process since all the anthraquinones and all the ions are water soluble and remain in the liquid solvent phase and do not precipitate.

Removal of "substantially all surface dirt and bacteria" means (1) removal of dirt to the extent that remaining dirt is less than 0.1% by weight of the weight of the leaf and (2) killing such surface bacteria that the remaining surface bacteria are less than 100 count per gram of leaves.

Preferably, in all the above processes for extracting the active chemical substance in the aloe plant from a leaf of the aloe plant, four volumes of the water soluble, lower aliphatic polar solvent are added to one volume of aloe juice to precipitate the active chemical substance. Preferred water soluble, lower aliphatic polar solvents are methanol, ethanol and propanol. The most preferred solvent is ethanol. One skilled in the art will recognize that other water soluble, lower aliphatic polar solvents may be substituted for the preferred solvents as long as the active chemical substance will precipitate therefrom.

It is preferred in the above extraction processes that the active chemical substance is allowed to precipitate from the water soluble, lower aliphatic polar solvent and aloe juice mixture for about four hours. It has been determined that allowing the mixture to precipitate for four hours gives the optimum yield of active chemical substance and that after four hours, the precipitated active chemical substance begins to degrade. It has also been determined, however, that significant amounts of active chemical substance have been recovered after a precipitation period of 24 hours. One skilled in the art will appreciate that the optimum precipitation time period is dependant on ambient temperature and pressure, as well as the nature of the water soluble, lower aliphatic polar solvent.

It is also preferred in the above extraction processes that the precipitated active chemical substance be dried by lyophilization rather than be oven drying since heat may aid in the hydrolysis or degradation of the active chemical substance.

In all of the above extraction processes, any fibrous material (cellulose) contained in the aloe juice is also precipitated by the water soluble, lower aliphatic polar solvent but is precipitated early with the addition of the solvent and is less dense than the active chemical substance. The fibrous material remains on the surface of the solvent after the active chemical substance has been allowed to settle and can therefore be removed quite easily. One skilled in the art will appreciate that one may instead filter the aloe juice to remove fibrous material prior to the addition of solvent.

More preferably, in all of the above processes, aloe leaves or whole plants may be collected from the field sufficiently clean to eliminate a washing step.

The dried, precipitated active ingredients, optionally, may be irradiated by gamma or microwave radiation whereby said active chemical substance is sterilized and preserved.

Accordingly, the present invention provides new and improved methods for the production of *Aloe vera* products.

The present invention furthermore provides improved methods for processing the leaf of the *Aloe vera* plant in a manner which avoids the undesirable combination or mixture of distinctively characteristic portions of such plant leaf.

The present invention moreover provides improved processes for preparing various extracts of the leaf of the *Aloe vera* plant which minimizes the concentrations of undesirable components in the finished extracts.

The present invention also provides new and improved processes for preparing extracts of the leaf of the *Aloe vera* plant which maximize the concentration of certain components characteristic of particular portions or segments of the leaf while minimizing or eliminating certain components characteristic of other portions or segments of the leaf.

The present invention also provides new and improved processes for preparing extracts from the leaf of the *Aloe vera* plant which are low in concentration of yellow sap of the leaf.

My preferred processes have these advantages over the prior art:

1. No catalytic amount of a mild oxidant is used, thus preventing the oxidation of desirable constituents.

2. The processes do not require heat, but can be performed at room temperature.

3. Young, immature or damaged leaves can be used.

4. An antioxidant does not have to be used to arrest catalytic oxidation.

5. The beta gobulins and alpha globulins can be dialyzed out.

6. Both hand and mechanical extruders can be used.

7. The processes allow for the separate collection, storage and preservation of the yellow sap. (The yellow sap has been banned as a laxative, but it can be used as a sunscreen on undamaged skin. Plus, it provides a tan color to the skin.)

8. If the yellow sap gets into the *Aloe vera* gel, it can be removed.

9. It can provide *Aloe vera* gel that is standardized in its yellow sap content, mineral content, color, taste, gel consistency and osmolarity (tonicity).

10. Individual components of *Aloe vera* gel can be isolated, dialyzed out and concentrated to concentrations many times greater than are found in the natural juice.

11. Also, by separating out the fractions, new combinations of *Aloe vera* gel components are now attainable that heretofore did not exist in nature.

12. In the event that too much preservative, flavoring or other GRAS substance is overadded, the batch can be saved in most cases by dialyzing out the excess.

13. Selected Aloe components can be dialyzed out, chemically altered and then added back.

Enzymes can be added to the Aloe gel, allowed to react and then separated out by ultrafiltration.

The present invention finally provides a method for extracting the active chemical substance in *Aloe vera* gel. This active chemical substance shall hereinafter be referred to as CARRISYN® extract. As mentioned above, CARRISYN® extract has been found to be a substantially non-degradable lyophilized ordered linear polymer of acetylated mannose monomers which is measured and standardized both using analytical chemistry and bioassay techniques.

DESCRIPTION OF THE FIGURES

FIG. 13 reveals absorbance data for one CARRISYN® batch which had been exhaustively dialyzed for 60 hours.

FIG. 14 shows an infrared spectrum for raw aloe gel that was cast into a film.

FIG. 15 shows an infrared spectrum for a sample of CARRISYN® extract.

DETAILED DESCRIPTION OF ADDITIONAL PREFERRED EMBODIMENTS

Figure 1:
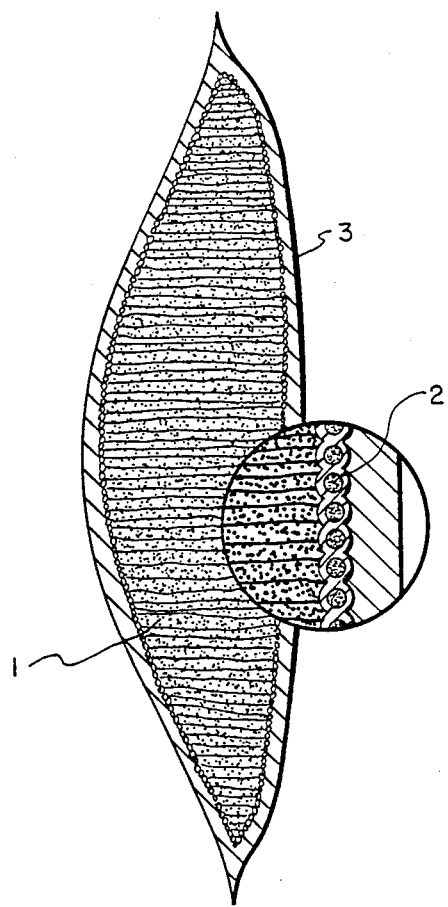
FIGS. 1 and 2 show cut-away portions of an aloe vera leaf.
Figure 2:
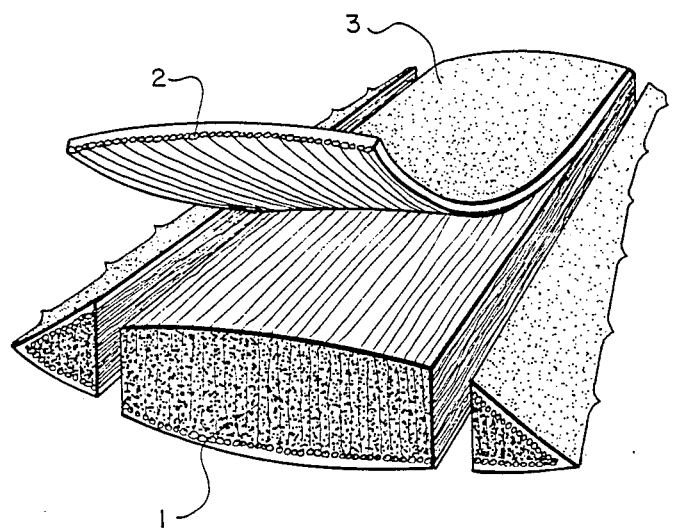
Figure 3B:
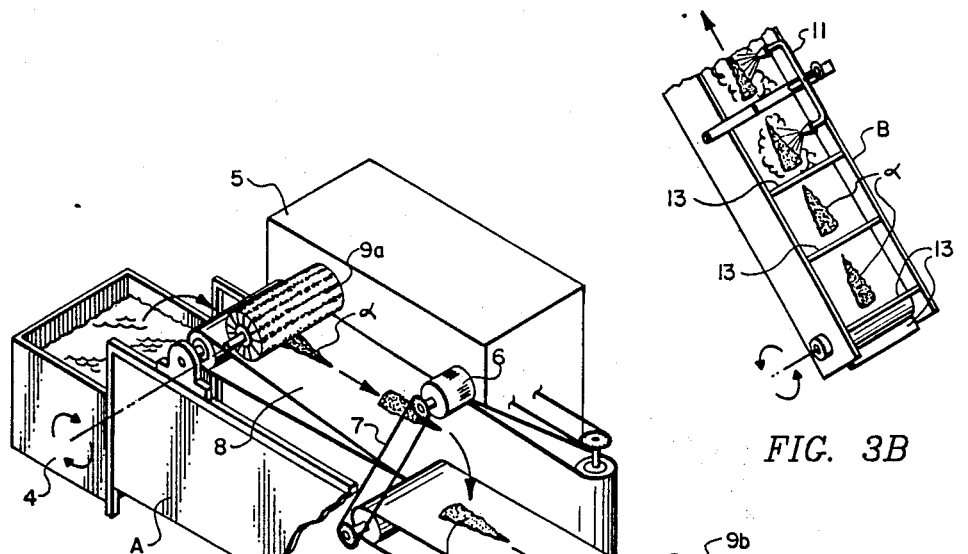
FIG. 3 shows a schematic of a preferred leaf washing apparatus used in my process.
Figure 3A:
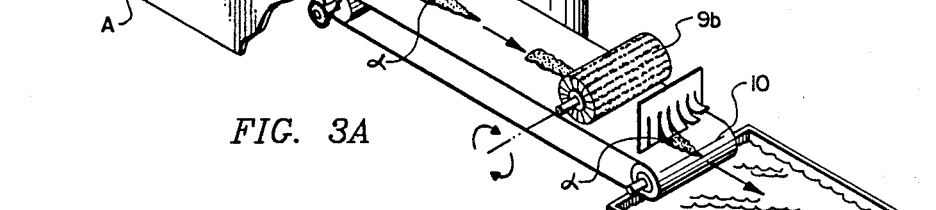

In accordance with these and other objects, the process of the present invention arises out of the discovery and recognition that particular distinct portions of the *Aloe vera* leaf, specifically the yellow sap, internal gel matrix, and outer rind, exhibit characteristics respectively unique to those portions; and that the characteristics of one distinct portion may be conducive to its use for a particular application or end use product with the characteristics of another distinct portion being inconsistent with, or detrimental to, such use. For example, it has been determined that an extract derived from the internal gel matrix has characteristics which make it extremely desirable in the production of cosmetic or skin care products; but the yellow sap has characteristics which are particularly detrimental for such use.

Furthermore, I have discovered and recognized that subportions of the yellow sap and internal gel matrix have characteristics which are even unique to those sub-portions, the extracts therefrom therefore having potentially distinct uses from one another. A summary of these distinct portions, and some of their characteristics and potential uses as I have found, is

| PORTION | SUB-PORTION | UTILITIES |
|---|---|---|
| Yellow Sap | (1) Sediment | laxative, antifungal, antibiological, pesticidal and sunscreen |
| | (2) Supernatant | mucosal protective action, sunscreen |
| Internal Gel Matrix | (1) Mucilage | penetrant, hypoallergenic, moisturizer |
| | (2) Gel Fillets | ulceroprotective, cell stimulative moisturizer, wound healing |
| | (3) Interstitial Fibers | natural preservative, hemostat |
| | (4) Residual Matrix | cell growth stimulant |
| Outer Rind | | pesticidal insect repellent, paper pulp fiber |

Based upon the aforementioned knowledge and recognition, and in order to optimize the quality and concentration of the desired components in the final extract depending upon the intended use thereof, the process of this invention is directed to the initial fractionating of the leaves of the *Aloe vera* plant into the particular distinct portions and sub-portions defined above, as well as the separation and isolation of particular components of such sub-portions defined above. The specific details and features of such processes will become more readily understood and appreciated from the following detailed description. The present invention is also directed to particular components that are isolated by the above-mentioned processes.

FRACTIONATION PROCESS

The extracts produced by the process of the present invention are preferably obtained from the outer, lower leaves of mature, outdoor grown *Aloe vera* plants. A two year old plant is normally mature; however, the broader leaves of a four or five year old plant typically contain larger amounts of the desired extracts and are also easier to handle. Four or five year old leaves of *Aloe barbadensis* Miller grown in the Rio Grande Valley of Texas are most preferable. These leaves generally weigh about 1½–2½ pounds each. Depending upon the particular use or products that are desired, the leaves can be processed immediately after cutting them from the plant or they can be stored under appropriate conditions for varying time periods before they are processed. Additionally, concentration of various components of the leaf are affected by seasonal variations and the environmental conditions to which the leaves are subjected, all of which should be taken into consideration depending upon the specific intended use to which the plant extracts are to be directed.

The leaves should be pulled or cut from near the base of the plant, preferably without breaking or damaging any part of the leaf prior to processing. One preferably employs a small knife of less than 6 inches, e.g., a pocket knife and cuts the leaf at the base immediately above the stalk, and peels the leaf from the stalk, in order to prevent leakage of the clear cellular gel or contamination of the gel with the yellow sap. Any breakage or bruising of the leaf can result in the undesirable commingling of the distinct portions, and therefore, component characteristics of the leaf.

After removal from the plant, the leaves are normally cleaned by washing them with a mild scrubbing action or spraying with a suitable detergent solution (e.g., we prefer OLYMPIC POOL CHLOR 65 TM, distributed by York Chem Co., Dallas, Texas). In some instances, the cleaning takes place with the aid of soft brushes. After cleaning, the leaves are rinsed thoroughly in clean water to remove any vestige of any detergent solution.

The bottom white or light colored portion of each leaf and the tipmost portion thereof are removed by cutting carefully with a small sharp knife. These portions, essentially constituting the ends of the leaf, may be separately processed to obtain the yellow sap therefrom for those applications in which it is desired to produce products having components with the yellow sap characteristics referred to above.

The remaining portion of each *Aloe vera* leaf is then crosscut into short segments, preferably one-half inch in length, and each segment is placed upright in an aqueous solution (preferably deionized water) which may be hypertonic, isotonic or hypotonic, resulting in the yellow sap draining from the segments. Alternatively, in those applications in which it is desired to collect the yellow sap for use in other preparations having the characteristics noted above, the segments may be placed upright in a dry collection container, preferably of stainless steel with a stainless steel wire mesh bottom to allow drainage and for water contact to allow the water to dialyze the leaves.

The segments are permitted to drain for approximately twenty to thirty minutes in this manner. The cut segments will eventually form a seal and cease draining. The yellow sap that is collected will then, upon standing for an appropriate period of time, separate into two sub-portions, namely sediment and supernatant, respectively. The yellow sap is useful for making a good sunscreen on intact skin (*not* broken skin) and provides the skin with an oil tan color, and is also useful for the manufacture of laxatives.

After completion of the procedures which remove the yellow sap from the cut leaf segments, the segments are then pared to form fillets utilizing any suitable equipment such as a wire (i.e., consumer cheese) slicer or paring blades (e.g., paring knife) to remove the outer ring or skin of the leaf segments and the layer that is immediately below such outer skin. The leaf segments may be frozen to facilitate this skinning procedure. After paring, what remains is the internal gel matrix portion (fillet), and this portion is inspected and hand cleaned to remove any adhering skin or discolored portions to eliminate any residual yellow sap therefrom. One uses a mild water spray, preferably deionized water (and free of alcohol) or submerges the gel matrix portion under flowing clean water, to facilitate removal of such yellow sap residuum.

The resultant fillet (internal gel matrix) can then be drained for approximately an hour. During this draining procedure, a slimy coating usually forms on the surfaces of the gel matrix, this coating being collected by gravity or assisted by appropriate means such as centrifugation. This collected coating is the mucilage sub-portion referred to above.

The remainder of the gel matrix, in the form of gel matrix strips, may then be ground, shredded or blended to break up the interstitial fibers present therein, or the gel matrix strips may be forced through a wire mesh or filter screen in order to achieve liquefaction. This resultant substance may then be subsequently homogenized. Alternatively, the gel matrix strips may be frozen and thawed and subsequently mixed to produce a liquid substance with fibers (such substance constituting the gel fillets sub-portion referred to above). This substance can then be filtered to obtain the interstitial fibers sub-portion, leaving the residual matrix sub-portion referred to above. In short, for topical applications the interstitial fibers are removed from the internal gel matrix portions (fillets), while for internal applications the fibers are maintained with the balance of the fillet contents. For topical or internal use, the appropriate gel fractions are homogenized, e.g., by a dairy milk homogenizer (prior to addition of stabilizers, preservatives, excipients, color or other GRAS additives) in order to make the gel fractions more accessible to further processing, e.g., to reduce growth of bacteria. At this point in the process, the resulting extract may be tested utilizing known quality control procedures such as mass spectroscopy, gas chromatography, high pressure liquid chromatography, or other analytical techniques.

The homogenized extract thus obtained typically has a pH of approximately about 4 to about 5, preferably about 4. To increase its stability, the homogenized extract is typically normalized by the addition of citric acid, boric acid, ascorbic acid, or other suitable materials depending on end use (e.g., for internal consumption, citric acid and/or ascorbic acid is employed; for eye applications boric acid is used). Finally, the homogenized extract may be sterilized, utilizing any method well known in the art such as irradiation, sonic sterilization, controlled heating or by the addition of antibacterial or bacteriostatic chemicals such as GRAS—cetyl alcohol, sodium benzoate or ethyl alcohol, in amounts and concentrations well known in the art. It will be appreciated that various combinations of the foregoing may also be utilized to sterilize the extract produced in accordance with this invention. It will also be appreciated that various industry acceptable stabilizers and additives may be added to the homogenized gel extracts if desired.

Final quality control procedures may be utilized at this point and the extract is then ready for bottling or compounding with other materials. The extract from the internal gel matrix, when prepared as described herein, will contain a very low concentration of yellow sap and is most suitable for skin care and cosmetic applications.

All steps in the process described are performed at about room temperature.

Various modifications of the disclosed process and compositions of the invention, as well as alternative modifications, variations and equivalents will become apparent to persons skilled in the art upon reading the above general description. The following examples are illustrative only and are not intended to limit the scope of the appended claims, which cover any such modifications, equivalents or variations.

EXAMPLE 1

Process for preparing stabilized aloe gel fillets, and homogenization.

A. PRELIMINARY WORK

1. Previously cleaned tanks, mixers and fittings were sanitized with 50% isopropyl alcohol (IPA) solution and rinsed free of IPA with hot D.I. Water.

2. Pumps and attached hoses were drained with 5% "HTH" chlorine swimming pool solutions, then flushed with water.

3. The pumps and attached hoses were sanitized with 50% isopropyl alcohol solution. Pumps and attached hoses were flushed with hot deionized water until free of IPA.

4. An homogenizer and attached hoses and pumps were sanitized with 50% isopropyl alcohol solution. The homogenizer and attached hoses were flushed with hot deionized water until free of IPA.

*Aloe barbadensis* Miller leaves collected from the Rio Grande Valley were transferred in a refrigerated truck at 40° to 45° F. within eight hours after harvest and stored under refrigeration at 40° to 45° F. until processed to reduce degradation.

Twenty to sixty pounds of stored leaves were then placed in a prewash bath of an aqueous solution of calcium hypochlorite at room temperature, substantially to remove surface dirt from the leaves and kill surface bacteria on the leaves. The aqueous solution of calcium hypochlorite was prepared by adding approximately 0.125 grams of 98% calcium hypochlorite to one liter of water to produce a solution containing 50 ppm of free chlorine. The leaves remained in the prewash bath for a period of approximately five minutes.

Next, the substantially dirt and bacteria free leaves were placed on the horizontal conveyor belt of a "Thompson Aloe Washer" made by Thompson Manufacturing Company, Harlingen, Texas. The "Thompson Aloe Washer" washed the leaves with room temperature water to remove the surface dirt and aqueous solution of calcium hypochlorite from the leaves. Again, the leaves were visually inspected and hand scrubbed as necessary to remove any surface dirt remaining on the leaves. Such leaves were then rinsed with room temperature water.

The tip and butt portion was then removed from each leaf and the leaves were placed in stainless steel basket-type containers, placed together on top of a funnel shaped stainless steel collector, each container having a mesh bottom. Yellow sap was allowed to drain from the leaves for approximately 30 minutes. The yellow sap passed through the mesh bottom of the stainless steel basket and was collected in a funnel shaped collector.

The stainless steel basket type containers containing the aloe leaves were removed from the collector, and were then submerged in a second stainless steel vessel comprising a room temperature water bath of continuously horizontally flowing rinse water moving countercurrent to the containers which are slowly moved by hand from one end of the vessel to the other, for approximately thirty minutes to one hour. This allows the yellow sap to drain further from the leaves. The leaves must be allowed to soak in this solution for 30 minutes.

The leaves were then removed from this solution and the rind was removed from each leaf with a sharp knife or wire cheese slicer to produce an aloe gel fillet from each leaf portion. The aloe gel fillets were visually inspected and any contaminated aloe gel fillets or fillet parts detected by a characteristic yellowish discoloration were discarded. The total mass of uncontaminated aloe gel fillets was 20 to 60 percent of the starting leaf mass, depending on the leaf size and condition.

The uncontaminated aloe gel fillets were then placed in a 750 seat restaurant set stainless steel garbage disposal unit which coarse ground the fillets to an average particle size of the consistency of a thick, but freely flowing (coarse homogenized) liquid. The stainless steel garbage unit was made by the N-sink-erator Division of Emerson Electric Co., Racine, WI, Model No. SS-150-13, Serial No. 115132.

The coarse ground aloe gel fillets then passed to a stainless steel holding vat. The holding vat was made by Process Equipment Corp. of Belding, Michigan, Model No. 100 gallon OVC, Serial No. 40865-3. In this holding vat the coarse ground aloe gel fillets were mixed with a GRAS preservative such as sodium benzoate, potassium sorbate, methylparaben or propylparaben, depending on use and ratio of final product oil to aloe fraction. For topical use a mixture of methyl and propylparaben is recommended; for internal use a mixture of sodium benzoate and potassium benzoate is recommended. For example, if one has a topical application using 10% oil, 90% Aloe fraction, the ratio of propylparaben to methylparaben is 1:9. The weight concentration ratio of the coarse ground aloe gel fillets to the preservative was approximately 1000:1, approximately the upper limits of the FDA guidelines for food and cosmetic preservatives. The preservative solution in the holding vat was initially prepared by adding approved quantities of the GRAS preservative to 10 gallons of deionized water.

From the holding vat, the coarse ground aloe gel fillet-preservative solution was pumped to a homogenizer. The homogenizer was made by Crepaco Food Equipment and Refrigeration, Inc., of Chicago, Illinois, Serial No. 04-03. The homogenizer was of a type typically used in dairy processes for the homogenization of milk. The coarse ground aloe gel fillet-preservative solution was finely homogenized under a pressure of 200 to 10,000 psi.

From the homogenizer the finely homogenized aloe gel fillet-preservative solution was pumped to a stainless steel storage tank. The storage tank was made by Process Equipment Corp. of Belding, Michigan, Model No. 1000 gallon OVC, Serial No. 40866-2. The total mass of the homogenized aloe gel fillet-preservative solution was 20 to 60 percent of the starting leaf mass. Then, if necessary, the homogenized product was dialyzed using ultrafiltration.

FIGS. 3-7 disclose, in even further detail, preferred embodiments of the instant process. Specifically, in FIG. 3, there is disclosed apparatus for leaf washing. *Aloe vera* leaf washing equipment (Thompson Manufacturing Company, Harlington, Texas) A is utilized whereby leaves are first presoaked in vat 4. The whole leaves α are then placed by hand onto a conveyor belt 8 by which they are pulled underneath two brushes 9a and 9b. Conveyor belt 8 is driven via a chain 7 which is rotated on a second end by motor and pulley 6 which extends from a housing 5, also provided by Thompson Manufacturing Company. As the leaves are brushed and washed, upon passing through the second brush 9b, the leaves are inspected at the end 10 of conveyor belt 8, by which the leaves are visually inspected and determined whether or not they are sufficiently clean. If the leaves are not sufficiently clean, they are placed into vat 12 for further washing; if the leaves are sufficiently clean, they are placed upon an upwardly moving conveyor B having steps 13 for which each individual leaf may be further washed with tap water by sprayers 11. The conveyor B is provided by Dallas Mill Wright Co. of Seagoville, Texas. The rinse sprayers 11 are provided by Key Plumbing, Seagoville, Texas. Stainless steel vat 12 is made of 316 stainless steel and is custom made by the National Sheet Metal Company of Dallas, Texas.

Figure 4:
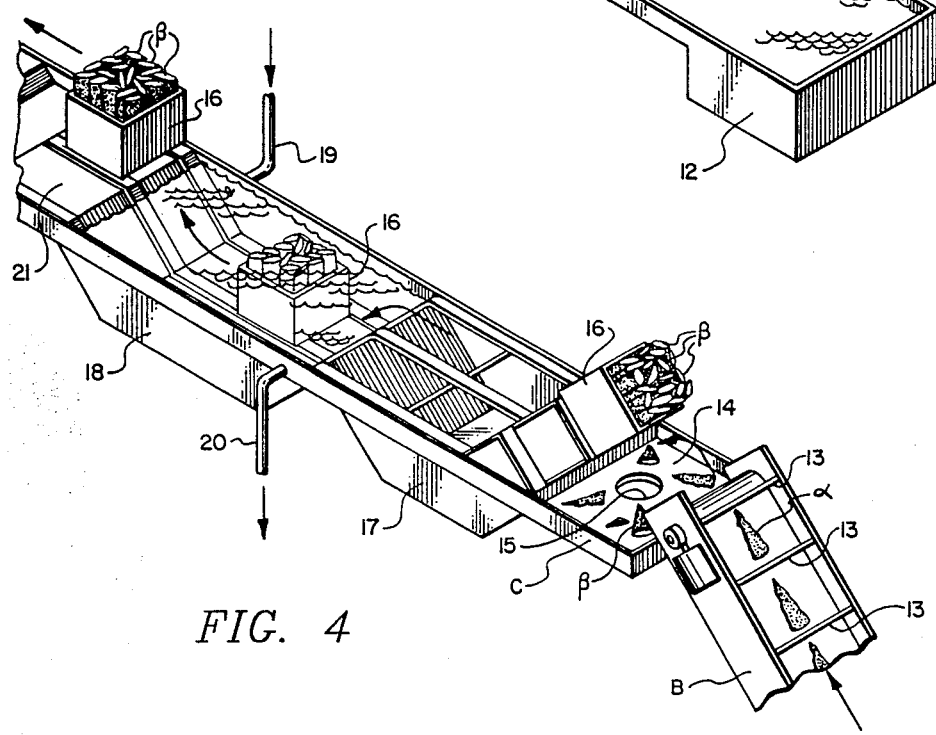
FIG. 4 shows a schematic of a preferred apparatus for sectioning and soaking of *Aloe vera* leaves.

After washing, as indicated in FIG. 4, the leaves are sectioned and soaked. After moving up through steps 13 of conveyor B, the clean, raw leaves α drop onto a tray 14 which is provided with a hole 15 for removal of trash. Tray 14 is part of a sectioning and soaking apparatus C of 316 stainless steel provided by the National Sheet Metal Company of Dallas, Texas. This equipment is custom fabricated. On tray 14 the leaves are manually sectioned at both ends with the tips and butts disposed through the hole 15 into a trash receptacle (not shown). The cut leaves β are then stacked into any one of a number of baskets 16 of stainless steel each having a wire mesh bottom made of stainless steel. Then these baskets 16 are placed in a stainless steel track which forms the top part of a trapezoidal funnel 17 by which yellow sap is drained from the bottom of the leaves through the baskets, falling into the bottom portion of the funnel 17. The yellow sap is periodically removed and is kept frozen for storage. The yellow sap draining step takes about 30 minutes.

After this step, the cut leaves β, still retained in basket 16, are manually moved to water bath 18 at positions closest to trapezoidal funnel 17. In countercurrent flow, water comes into bath 18 through inlet water pipe 19, at a point farthest removed from trapezoidal funnel 17 and is subsequently removed through exit water pipe 20 at a position closest to trapezoidal funnel 17. Trays are gradually moved manually through the water bath in a direction away from trapezoidal funnel 17, and the washing step whereby the baskets remain in water bath 18 takes approximately one hour.

After washing, the baskets are placed on tray 21 for drying, which lasts for only a few minutes. Again, the entire assembly in FIG. 4, pertaining to the baskets, including wire mesh, yellow sap draining and auto washing equipment, is made of 316 stainless steel, custom fabricated by the National Sheet Metal Company, Dallas, Texas.

Figure 5:
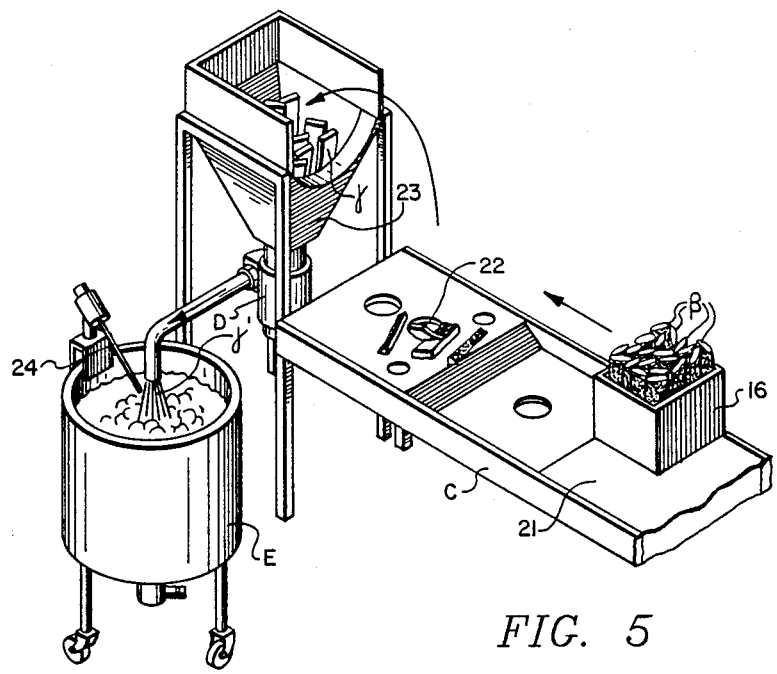
FIG. 5 shows a schematic of preferred apparatus for the cutting of aloe sections into fillets and for coarse grinding.

After washing, the cut leaves β stacked in basket 16 on tray 21 are then removed to an area for further sectioning into fillets, as shown in FIG. 5. Rind 22 is removed from the fillets so that only substantially clear material remains. The rest of the rind 22 is discarded. Fillets γ are then placed into trough 23 which feeds to a rough coarse grinder D. The trough 23 is manufactured of 316 stainless steel by the National Sheet Metal Company of Dallas, Texas. The grinder is a Model No. 5150-N-Sink-erator (Watson Food Service Industries, Inc., Dallas, Texas). After rough coarse grinding through grinder D, the processed material γ' emerging from the grinder passes through to a portable tank E approximately 100 gallon capacity which comprises a vertical single shell tank of 316 stainless steel (Perma-San, Manufacture, distributed through Van Tone, Inc., Dallas, Texas). Coarse ground fillet γ' is agitated in tank E by a Perma-San agitator (Model No. AAPH2) also distributed through Van Tone, Inc. of Dallas, Texas.

Figure 6:
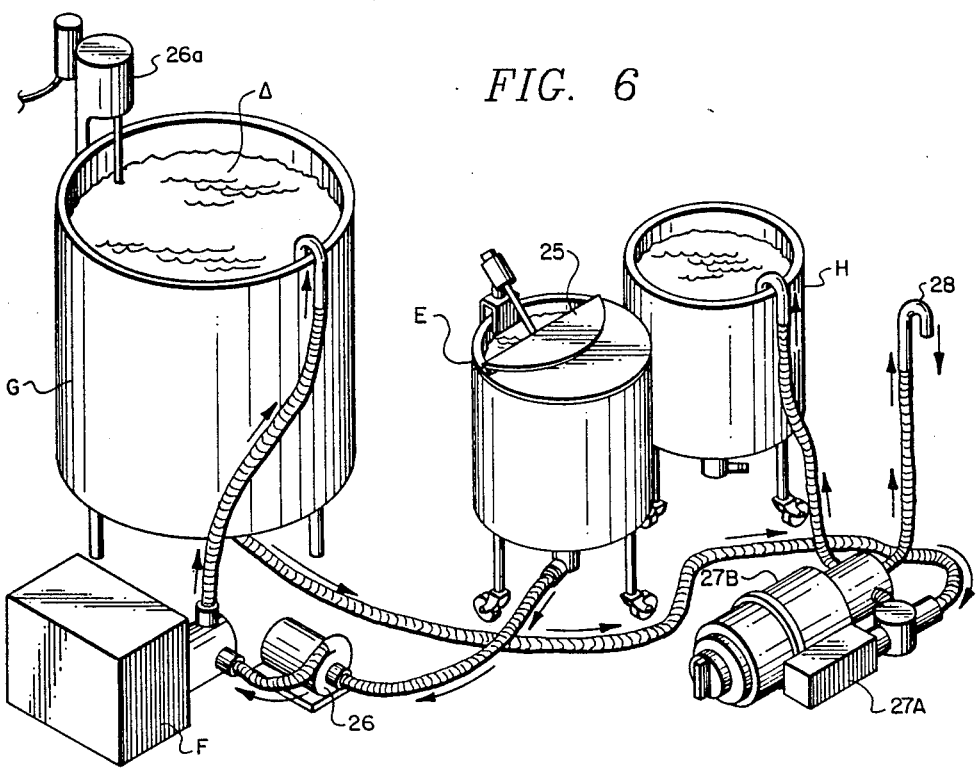
FIG. 6 shows a schematic of preferred apparatus for fine homogenization and (optional) filtering.

After rough homogenization, material from tank E is taken to a separate staged area for fine homogenization and (optional) filtering. In FIG. 6, material from tank E is pumped through pump 26 (centrifuge pump provided by Crepaco, Inc., Dallas, Texas, Model No. 4V-81, of stainless steel) driven by Reliance Motor Model No. B76Q2139M-VF of the Reliance Electric Company, Cleveland, Ohio into a fine homogenizer F (Crepaco, Inc., Dallas, Texas, Model No. 3DD13). After fine homogenization, the material is transported to a large 1,000 gallon vertical single shell mixing tank G made of 316 stainless steel (Perma-San, Manufacturer, distributed to Van Tone, Inc. of Dallas, Texas). The finely ground fillet Δ is agitated by a Perma-San agitator 26a (Perma-San, Model No. AAPH2, distributed through Van Tone, Inc., Dallas, Texas). Material Δ in tank G may be sent directly to processing for a drinking product for direct human consumption after flavoring and appropriate preservatives are added. In the alternative, material in tank G may be removed and sent to pump 27a which forms one unit with filter 27b for removal of pulp through discard line 28. Pump 27a and filter 27b form the part of a Lomart diatomite filter (Model No. 99-2138 distributed by Allen Recreation Company, Dallas, Texas). Filtered material is then pumped into tank H, which like tank E, can be provided with a lid 25.

Figure 7:
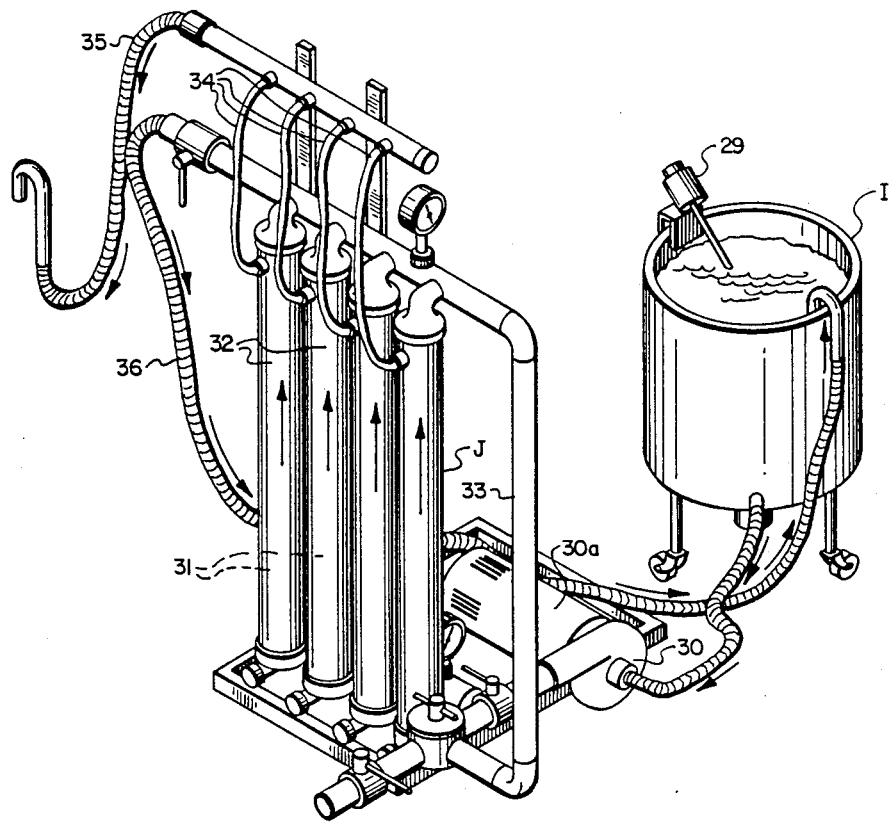
FIG. 7 shows a schematic of a preferred use of dialysis equipment for fine separations of processed aloe material.
Figure 8:
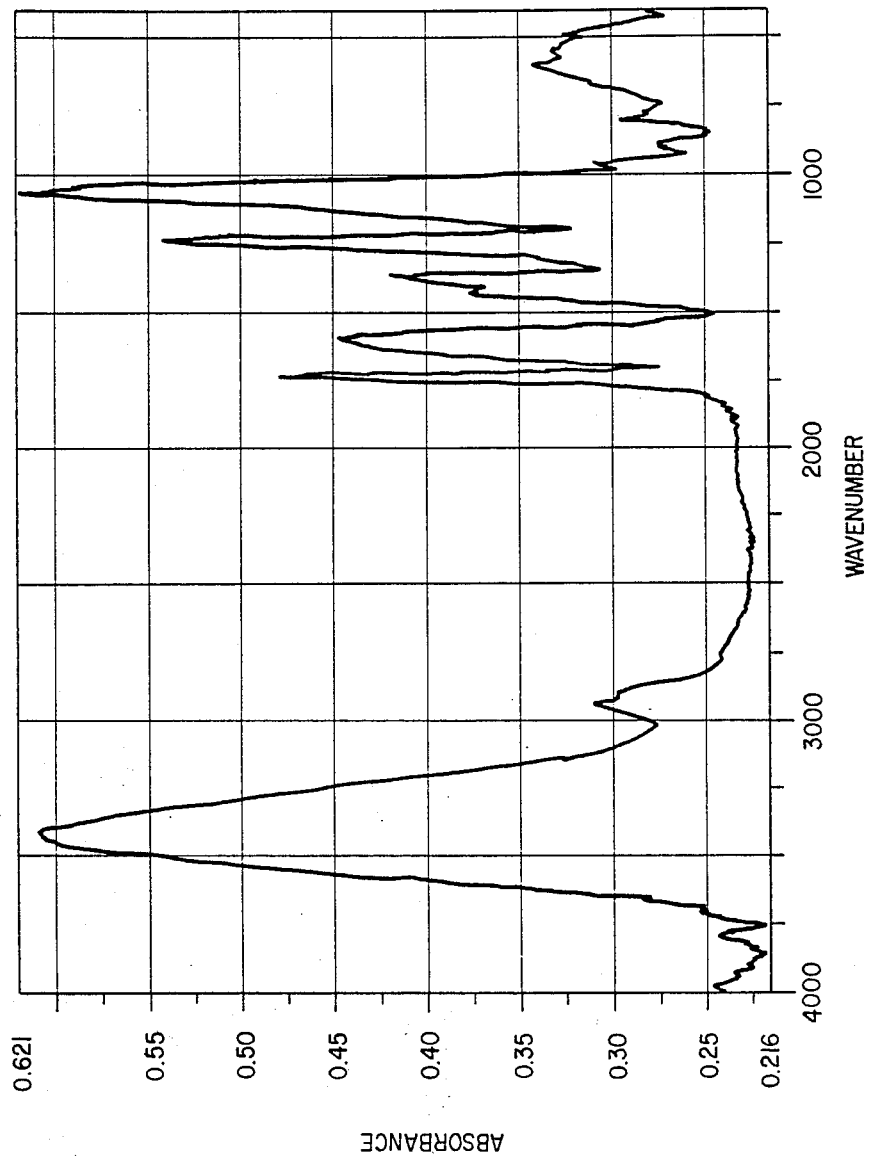
FIGS. 8–13 show infrared spectra for different samples of Carrisyn™.
Figure 9:
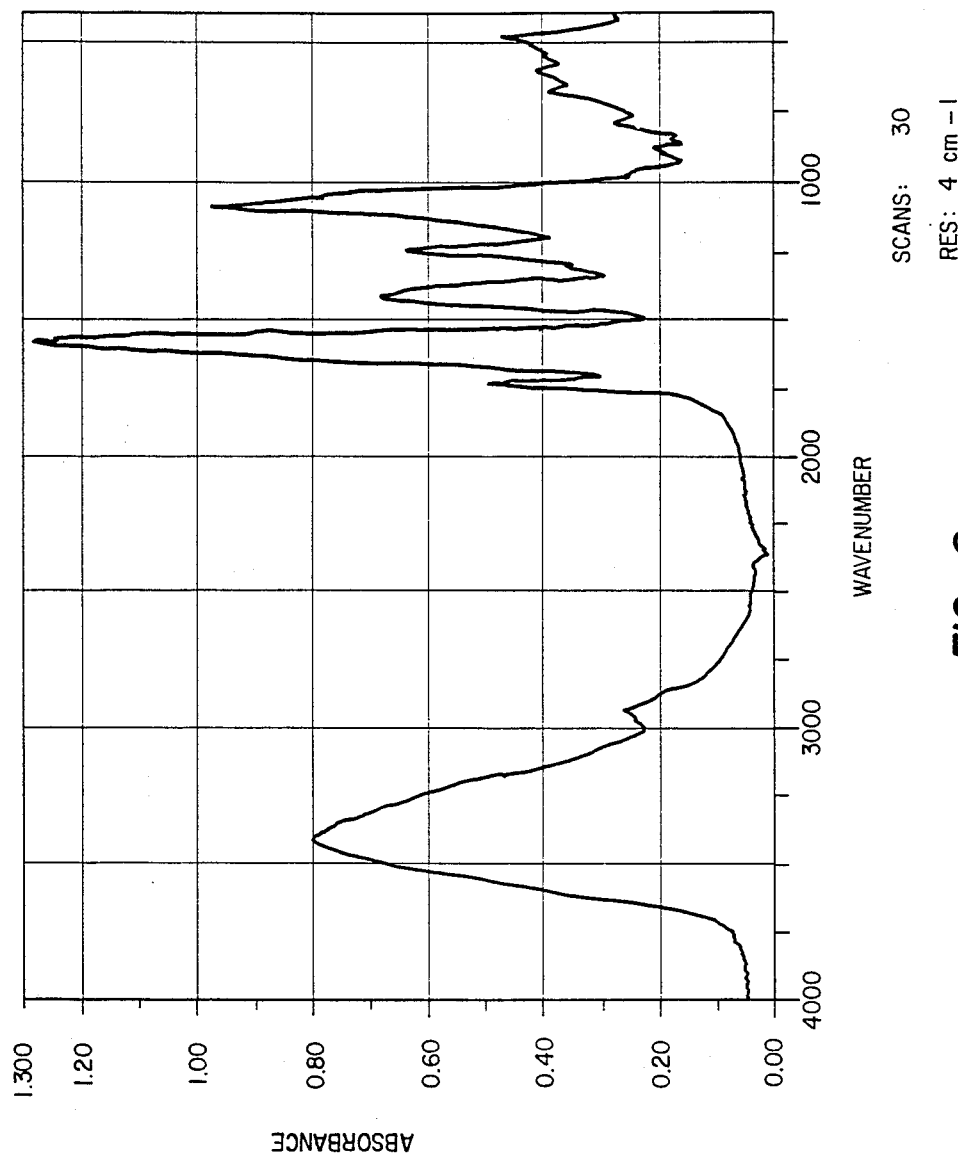
Figure 10:
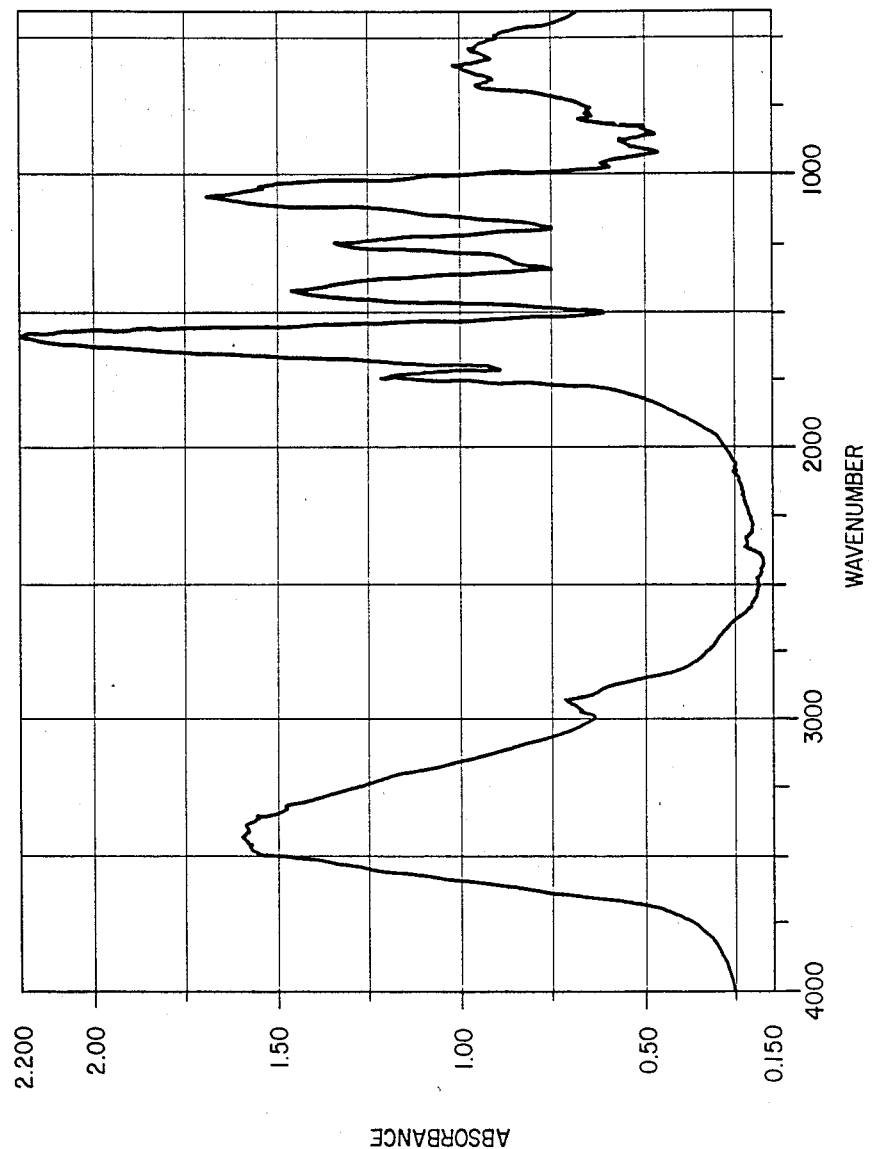
Figure 11:
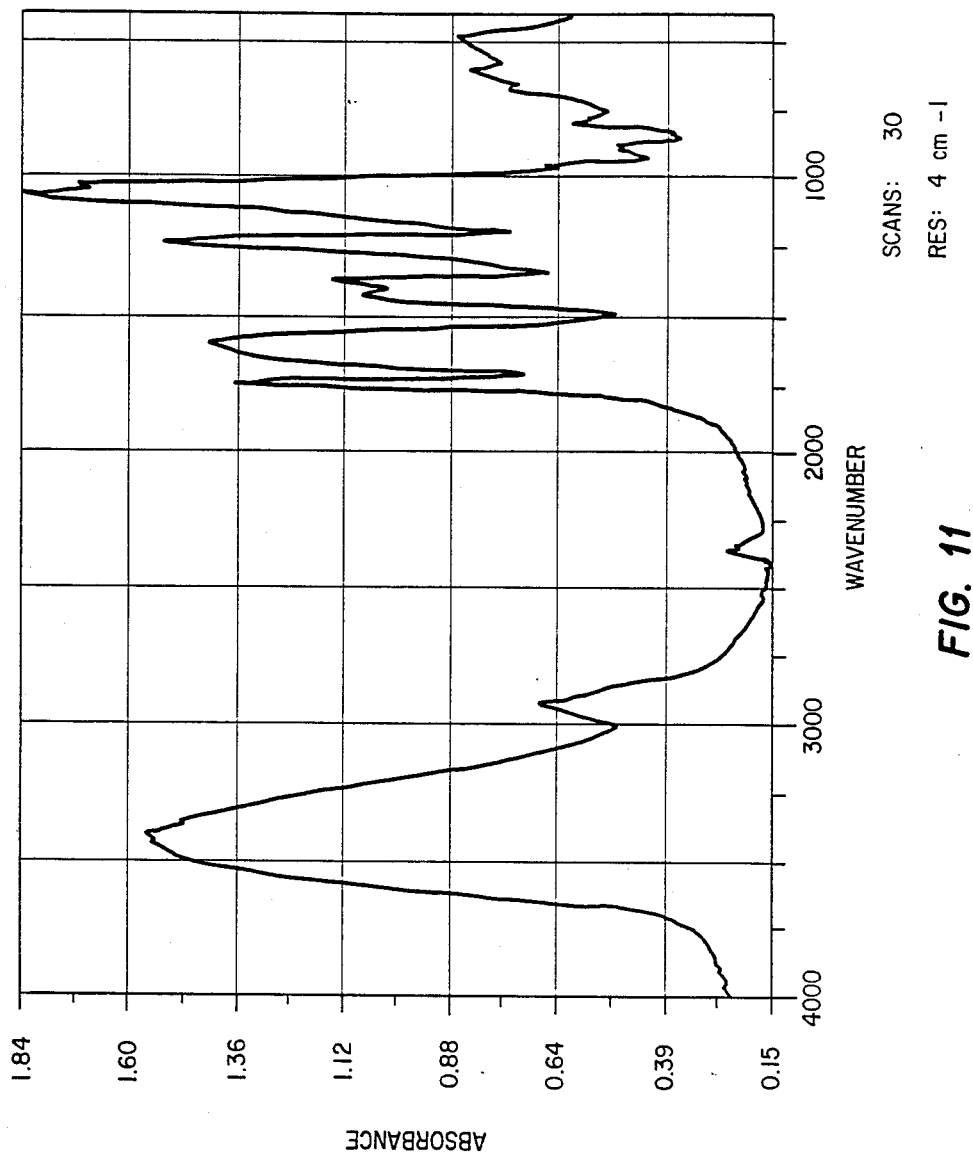
Figure 12:
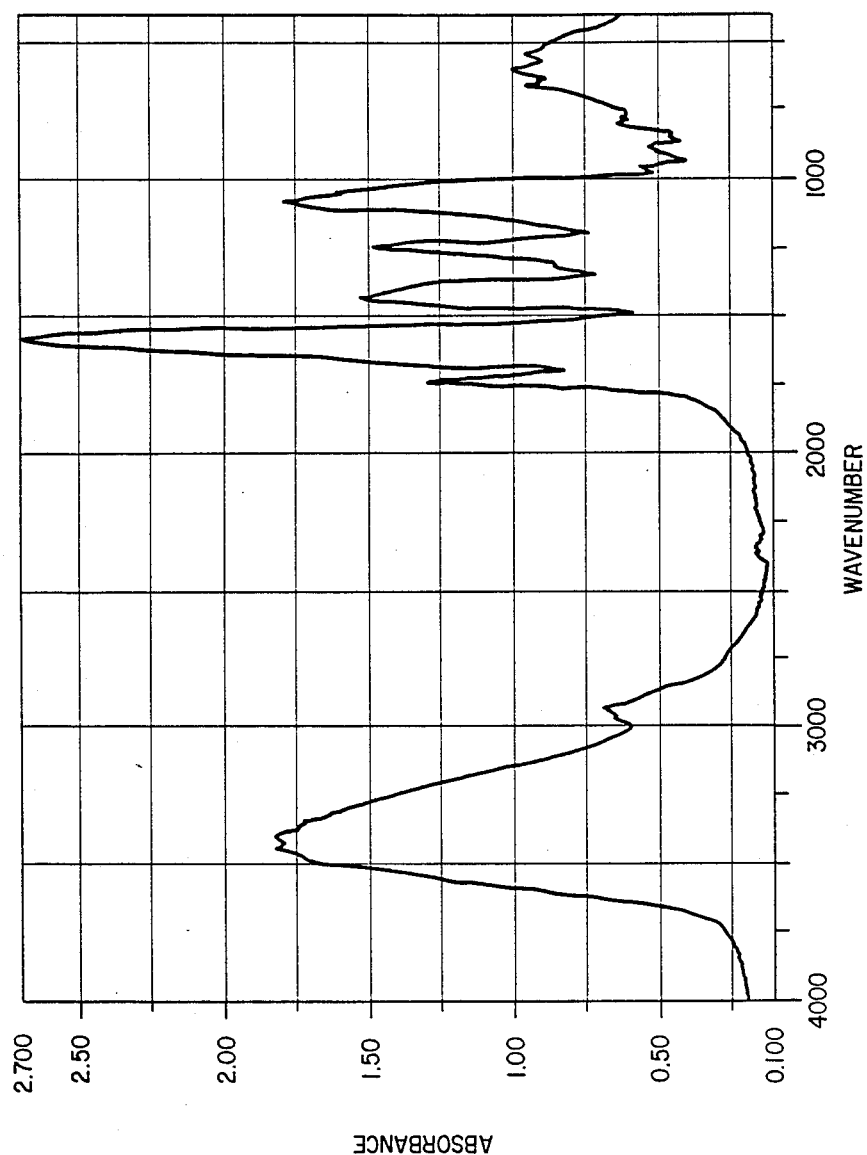
Figure 13:
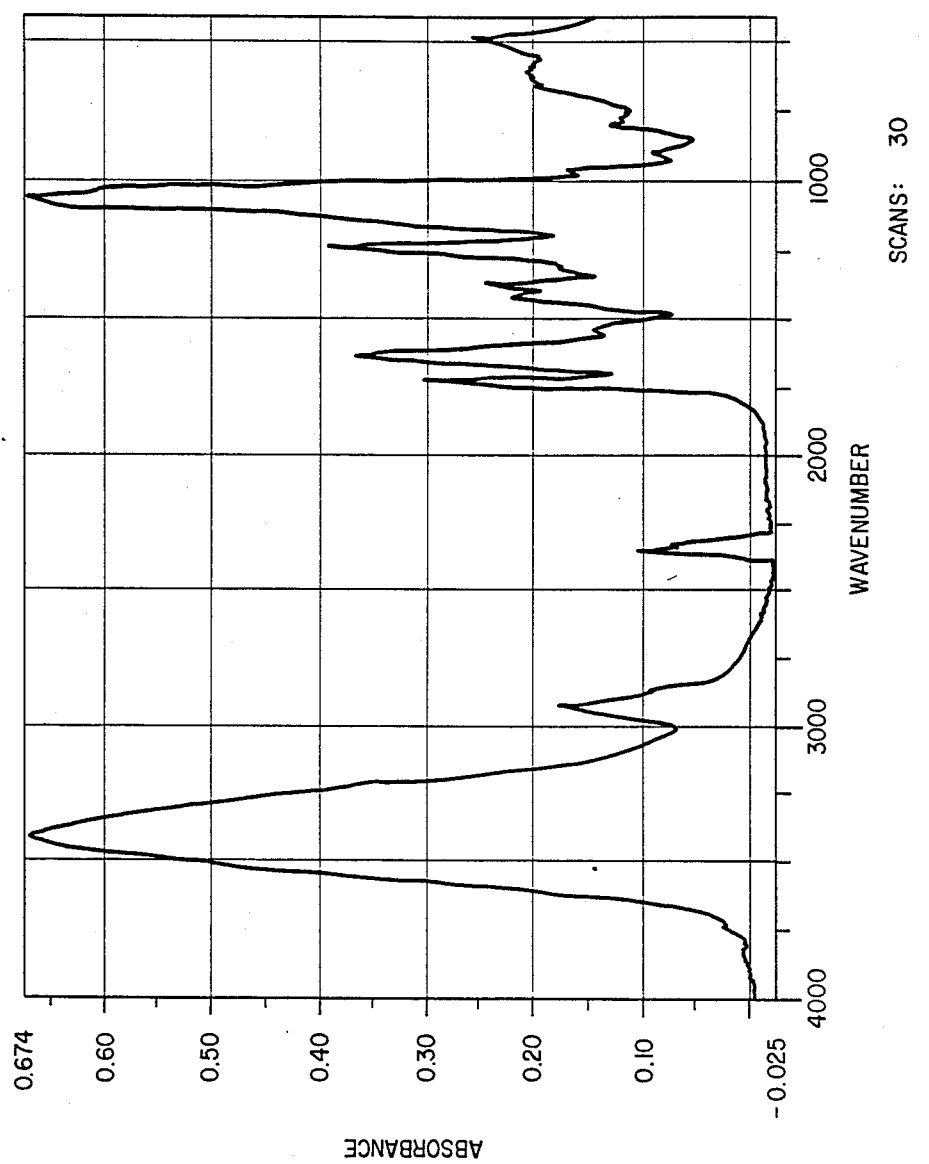

In FIG. 7, finely ground fillet Δ, is partially filtered, is stirred by mixer 29 and pumped through pump 30 into a dialyzer. Mixer 29 is a Perma-San ™ agitator (Model No. AAPH2) distributed through Van Tone, Inc., Dallas, Texas. Pump 30 is a Superior stainless steel Model SCS45 process pump (Superior Stainless Steel Company, Delavan, Wisconsin). Attached to process pump 30 is motor 30a of 3 horsepower made by Baldor Motor of 4450 rpm (Cat. No. CM3559T of the Baldor Electric Company, Ft. Smith, Arkansas). Material pumped through pump 30 passes through dialysis unit J, (a Romicon Model HF4SSS ultrafiltration system made by Romicon Inc., Woburn, Massachusetts) having 4 filters 31 (not shown) each filter housed in filter housing 32. Material passes vertically to a point where portions can be removed through separation lines 34 and into separation discharge lines 35. Other material not separated is recycled through recycle return line 33 back into the dialysis unit, or in the alternative, through separation return line 36 back into the vat I.

Depending on the fraction of aloe desired and end product sought, the desired material can either be obtained through separation discharge line 35 after processing or in vat I. For example, if excess water and minerals need to be removed, a small pore size ultrafilter can be used to separate out the water and minerals which are discharged through line 35 and the desired aloe fraction is returned to vat I. This process can be repeated until the desired amount of salt and water is removed from the product contained in vat I simply by circulating it through the dialysis unit. This process can include more than one diaysis step. For example, as previously described, the salts, low molecular weight acids and unwanted anthraquinones can be removed in a first dialysis step. The unwanted material is discharged through separation discharge line 35 and the desired fraction is returned to vat I. This step is accomplished by using ultrafilters obtained from Romicon with 10,000 Dalton pores. Next, the 10,000 Dalton ultrafilters are replaced with 50,000 Dalton ultrafilters also obtained from Romicon and the dialysis process is repeated. The dialysis process now separates the gel matrix polymers into two fractions; a first fraction consists of gel matrix polymers ranging in size from 10,000 to 50,000 Daltons and is discharged through separation discharge line 35, a second fraction consists of gel matrix polymers greater than 50,000 Daltons in size and is returned to vat I. This process can last from minutes to hours, depending upon the amount of salt and water that is needed to be removed from a given product. This is important because topical aloe products must have the salt and water content adjusted if they are to be used on damaged skin. The salt content can cause burning and irritation.

In FIG. 7, separation return line 36 is made of Tygon tubing (food grade) provided by the Texas Rubber Supply Company, Dallas, Texas. The separation discharge line 35 is a 316 stainless steel pipe distributed by Van Tone, Inc., Dallas, Texas.

EXAMPLE 2

Preparation of *Aloe vera* for drinking. By using 100 gallon (379 liters) of *Aloe vera* gel by Example 1, with the following specific preservatives:

EQUIPMENT REQUIRED

1. Two (2) 100 gallon stainless steel tanks with mixer.
2. One (1) 1,000 gallon stainless steel tank with mixer.
3. Homogenizer with pump.
4. Stainless steel screen.
5. One (1) transfer pump of suitable capacity.
6. Connecting hoses and stainless steel fittings.

BLENDING PROCEDURE

Prior to the addition of raw Aloe vera gel to the collection tank, complete steps 1 and 2 below:

1. Add 40 gallons (151.4 liters) of D.I. water
2. Dissolve, with agitation, the following chemicals in the deionized water in the collection tank (see item 13, infra):

Sodium Benzoate
Glycine
Citric Acid
Potassium Sorbate
Vitamin E

3. With continued agitation, collect raw aloe vera gel from the grinder into the collection tank to make a total volume of 100 gals. (379 liters).
4. Remove tank to the compounding area.
5. Place the next collection tank under the grinder discharge.
6. Set previously sanitized homogenizer at 1500 psi pressure and connect to the collection tank.
7. Start homogenizer and discharge product to open stainless steel basket mounted in the 1,000 gallon stainless steel tank.
8. Start agitation when product covers mixer's blade. Record time that agitation is started and finished, until 1,000 gal. tank is emptied (approx. 8 hours).
9. Continue to agitate, slow speed.
10. Dialyze product to adjust aloin content to 50 ppm or less and reduce excess acid, if necessary.
11. Add vanilla flavor and cinnamon oil-natural W.S. and mix for twenty minutes.

| INGREDIENTS | AMOUNT REQUIRED |
| --- | --- |
| D.I. Water (40.0 gals.) | 151.4 L. |
| Sodium Benzoate USP | 378 g. |
| Glycine | 3.0 kg. |
| Citric Acid USP | 416 g. |
| Potassium Sorbate USP | 189 g. |
| Vitamin E (1000 units) | 1 capsule |
| Raw Aloe Vera Gel q.s. to (100 gals.) | 379 L. |
| Flavor | |
| Vanilla | 121.0 g. |
| Cinnamon Oil - Natural W.S. | 8.0 ml. |

EXAMPLE 3

Aloe vera gel for manufacturing *Aloe vera* cosmetics. One hundred gallons (379 liters) of fine homogenized Aloe gel prepared by Example 1 was pumped to a stainless steel diatomite filter made by Lomart of 960 Alabama Avenue, Brooklyn, NY. The filter was a diatomaceous earth filter typical of the type used in swimming pools. Substantially all fibrous material was removed from the homogenized aloe gel fillet-preservative solution by the diatomite filter to produce a pulp-free aloe gel fillet-preservative solution.

EQUIPMENT REQUIRED

1. One (1) 100 gallon stainless steel tank with mixer.
2. One (1) 1,000 gallon stainless steel tank with mixer.
3. Homogenizer with pump.
4. Stainless steel screen.
5. One (1) transfer pump of suitable capacity.
6. Pool filter and attachments.
7. Connecting hoses and stainless steel fittings.

PRELIMINARY WORK

1. Sanitize the previously cleaned tanks, mixers and fittings with 50% IPA solution and rinse free of IPA with hot deionized Water.
2. Drain 5% HTH solution from pumps and attached hoses. Flush with water.
3. Sanitize pump and attached hoses with 50% IPA solution. Flush pumps and attached hoses with hot deionized water until free of isopropyl alcohol (IPA).
4. Sanitize homogenizer and attached hoses and pumps with 50% isopropyl alcohol solution. Flush homogenizer and attached hoses with hot deionized water until free of IPA.
5. Sanitizing procedure for the pool filter: (A) Prepare a 5% dissolved solution of swimming pool chlorine HTH powder in water and circulate through the entire system for twenty minutes.

BLENDING PROCEDURE

Prior to the addition of stabilized raw *Aloe vera* gel to the collection tank complete steps 1 and 2.

1. Add 50 gals. (189 liters) of deionized water.
2. Dissolve, with agitation, the following chemicals in the deionized water in the collection tank:
Methylparaben
Potassium Sorbate
3. With continued agitation, collect stabilized raw *Aloe vera* gel from the grinder into the collection tank to make a total volume of 100 gals. (379 liters).
4. Remove tank to the compounding area.
5. Set previously sanitized homogenizer at 1500 psig pressure and connect to the collection tank.
6. Start homogenizer and discharge product to open stainless steel basket mounted in 1,000 gallon stainless steel tank.
7. Start agitation when product covers mixer's blade. Record time agitation started.
8. Continue to agitate, slow speed for 20 minutes.
9. Add all 100 gallon portions manufactured to the 1,000 gallon tank.
10. Allow product to set over night.
11. Preparation of pool filter:
A. Flush the sanitizing solution from the pool filter using hot deionized water.
B. Add 1 kg. of Diatomaceous earth to 10 gallons of deionized water and mix until suspended.
C. Circulate mixture through the pool filter until the water is clear.
12. Flush excess water from pool filter with product.
13. Circulate product through the filter until product is clear of pulp.
14. Mix for 30 minutes.
15. Dialyze, if necessary, to reduce yellow sap to 50 parts per million or less, and to keep osmolarity to less than 150 millosmole.

| INGREDIENTS | AMOUNT REQUIRED |
|---|---|
| D.I. Water (50 gals.) | 189 L. |
| Methylparaben | 681 g. |
| Potassium Sorbate | 379 g. |
| Raw Aloe Vera Gel q.s. to volume or to 100 gals. | 379 L. |

EXAMPLE 4

Production of Aloe Cream

Starting with 71.6 gallons (271 liters) of *Aloe vera* gel for manufacturing Aloe vera cosmetics prepared by Example 3.

EQUIPMENT REQUIRED

1. One (1) suitable size round bottom, jacketed, stainless steel kettle equipped with counter-motion agitation and nylon scrapers.
2. One (1) suitable size cylindrical, jacketed, stainless steel tank equipped with a variable speed mixer.
3. One (1) transfer pump.
4. Tygon and/or polyethylene connecting hoses, stainless steel fittings, suitable size containers and stainless steel filter.

PRELIMINARY WORK

Sanitize the previously cleaned kettle, tank, mixers, pump, hoses, and containers.

PREPARATION OF THE AQUEOUS PHASE

1. Add the following items to the cylindrical tank and start agitation when Stabilized *Aloe vera* Gel for Mfg. has covered the mixing blade:
Stabilized *Aloe vera* Gel for Mfg.
Propylene Glycol
Allantoin
Methylparaben
GERMALL 115 TM Imidazolidinyl urea (Sutton Laboratories, Chatham, NJ 07928)
Sorbitol 70
Phosphoric Acid
2. Heat to 75° C.±5° C. with agitation and maintain temperature.
3. Mix until all items are in solution.

PREPARATION OF THE OIL PHASE

1. Into a separate kettle add the following items:
Glyceryl Stearate
Stearyl Stearate
Wickenol TM 163 (Wickham Products, Inc., Huguenot, NY 12746)
Lexamine TM P-13 (Inolex Chemical Co., Philadelphia, Pa 19148)
Cetyl Alcohol
Lanolin Mineral Oil (Light) (Kaydol) (Delta Solvents and Chemicals, Dallas, TX 75285)
Dimethicone
Propylparaben
Vitamin E Natural
LEXEIN QX-3000 (Inolex Chemical Co., Philadelphia, PA 19148)

2. Heat to 75° C.±5° C. with slow agitation until material is melted and homogeneous.

FORMULATION OF EMULSION

For successful emulsification, the oil and water phases should be added at the same temperature when blending. This process should then proceed without interruption.

1. With slow agitation, add water phase slowly to the oil phase.
2. Immediately turn off steam, drain jacket and start force cooling with cold domestic water, continuing slow agitation.
3. q.s. to batch size with deionized water at 75° C.±5° C. if necessary.
4. When product cools to 40° C.±5° C., add the fragrance.
5. When cooled to 30° C., stop agitation and submit sample for approval.

| INGREDIENTS | AMOUNT REQUIRED |
|---|---|
| WATER PHASE | |
| Stablized Aloe Vera Gel for Mfg. (71.6 gals.) | 271 Kg. |
| Propylene Glycol | 17.4 Kg. |
| Allantoin | 908 g. |
| Methylparaben | 690 g. |
| Imidazolidinyl Urea (Germall TM 115) | 2.0 g. |
| Sorbitol 70 | 908 g. |
| Phosphoric Acid | 1.05 Kg. |
| OIL PHASE | |
| Glyceryl Stearate (Lexemul TM 515) (Inolex Chemical Co., Philadelphia, PA 19148) | 35.6 Kg. |
| Stearyl Stearate (Lexol TM SS) (Inolex Chemical Co., Philadelphia, PA 19148) | 8.9 Kg. |
| Dioctyl Adipate (and) Octyl Stearate (and) Octyl Palmitate (Wickenol 163 TM, Wickam Products, Inc., Huguenot, NY 12746) | 8.9 Kg. |
| Palmitamidopropyl Dimethylamine (Lexamine P-13 TM, Inolex Chemical Co., Philadelphia, PA 19148) | 3.5 Kg. |
| Cetyl Alcohol | 3.5 Kg. |
| Lanolin | 3.5 Kg. |
| Light Mineral Oil (Light) (Kaydol) (Delta Solvents and Chemicals, Dallas, TX 75285) | 3.5 Kg. |
| Dimethicone | 908 g. |
| Propylparaben | 399 g. |
| Vitamin E Natural | 363 g. |
| Cocamidopropyldimonium Hydroxypropylamino Collagen (LEXEIN TM QX-3000 Inolex Chemical Co., Philadelphia, PA 19148) | 363 g. |
| | 109 g. |
| Elias Fragrance #5394 (Elias Fragrances, Brooklyn, NY 11203) | 109 g. |

EXAMPLE 5

Preparation of a counter-irritant, starting with 115 gallons (436 Kg) of stabilized *Aloe vera* gel for manufacturing, prepared by Example 3.

EQUIPMENT REQUIRED

1. One (1) suitable size round bottom, jacketed, stainless steel kettle equipped with counter-motion agitation and nylon scrapers.
2. One (1) suitable size cylindrical tank with a variable speed mixer.
3. One (1) transfer pump.
4. Tygon and/or polyethylene connecting hoses, stainless steel fittings, suitable size containers and stainless steel filter.

PRELIMINARY WORK

Sanitize the previously cleaned kettle, tank, mixers, pump, hoses, and containers.

CARBOPOL SLURRY

1. Add deionized water to the mixing tank. Start mixer.
2. Slowly add all Carbomer TM 940 (Carbopol 940 TM) (B. F. Goodrich Chemical Group, Chicago, IL 60694) to the mixing tank. Continue mixing until solvated.
3. Let set overnight. Turn mixer and mix for 1 hour.

PREPARATION OF THE AQUEOUS PHASE

1. Add the following items to the cylindrical tank and start agitation when deionized Water has covered the mixing blade:

Deionized Water (Retain 10 gals. to rinse Carbopol Slurry from tank.)
Stabilized *Aloe Vera* Gel
Propylene Glycol
Triethanolamine 99%
Allantoin
methylparaben
Potassium Sorbate
Urea 2. Heat to 70° C.±5° C. with agitation and maintain temperature.
3. Mix until all items are in solution.
4. Add Carbopol Slurry and mix until free of "fish eyes".
5. Rinse tank with deionized Water.

PREPARATION OF THE OIL PHASE

1. Into a kettle add the following items:
Petrolatum (White TM) (Delta Solvents and Chemicals, Dallas, TX 75285)
Mineral Ol (Carnation White TM) (Delta Solvents and Chemicals, Dallas, TX 75285)
Mineral Oil (and) Lanolin Alcohol (Amerchol L-101 TM) (Amerchal, Edison, NJ 08817)
Acetylated Lanolin Alcohol (Fancol ALA TM) (Delta Solvents and Chemicals, Dallas, TX 75285)
Stearic Acid Triple Pressed
Glyceryl Stearate (Lexemul 515 TM) (Inolex Chemical Co., Philadelphia, PA 19148)
Cetyl Alcohol
Dioctyl Adipate (and) Octyl Stearate (and) Octyl Palmitate (Wickenol TM 163) (Wicken Products Inc., Heugenot, NY 12746)
White Oleic Acid USP
Stearyl Stearate (Lexol SS TM)(Inolex Chemical Co., Philadelphia, PA 19148)
Propylparaben
Butylparaben
Eucalyptus Oil Methyl Salicylate
Camphor
Menthol
Histamine Dihydrochloride
Oil of Cinnamon 2. Heat to 70° C.±5° C. with slow agitation until material is melted and homogenous.

FORMULATION OF EMULSION

Note: For successful emulsification, the oil and water phases should be added at the same temperature when blending. This process should then proceed without interruption.

1. With slow agitation, add water phase slowly to the oil phase.
2. Immediately turn off steam, drain jacket, and start force cooling with cold domestic water, containing slow agitation.
3. q.s. to batch size with deionized water at 70° C.±5° C. if necessary.
4. When cooled to 35° C., stop agitation and submit sample for approval.

| INGREDIENTS | AMOUNT REQUIRED |
| --- | --- |
| Carbopol Slurry | |
| Deionized Water (30 gals.) | 113 Kg. |
| Carbomer 940 (Carbopol 940 TM) (B. F. Goodrich Chemical Group, Chicago, IL 60694) | 4.36 Kg. |
| Water Phase | |
| Stabilized Aloe Vera Gel for Mfg. (115 gals.) | 436 Kg. |
| Deionized Water (41.5 gals.) | 157 Kg. |
| Propylene Glycol | 54.5 Kg. |
| Triethanolamine 99% | 9.8 Kg. |
| Allantoin | 653 g. |
| Methylparaben | 1.1 Kg. |
| Potassium Sorbate | 545 g. |
| Urea | 21.8 Kg. |
| Oil Phase | |
| Petroleum USP(White) (Delta Solvents and Chemicals, Dallas, TX 75285) | 8.2 Kg. |
| Mineral Oil (Carnation White TM) (Delta Solvents and Chemicals, Dallas, TX 75285) | 8.2 Kg. |
| Mineral Oil (and) Lanolin Alcohol (Amerchol L-101 TM) (Americhol, Edison, NJ 08817) | 7.6 Kg. |
| Acetylated Lanolin Alcohol (Fancol ALA TM) (Delta Solvents and Chemicals, Dallas, TX 75285) | 7.6 Kg. |
| Stearic Acid Triple Pressed | 23.5 Kg. |
| Glyceryl Stearate (Lexemul 515 TM) (Inolex Chemical Co., Philadelphia, PA 19148) | 10.3 Kg. |
| Cetyl Alcohol | 8.2 Kg. |
| Dioctyl Adipate (and) Octyl Stearate (and) Octyl Palmitate (Wickenol 163 TM) (Wicken Products, Inc., Huegenot, NY 12746) | 10.3 Kg. |
| White Oleic Acid USP | 1.1 Kg. |
| Stearyl Stearate (Lexol SS TM) (Inolex Chemical Co., Philadelphia, PA 19148) | 1.1 Kg. |
| Propylparaben | 1.1 Kg. |
| Butylparaben | 1.1 Kg. |
| Eucalyptus Oil | 21.8 Kg. |
| Methyl Salicylate | 136 Kg. |
| Camphor | 21.8 Kg. |
| Menthol | 21.8 Kg. |
| Histamine Dihydrochloride | 545 g. |
| Oil of Cinnamon | 218 g. |

EXAMPLE 6

Preparation of freeze-dried Aloe. Starting with one liter of *Aloe vera* gel, prepared by Example 2. Place the juice in a freeze drying unit and produce approximately 45 grams of freeze-dried Aloe.

EXAMPLE 7

Preparation of a topical wound gel. Start with *Aloe vera* gel prepared by Example 3 and concentrate to 190 percent by dialysis.

EQUIPMENT REQUIRED

1. Two (2) suitable size stainless steel tanks with mixer.
2. One (1) Romicon TM concentrator system.
3. One (1) transfer pump.
4. Tygon and/or polyethylene connecting hoses, stainless steel fittings, suitable size containers and stainless steel filter.

PRELIMINARY WORK

1. Sanitize the previously cleaned tanks, mixers, pump, hoses, and containers used during the manufacturing process.
2. Prepare Carbopol Slurry one day before manufacturing.
3. Sanitize the previously cleaned Romicon TM concentrator system. The entire system is washed with deionized water and filled with 37% hydrogen peroxide and allowed to stand overnight.

CONCENTRATION OF ALOE VERA GEL FOR DERMAL WOUND GEL PREPARATION FOR TREATING DECUBITUS ULCERS

1. Flush the concentrator system with deionized Water until free of hydrogen peroxide.
2. Separate the calculated quantity of effluent from the Aloe Vera Gel required to concentrate the product of 190% Gel.

CARBOPOL SLURRY

1. Add Aloe Vera Gel-190% to the mixing tank. Start mixer.
2. Slowly add the Carbomer 940 (Carbopol 940 TM) (B. F. Goodrich Chemical Group, Chicago, IL 60694) to the water in the mixing tank. Continue mixing until solvated.
3. Let set overnight. Turn on mixer and mix for 1 hour.

MIXING PROCEDURE

1. In a suitable size mixing tank, add the following items and start mixer when the blade is covered:
   *Aloe vera* Gel 190%
   Panthenol
   Allantoin
   L-Glutamic Acid Imidazolidinyl UREA (GERMALL 115 TM) (Sutton Industries, Chatham, NJ 07928)
   Potassium Sorbate
   Sodium Benzoate
   Triethanolamine 99%
2. Continue mixing while adding Carbopol Slurry which has been strained through 100 mesh stainless steel screen.
3. Mix until free of "fish eyes".
4. Read the pH and record, pH range 5.0±0.5.

5. Adjust pH if required with Citric Acid or Triethanolamine.

6. Record pH.

7. When product is complete, submit sample for approval.

8. When ready for filling, pump through 100 mesh stainless steel screen into filling hopper.

| INGREDIENTS | AMOUNT REQUIRED |
|---|---|
| Carbopol Slurry | |
| Conc. Stabilized Aloe Vera Gel 5X 190%) (75 gals.) | 284 Kg. |
| Carbomer 940 (Carbopol 940 TM) (B. F. Goodrich Chemical Group, Chicago, IL 60694) | 13.3 Kg. |
| Conc. Stabilized Aloe Vera Gel (5X 190%) (403 gals.) | 1523 Kg. |
| Panthenol | 37.9 Kg. |
| Allantoin | 11.4 Kg. |
| L-Glutamic Acid | 5.7 Kg. |
| Imidazolidinyl Urea (Germall 115 TM) (Sutton Laboratories, Chatham, NJ 07928) | 1.9 Kg. |
| Triethanolamine 99% | 13.3 Kg. |
| Potassium Sorbate | 945 g. |
| Sodium Benzoate | 1.9 Kg. |

EXAMPLE 8

Starting with 100 kilograms of leaves straight from the field, not washed. 51.2 kilograms of *Aloe vera* juice is collected using a "Thompson Aloe Juice extractor made by Thompson Manufacturing Co., Harlingen, Texas 78550. The extractor is operated according to the directions supplied by the manufacturer. The resulting 51.2 kilograms of Aloe juice extract has 0.1% methylparaben added and mixed for 20 minutes in a one hundred gallon stainless steel tank with mixer. Then the solution is dialyzed using the Romicon TM ultrafiltration equipment until the anthraquinone content is less than 50 ppm by weight and this gel is used to produce the Aloe Creme of Example 4.

SEPARATION AND ISOLATION PROCESS

As discussed above in the fractionation process, the filleted internal gel matrix portion of the *Aloe vera* leaf in the form of gel matrix strips can be homogenized and filtered to remove the interstitial fibers sub-portion, leaving the residual matrix sub-portion. The residual matrix sub-portion may then be treated to separate, isolate and purify the active chemical substance, CARRISYN® extract, in *Aloe vera* gel. To separate CARRISYN® extract from the residual matrix sub-portion, an excess of a water soluble, lower aliphatiac polar solvent is added to the residual matrix sub-portion. CARRISYN® extract then begins to precipitate from this mixture. The solution is allowed to settle for a sufficient period of time to allow as much active ingredient to precipitate out of solution as possible but not so long that the CARRISYN® extract begins to degrade. After this period of time, the supernatant is decanted or siphoned off without disturbing the settled precipitate. The precipitate and remaining solution is then placed in an appropriate centrifuge apparatus and is collected into a pellet. After centrifugation, the supernatants are decanted and discarded. Optionally, the pellets are washed with a fresh aliquot of the water soluble, lower-aliphatic polar solvent and collected again and the supernatants are again, discarded. The pellet is then lyophilized to dryness and allowed to dry overnight. The resulting product is a substantially non-degradable lyophilized form of CARRISYN® extract. The resulting product may be ground to form a powder.

An alternate and preferred process for separating and isolating CARRISYN® extract includes the following steps.

Leaves from mature, outdoor grown *Aloe vera* plants are pulled or cut from near the base of the plant, preferably without breaking or damaging any part of the leaf prior to processing. The leaf is preferably cut at the base of the plant immediately above the stalk and is peeled from the stalk, in order to prevent leakage of the clear cellular gel or contamination of the gel with the yellow sap.

After removal from the plant, the butt and tip portions of the leaves are removed and the cut leaves are pared to form fillets as described above in the fractionation process.

The resultant fillet (internal gel matrix) is then ground, shredded or blended, to break up the interstitial fibers present therein or the internal gel matrix, may be forced through a wire mesh or filter screen in order to achieve liquefaction. The resultant liquefied internal gel matrix is then homogenized. The homogenized extract thus obtained typically has a pH of approximately about 4 to about 5, preferably about 4. The homogenized extract is then filtered to remove the interstitial fibers. The homogenized and filtered extract may then be treated in the identical manner as the residual matrix sub-portion, referred to immediately above, to separate and isolate CARRISYN® extract.

An additional alternate and preferred process for separating and isolating CARRISYN® extract includes the following steps.

Leaves from mature, outdoor grown *Aloe vera* plants are pulled or cut from near the base of the plant, preferably without breaking or damaging any part of the leaf prior to processing. The leaf is preferably cut at the base of the plant immediately above the stalk and is peeled from the stalk, in order to prevent leakage of the clear cellular gel or contamination of the gel with the yellow sap.

The leaves may then be crushed by suitable means, for example a "Thompson Aloe Extruder" made by Thompson Manufacturing Company, Harlingen, Texas, to extrude aloe juice. The extruded aloe juice may then be treated in the identical manner as the residual matrix sub-portion, referred to above, to separate and isolate CARRISYN® extract.

All steps in the processes described are performed at about room temperature, except for the lyophilization step, which is preferably performed at about −50° C.

Various modifications of the disclosed processes and compositions of the invention, as well as alternative modifications, variations and equivalents will become apparent to persons skilled in the art upon reading the above general description. The following examples are illustrative only and are not intended to limit the scope of the appended claims, which cover any such modifications, equivalents or variations.

EXAMPLE 9

Process for Separating and Isolating CARRISYN ® extract.

A. Preliminary Work:

1. Previously cleaned tanks, mixers and fittings were sanitized with 50% isopropyl alcohol (IPA) solution and rinsed free of IPA with hot deionized Water.

2. Pumps and attached hoses were drained with 5% "HTH" chlorine swimming pool solutions, then flushed with water.

3. The pumps and attached hoses were sanitized with 50% isopropyl alcohol solution. Pumps and attached hoses were flushed with hot deionized water until free of IPA.

4. An homogenizer and attached hoses and pumps were sanitized with 50% isopropyl alcohol solution. The homogenizer and attached hoses were flushed with hot deionized water until free of IPA.

*Aloe barbadensis* Miller leaves collected from the Rio Grande Valley were transferred in a refrigerated truck at 40° to 45° F. within eight hours after harvest and stored under refrigeration at 40° to 45° F. until processed to reduce degradation.

Twenty to sixty pounds of stored leaves were then placed in a prewash bath of an aqueous solution of calcium hypochlorite at room temperature, substantially to remove surface dirt from the leaves and kill surface bacteria on the leaves. The aqueous solution of calcium hypochlorite was prepared by adding approximately 0.125 grams of 98% calcium hypochlorite to one liter of water to produce a solution containing 50ppm of free chlorine. The leaves remained in the prewash bath for a period of approximately five minutes.

Next, the substantially dirt and bacteria free leaves were placed on the horizontal conveyor belt of a "Thompson Aloe Washer" made by Thompson Manufacturing Company, Harlingen, Texas. The "Thompson Aloe Washer" washed the leaves with room temperature water to remove the surface dirt and aqueous solution of calcium hypochlorite from the leaves. Again, the leaves were visually inspected and hand scrubbed as necessary to remove any surface dirt remaining on the leaves. Such leaves were then rinsed with room temperature water.

The tip and butt portion was then removed from each leaf and the leaves were placed in stainless steel basket-type containers, placed together on top of a funnel shaped stainless steel collector, each container having a mesh bottom. Yellow sap was allowed to drain from the leaves for approximately 30 minutes. The yellow sap passed through the mesh bottom of the stainless steel basket and was collected in a funnel shaped collector.

The stainless steel basket type containers containing the aloe leaves were removed from the collector, and were then submerged in a second stainless steel vessel comprising a room temperature water bath of continuously horizontally flowing rinse water moving counter-current to the containers which are slowly moved by hand from one end of the vessel to the other, for approximately thirty minutes to one hour. This allows the yellow sap to drain further from the leaves. The leaves were allowed to soak in this solution for 30 minutes.

The leaves were then removed from this solution and the rind was removed from each leaf with a sharp knife or wire cheese slicer to produce an aloe gel fillet from each leaf portion. The aloe gel fillets were visually inspected and any contaminated aloe gel fillets or fillet part detected by a characteristic yellowish discoloration were discarded. The total mass of uncontaminated aloe gel fillets was 20 to 60 percent of the starting leaf mass depending on the leaf size and condition.

The uncontaminated aloe gel fillets were then placed in a 750 seat restaurant set stainless steel garbage disposal unit which coarse ground the fillets to an average particle size of the consistency of a thick, but freely flowing (coarse homogenized) liquid. The stainless steel garbage disposal unit was made by the N-sinkerator TM Division of Emerson Electric Co., Racine, WI, Model No. SS-150-13, Serial No. 115132.

The coarse ground aloe gel fillets then passed to a 100 gallon stainless steel holding vat. The holding vat was made by Process Equipment Corp. of Belding, Michigan, Model No. 100 gallon OVC, Serial No. 40865-3.

From the holding vat, the coarse ground aloe gel fillet solution was pumped to a homogenizer. The homogenizer was made by Crepaco Food Equipment and Refrigeration, Inc., of Chicago, Illinois, Serial No. 04-03. The homogenizer was of a type typically used in dairy processes for the homogenization of milk. The coarse ground aloe gel fillet solution was finely homogenized under a pressure of about 1,500 psi.

From the homogenizer, the finely homogenized aloe gel fillet solution was pumped to a stainless steel storage tank. The storage tank was made by Process Equipment Corp. of Belding, Michigan, Model No. 1000 gallon OVC, Serial No. 400866-2. The total mass of the homogenized aloe gel fillet solution was 20 to 60 percent of the starting leaf mass. Then, if necessary, the homogenized product was dialyzed using ultrafiltration.

The finely homogenized aloe gel fillet solution was then filtered to remove the interstitial fibers using a Leslie's TM Diatomaceous Earth Filter Model De-48. The interstitial fibers themselves, instead of diatomaceous earth, were used as the filter media, the fibers being supported by a nylon mesh cloth filter support. The gel was pumped through the filter for several minutes before opening the exit port so that a sufficient amount of fibers could build up to serve as the filter media.

Twenty gallons of the filtered aloe gel fillet solution was then pumped into a 100 gallon tank and 80 gallons of 190 proof undenatured ethanol (Ethyl Alcohol, 190 proof, U.S.P., punctilious, 54 gal. Batch I.D. #CT185JO4 available through U.S. Industrial Chemicals, C., P.O. Box 218, Tuscola, Illinois 61953) was added to the aloe gel fillet solution.

The alcohol-gel solutions were then immediately transferred to several 11 quart pans of 10½" diameter and 8" high of 18-8 stainless steel (Bloomfield Industries Inc., Chicago, Illinois, available through Watson Food Service Equipment and Supplies, 3712 Hagger Way, Dallas, Texas).

The alcohol-gel solutions were then allowed to settle for approximately four hours.

The clear liquid supernatant was then decanted or siphoned off, using care not to disturb the precipitate that had settled on the bottom of the pans. The precipitate and remaining solutions were then transferred to four 1 pint stainless steel centrifuge buckets with about 500 g. of precipitate and remaining solution being transferred to each bucket. The buckets were then spun at 2,000×g for about 10 minutes using an IEC Centra-7 TM Centrifuge (International Equipment Co., 300 2nd Avenue, Needham Heights, Massachusetts 02194 available through: American Scientific Products, P.O. Box 1048, Grand Prairie, Texas 75050).

After centrifugation, the supernatants were decanted and discarded. The pellets were then washed with fresh 190 proof, undenatured ethanol and collected again at 2,000×g for about 10 minutes. After spinning again the supernatant was discarded.

The pellet was then transferred to several 600 ml. VIRTIS TM lyophilization jars and swirled in liquid nitrogen until frozen. The lyophilization jars were then attached to a lyophilization apparatus consisting of a Welch TM Duo-seal Vacuum Pump (Model No. 1402, available from Sargeant-Welch, P.O. Box 35445, Dallas, Texas 75235), a Virtis TM Immersion Coil Cooler (Model No. 6205-4350 Cooler in acetone bath) and a Virtis TM 18 Port Vacuum Drum Manifold (Model No. 6211-0350). All Virtis TM equipment is available from American Scientific Products, P.O. Box 1048, Grand Prairie, Texas 75050. The lyophilization drum was filled with acetone that was maintained at −50° C.

The samples were lyophilized to dryness overnight and were then weighed on a Mettler AE 163 TM balance. The samples remaining consisted of substantially non-degradable lyophilized CARRISYN ® extract. The yield from 50 gallons of aloe vera gel was approximately 370–380 g. of CARRISYN ® extract.

EXAMPLE 10

Process for Separating and Isolating CARRISYN ® extract.

*Aloe barbadensis* Miller leaves, collected from the Rio Grande Valley, were transferred in a refrigerated truck at 40° to 45° F. within eight hours after harvest and stored under refrigeration at 40° to 45° F. until processed to reduce degradation.

The tip and butt portions were then removed from each leaf. The rind was then removed from each leaf with a sharp knife or wire cheese slicer to produce an aloe gel fillet from each leaf portion.

The aloe gel fillets were then placed in a 750 seat restaurant set stainless garbage disposal unit which coarse ground the fillets to an average particle size of the consistency of a thick, but freely (coarse homogenized) liquid. The stainless steel garbage disposal unit was made by the N-sink-erator TM Division of Emerson Electric Co., Racine, WI, Model No. SS-150-13, Serial No. 115132.

The coarse ground aloe gel fillets then passed to a 100 gallon stainless steel holding vat. The holding vat was made by Process Equipment Corp. of Belding, Michigan, Model No. 100 gallon OVC, Serial 1No. 40865-3.

From the holding vat, the coarse ground aloe gel fillet solution was pumped to a homogenizer. The homogenizer was made by Crepaco Food Equipment and Refrigeration, Inc., of Chicago, Illinois, Serial No. 04-03. The homogenizer was of a type typically used in dairy processes for the homogenization of milk. The coarse ground aloe gel fillet solution was finely homogenized under a pressure of 1,500 psi.

From the homogenizer, the finely homogenized aloe gel fillet solution was pumped to a stainless steel storage tank. The storage tank was made by Process Equipment Corp. of Belding, Michigan, Model No. 1000 gallon OVC, Serial No. 40866-2. The total mass of the homogenized aloe gel fillet solution was 20 to 60 percent of the starting leaf mass. Then, if necessary, the homogenized product was dialyzed using ultrafiltration.

The homogenized gel was then filtered to remove the interstitial fibers using a Leslie's TM Diatomaceous Earth Filter Model DE-48. The interstitial fibers themselves, instead of diatomaceous earth, were used as the filter media, the fibers being supported by a nylon mesh cloth filter support. The gel was then pumped through the filter for several minutes before opening the exit port so that a sufficient amount of fibers could build up to serve as the filter media.

Twenty gallons of the filtered gel was then pumped into a 100 gallon tank and 80 gallons of 190 proof undenatured ethanol (Ethyl Alcohol, 190 proof, U.S.P., punctilious, 54 gal. Batch I.D. #CT185JO4 available through U.S. Industrial Chemicals, Co., P.O. Box 218, Tuscola, Illinois 61953) was added to the aloe gel fillet solution.

The alcohol-gel solutions were then immediately transferred to several 11 quart pans of 10½ diameter and 8" high of 18-8 stainless steel (Bloomfield Industries Inc., Chicago, Illinois, available through Watson Food Service Equipment and Supplies, 3712 Hagger Way, Dallas, Texas).

The alcohol-gel solutions were then allowed to settle for approximately four hours.

The clear liquid supernatant was then decanted, or siphoned off, using care not to disturb the precipitate that had settled on the bottom of the pans. The precipitate and remaining solutions were then transferred to four 1 pint stainless steel centrifuge buckets with about 500 g. of precipitate and remaining solution being transferred to each bucket. The buckets were then spun at 2,000×g for about 10 minutes using an IEC Centra-7 TM Centrifuge (International Equipment Co., 300 2nd Avenue, Needham Heights, Massachusetts 02194 available through: American Scientific Products, P.O. Box 1048, Grand Prairie, Texas 75050).

After centrifugation, the supernatants were decanted and discarded. The pellets were then washed with fresh 190 proof, undenatured ethanol and spun down again at 2,000×g for about 10 minutes. After spinning again, the supernatant was discarded.

The pellet was then transferred to several 600 ml. VIRTIS TM lyophilization jars and swirled in liquid nitrogen until frozen. The lyophilization jars were then attached to a lyophilization apparatus consisting of a Welch Duo-seal Vacuum Pump TM (Model No. 1402, available from Sargeant-Welch, P.O. Box 35445, Dallas, Texas 75235), a VIRTIS TM Immersion Coil Cooler (Model No. 6205-4350 Cooler in acetone bath) and a Virtis 18 Port Vacuum Drum Manifold (Model No. 6211-0350). All Virtis equipment is available from American Scientific Products, P.O. Box 1048, Grand Prairie, Texas 75050. The lyophilization drum was filled with acetone that was maintained at −50° C.

The samples were allowed to dry overnight and were then weighed on a Mettler AE 163 TM balance. The samples remaining consisted of substantially non-degradable lyophilized CARRISYN ® extract. The yield from 50 gallons of aloe vera gel was approximately 370–380 g. of CARRISYN ® extract.

EXAMPLE 11

Standard Laboratory Scale Process for Separating and Isolating CARRISYN ® extract Approximately 50 pounds of *Aloe barbadensis* Miller leaves were washed with water and brushed to remove dirt, dried latex and other contaminants. The outer cuticle of each leaf was then removed and the whole fillets were placed in a large beaker (on ice).

In 1.5 liter batches, a Waring ™ blender was loaded with the whole Aloe fillets. The fillets were blended at high speed twice, for two minutes at room temperature. The blended fillets were then cooled at 4° C. to allow foam, generated during blending, to settle.

The blended Aloe juice was then filtered through four layers of cotton (Cleveland Cotton) to remove any fibrous cellulosic pulp. The filtrate was then passed through six layers of cotton, and approximately 4 liters of Aloe juice were collected.

The Aloe juice was then placed in a large five gallon stainless steel container. To the filtered juice was added 16 liters of chilled ethanol (Fisher ™ Ethanol reagent grade, Cat. No. A995). The ethanol was added slowly while stirring the Aloe juice. A flocculent precipitate formed and the mixture was stirred for 15 to 30 minutes and was allowed to settle at room temperature for about two hours.

The supernatant was then recanted off, and the pellet was placed in a small blender to which one liter of deionized water was added. This mixture was blended for several minutes at low speed to wash the pellet and was then placed in an eight liter nalgene container. To this mixture was added four more liters of ethanol and the mixture was stirred for 30 minutes. The pricipitate that formed was allowed to settle for about two hours.

The majority of the supernatant was then decanted off and the resultant pellet was centrifuged at $2,000 \times g$ for 20 minutes at room temperature to pellet the precipitant for easy decanting of the remaining solvent.

The pellet was then placed in a lyophilization flask and lyophilized overnight in a Virtis ™ lyophilizer.

The lyophilized powder weighed 10.9 g. The percent yield was 0.273% of $2.73 \times 10^{-3}$ g/ml.

CHARACTERIZATION OF CARRISYN ® EXTRACT

From a historical perspective, *Aloe vera* has been used for centuries as a wound healer. It has also been thought to be good for gastrointestinal problems, including stomach ulcers, and to be beneficial in the treatment of arthritis. See for example, Duke, James A., CRC Handbook of Medicinal Herbs, CRC Press, Inc. Boca Raton, Florida, pp. 31, 1985; Henry, R., Cosmetics and Toiletries, An Updated Review of Aloe Vera: Allured Publishing Corp., Vol. 94, pp. 42-50, 1979; and Morton, Julia F., Folk Uses and Commercial Exploitation of Aloe Leaf Pulp: Economic Botany, Vol. 15, pp. 311-316, 1961. As noted above, however, the chemical substance in *Aloe vera* responsible for these properties of *Aloe vera* has never been identified and characterized.

Using pharmaceutical screening techniques, a polysaccharide extracted from *Aloe vera* has now been found to be the active chemical substance in *Aloe vera*. This polysaccharide will be hereinafter referred to as CARRISYN ® extract is an ordered linear polymer of substantially acetylated mannose monomers. Other ingredients, such as proteins, organic acids, anthraquinones, vitamins and amino acids make up less than one percent of CARRISYN ® extract. The concentration of CARRISYN ® extract in *Aloe vera* has been found to be approximately 0.05 to 0.3 weight-percent of the *Aloe vera* juice. The yield of concentration of CARRISYN ® extract in the leaves depends on leaf maturity.

Starting with the whole *Aloe vera* plant and using certain pharmacological models to screen for activity, the plant was systematically divided into parts. Each part was tested for pharmacological activity, and the inactive parts were discarded. Then the active parts were divided into smaller and smaller parts each time discarding the inactive fractions and keeping the active fraction until the active substance, CARRISYN ® extract, was isolated. The activity of the various fractions was measured using the stimulation of human fibroblasts in tissue culture and ulceroprotection in rats as pharmacological models.

The pharmacological data that evidences that CARRISYN ® extract is the active chemical substance in *Aloe vera* can be summarized as follows:

1. The dose-response of CARRISYN ® extract was the same as *Aloe vera* juice with an equivalent amount of CARRISYN ® extract.
2. CARRISYN ® extract was effective in the ulceroprotection model by different routes of administration, namely, intravenously, intraperitoneally and orally.
3. CARRISYN ® extract accounted for 100 percent of the effects in both pharmacological models.
4. The chemical substance, glucomannan, a substance similar to CARRISYN ® extract from a completely different source, the Konjac plant, provided some parmacological response.

CARRISYN ® extract has been shown in laboratory studies to increase up to 300% in 48 hours the replication of fibroblasts in tissue culture which are known to be responsible for healing burns, ulcers and other wounds of the skin and of the gastrointestinal lining.

CARRISYN ® extract has also been shown to increase DNA synthesis in the nucleus of fibroblasts. The increase in DNA synthesis, in turn, increases the rate of metabolic activity and cell replication, which are fundamental steps to the healing process.

CARRISYN ® extract has been shown in controlled studies to increase the rate of healing in animals.

CARRISYN ® extract has also been shown to be an effective treatment for gastric ulcers in animal studies. Over a three year period, laboratory rats, the stomachs of which react similarly to that of humans, were tested. CARRISYN ® extract was found to be equivalent to or superior to current medications used for the treatment of gastric ulcers. Most such products act to inhibit hydrochloric acid in the stomach. CARRISYN ® extract works on a different principle and does not alter the natural flow of digestive acids.

As noted above, CARRISYN ® extract can be precipitated out of liquidified *Aloe vera* gel by the addition of a water soluble, lower aliphatic polar solvent, preferably ethyl alcohol. CARRISYN ® extract powder can then be prepared by lyophilization and optionally, the lyophilization, product can be ground into a powder with a grinding apparatus such as a Moulinex ™ coffee-grinder (available from Dillard's, Dallas, Texas). CARRISYN ® extract powder is highly electrostatic and is an off-white to pinkish-purplish amorphous powder depending on the oxidization state of any anthraquinone contaminant. CARRISYN ® extract is stabilized and becomes substantially non-degradable by freeze drying or lyophilization, which removes the water which causes hydrolysis. Freeze dried *Aloe vera* gel with a given amount of CARRISYN ® extract has maintained its effectiveness for two years. It is believed that CARRISYN ® extract in freeze dried form, will be stable for up to ten years.

Heat and time have been found to be important factors in the production of powdered CARRISYN® extract. Heat can aid in the hydrolysis or degradation of CARRISYN® extract and the longer it takes to process out the CARRISYN® extract at a given temperature, the more is the degradation. Accordingly, it is preferred that the process which allows for the quickest extraction of CARRISYN® extract from whole *Aloe vera* leaves be used when high molecular weight CARRISYN® extract powder is desired and is preferred that the process which allows for the slowest extraction of CARRISYN® extract from whole *Aloe vera* leaves be used when low molecular weight CARRISYN® extract powder is desired.

Redehydration of CARRISYN® extract powder at a weight/volume concentration of 0.2 to 1 to percent resulted in the reformation of a viscous "gel" like fresh *Aloe vera*. The gel-like consistency which returns upon rehydration of CARRISYN® extract powder is indicative of the high molecular weight polysaccharide nature CARRISYN® extract. Generally, as polysaccharides are degraded or hydrolyzed their viscosity is lowered. Accordingly, the viscosity of rehydrated CARRISYN® extract powder gives a good indication of quality and may be used as a parameter for quality assurance.

CARRISYN® extract produced according to the process of the present invention may be characterized as a substantially nondegradable lyophilized ordered linear polymer of acetylated mannose monomers, preferably bonded together by $\beta(1\rightarrow4)$ bonds.

Various modifications of the disclosed compositions of the invention, as well as alternative modifications, variations and equivalents, will become apparent to persons skilled in the art upon reading the above general description. The following Examples (Examples 12-44) were conducted in order to further characterize and identify CARRISYN® extract and similar polysaccharides isolated from other Aloe species. The following examples are illustrative only and are not intended to limit the scope of the appended claims, which cover any such modifications, equivalents or variations.

EXAMPLE 12

Comparative High Performance Liquid Chromatography (HPLC)

A commercially available glucomannan (a polysaccharide isolated from the Japanese Konjac plant, purchased from General Nutrition Centers) showed some similar behavior as CARRISYN® extract in the pharmacological screening models. This Konjac mannan (henceforth called glucomannan) though utilized to aid in the characterization of the CARRISYN® extract was found to be considerably different.

Initial experiments were done on the glucomannan and the CARRISYN® extract in parallel. Both of these polysaccharides were subjected to acid hydrolysis in 1 molar (M) sulfuric acid (0.01 grams (g) polysaccharide/2 milliliters (ml) sulfuric acid) for 24 hours in vacuo at 110 degrees celsius. High Performance Liquid Chromatography (HPLC) of the hydrolyzed products (Bio Rad ™ Aminex HPX-87C Column; R.I. detector; flow rate 0.6 ml/min.; eluting solvent, HPLC grade water) showed mannose present and a peak that co-eluted with the glucose standard. The "glucose" peak was a wide, skewed peak, which indicated that it may contain modified glucose. Acid hydrolysis at slightly different concentrations gave similar results with the glucomannan yielding definite glucose and mannose products and the CARRISYN® extract yielding a definitive mannose peak and a peak that, at least migrates, with a similar retention time as the glucose standard.

The two polysaccharides were then subjected to enzymatic hydrolysis with a crude cellulase preparation. When the commercial glucomannan was hydrolyzed and analyzed by HPLC (same conditions) well resolved glucose and mannose peaks and three other peaks which migrate faster than glucose were seen. These peaks indicative of di-, tri- and tetrasaccharide moieties, were possibly due to branching of the polysaccharide or incomplete hydrolysis. Since the enzyme preparation was a semi-crude preparation, other sugar hydrolases were, no doubt, present and an accurate determination of the enzyme preparation's bond specificity could not be made. When CARRISYN® extract was subjected to the same enzymatic treatment, a very different profile was seen on HPLC. The enzymatic hydrolysis yielded mannose, glucose and at least two larger peaks corresponding to larger, unhydrolyzed oligomers. In fact, most of the polysaccharide could be found in these larger molecular fragments. This appears to be an indication that the structure (i.e., type of bonding and degree of branching) may be significantly different from the commercial glucomannan. Acid hydrolysis is a general hydrolysis method and enzymatic hydrolysis is much more specific as to the type of linkage it acts upon.

EXAMPLE 13

To aid in the characterization of CARRISYN® extract, the large polymeric saccharides were broken down through chemical hydrolysis. Hydrolysis was performed in 2N Trifluoroacetic acid solution (2N TFA) adapted from the technique developed by Albersheim, P. et al (Albersheim, P.; Nevins, D. J.; English, P. D.; and Karr, A (1967) Carbohydr. Res. 5, 340-345). The hydrolysates were vacuum oven dried and reconstituted in 0.01N $H_2SO_4$ for HPLC separation.

HPLC Separation of the Hydrolysates

Separation of the hydrolysates was performed on a Hewlett Packard ™ Liquid Chromatograph Model 1084-B. A Biorad ™ model 1770 refractive index detector was attached to the chromatograph to monitor the effluent. The separating column was an Interaction ORH-801 organic acid column which contained a 0.65×30 cm bed packed with an Interaction cation-exchange resin in hydrogen form.

The mobile phase was 0.01N $H_2SO_4$ at a flow rate of 0.5 ml/min at a temperature of 35° C. Monomeric sugars and acid standards were used to establish retention times of the chromatograms. Based on these conditions, the retention times of galacturonic acid, glucose, mannose, galactose, rhamnose and arabinose were established approximately as 7.45, 8.04, 8.69, 8.86, 9.20 and 9.78 minutes respectively.

When the hydrolysates of CARRISYN® extract samples were separated under identical conditions, some of the sugars were identified in various amounts as shown below:

TABLE 1

| Sample # | Galacturonic (Area) | Glucose (Area) | Mannose (Area) | Rhamnose | Arabinose (Area) | Acetic acid (Area) |
|---|---|---|---|---|---|---|
| Batch #1 | Trace | 476 | 14279 | — | — | 5818 |
| Batch #3 | 584 | Trace | 16926 | — | — | 4538 |
| Batch #3B | 2329 | Trace | 15068 | — | — | 5553 |
| Batch #5B | 592 | 209 | 13158 | — | — | 7888 |
| Batch #8B | 1236 | Trace | 15049 | — | — | 5392 |
| Batch #6B | Trace | 329 | 12686 | — | — | 7465 |
| C-701008 | Trace | Trace | 13734 | — | — | 6240 |
| Batch #4 | Trace | 1260 | 17800 | — | 535 | 7699 |
| Batch 8B (Dialyz) | Trace | 286 | 13715 | — | — | 6677 |
| C-613006 | Trace | Trace | 13571 | — | — | 5782 |
| *Sucrose Octa acetate | — | 2580 | — | — | — | 6407 |
| *Glucomannan (Konjac) | 441 | 10380 | 15050 | — | — | 5553 |

(*Glucommannan from the Konjac plant and sucrose octaacetate were included as reference standards.)

The liquid chromatographic separation of the hydrolysates demonstrates that CARRISYN® extract is essentially mannose. There are also varying amounts of galacturonic acid, glucose, rhamnose, arabinose and other sugars. Some of these sugars are difficult to determine accurately by this technique because of their low amount in the solution. The presence of acetyl groups as acetic acid, though in large amounts could not be completely assigned to CARRISYN® extract because the membrane filter used to clarify the hydrolysate solution appeared to add varying amounts of acetates into the chromatogram. It is noted that glucose is significantly very small in some CARRISYN® extract samples analyzed by this hydrolysis method. However, when CARRISYN® extract is hydrolyzed in mineral acids, such as H2SO4, the glucose content is much higher perhaps due to the hydrolysis of the cellulosic materials present in the extract.

The observation that CARRISYN® extract is largely mannose was also confirmed by gas chromatography/mass spectrometry (GC/MS) separation and identification of the trimethylsilane (TMS) derivatives of the hydrolysate monomers. These techniques demonstrated that mannose accounted for more than 80% of the hydrolysis product.

EXAMPLE 14

Optical Rotation

CARRISYN® extract was found to be levorotatory on the sodium D-line at 589 nanometers. A 1% (w/v) CARRISYN® extract solution in 25% methylmorpholine oxide in dimethylsulfoxide solvent gave a specific rotation at room temperature of (−) 26°. The value was measured against 25% MMNO in DMSO as the blank. The polarimeter used was Perkin Elmer™ 241 MC.

The optical rotation of aqueous solutions of CARRISYN® extract samples was determined using a Perkin-Elmer polarimeter Model 241MC. The measurements were made on a sodium line wavelength of 589 mn. The sample cell was of one decimeter (dm) pathlength. Method:

CARRISYN® extract samples totaling 200 mg were weighed accurately and placed into a 200 ml polypropylene bottle. Deionized water (18.6 Mɸ, 100 ml) was added to give a concentration of 0.2% (w/v). The suspension was allowed to agitate for 12 hours in a Lab-Line Orbit Shaker® to effect a complete dissolution (commercial glucomannan from the Konjac plant was partially dissolved).

A typical solution of CARRISYN® extract, which is usually cloudy and viscous was filtered through a 1.2 μm membrane filter (Uniflow™ #46-02360, Schliecher and Schnell Inc., Keene, NH). The filtrate was refiltered through a 0.45 μm filter (Uniflow™ #46-02340 to a clear solution. The optical rotation was measured with deionized water (18.6 MΩ) as a blank. The measured rotation angle was converted to the specific rotation as follows:

$$\alpha = [\alpha]_\lambda^t g/v$$

$$[\alpha]_\lambda^t = \alpha v/dg$$

where $[\alpha]_\lambda^t$ = specific rotation
$\alpha$ = measured rotational angle
$v$ = volume of solution (ml)
$g$ = weight (g.) of active substance in v ml of solution
$t$ = temperature (25° C.)
$\lambda$ = wavelength (589 nm)

The results are shown in Table 2.

TABLE 2

| Batch # | Specific Rotation ± S.D. |
|---|---|
| #1 | −25.9 ± 0.6 |
| #3 | −10.2 ± 0.5 |
| #4 | −21.4 ± 0.5 |
| #613006 | −14.7 ± 0.8 |
| #C701008 | −12.7 ± 0.4 |
| #3B | −14.2 ± 0.7 |
| #5B | −9.5 ± 0.2 |
| Glucomannan | −19.0 ± 0.4 |

The optical rotation demonstrates that CARRISYN® extract is levorotatory. The degree of rotation may vary from batch to batch.

All of the above data indicate that CARRISYN® extract is a polymer having a β(1→4) bond linkage.

EXAMPLE 15

Elemental Analysis

Elemental analysis of organic compounds is a powerful tool in structure elucidation. CARRISYN® extract is substantially organic in nature and therefore amenable to this technique. Sample batches of CARRISYN® extract were sent to Huffman Laboratories Incorporated in Wheat Ridge, Colorado for elemental analyses. Oxygen, carbon, hydrogen, and nitrogen accounted for 80–90% of the make up of CARRISYN® extract. Phosphorus and sulfur together accounted for 0.5–2%. Table 3 illustrates the reported results.

TABLE 3

| Sample # | Carbon | Hydrogen | Elements Oxygen | % Nitrogen | Sulfur | Phosphorus |
|---|---|---|---|---|---|---|
| Batch #1 | 37.62 | 5.71 | 45.85 | 1.27 | 0.31 | 0.61 |
| Batch #2 | 30.33 | 4.67 | 45.16 | 1.15 | 0.34 | 0.74 |
| Batch #3 | 29.58 | 4.23 | 44.30 | 0.46 | 0.28 | 0.33 |
| Batch #4 | 39.86 | 5.84 | 46.43 | 0.52 | 0.16 | 0.60 |
| Batch #5 | 37.45 | 5.76 | 46.29 | 0.81 | 0.18 | 0.68 |
| Batch #6 | 41.72 | 6.11 | 46.14 | 0.84 | <.30 | 0.48 |
| Batch #7 | 39.20 | 5.66 | 45.40 | 1.36 | <.30 | 0.54 |
| Hilltop | 36.45 | 5.35 | 44.07 | 1.51 | 0.44 | 1.02 |
| Mithcell | 41.57 | 5.96 | 43.25 | 1.35 | 0.37 | 0.71 |
| TCX | 33.47 | 5.03 | 44.53 | 1.57 | 0.46 | 1.25 |

It is significant that for batches #3, #4, #5 and #6, the nitrogen content was comparatively low. These batches were prepared from denatured alcohol. Their physical appearance was also different from the majority of the CARRISYN® extract samples. Moreover, the cell culture responses (human fibroblast stimulation) of these batches were comparatively lower than the average.

EXAMPLE 16

Emission Spectrographic Analysis

Emission spectrographic analysis was performed on CARRISYN® extract samples. The analysis was performed by Huffman Laboratories Inc. in Wheat Ridge, Colorado. A total of 68 elements from silver (Ag) to zinc (Zn) was monitored. Only a few of the elements were detected. These were calcium, sodium, silicon, magnesium, manganese, copper, chromium, barium, iron, and aluminum. Environmental Protection Agency (EPA) listed toxic metals such as lead, molybdenum, cobalt, cadmium, arsenic, selenium, and mercury, among others, were not detected by this technique which is semiquantitative.

EXAMPLE 17

X-ray diffraction Analysis

The powder X-Ray diffraction pattern of CARRISYN® extract obtained using a Philip Electronic Instrument X-Ray diffraction unit. A range of 5°-60° [degrees] two-theta (2 $\theta$) angle was scanned at the rate of (2 $\theta$) angle per minute. The radiation was Copper K$\alpha$ (CuK$\alpha$) from a tube operated at 15 milliamperes and 35 kilovolts.

Most CARRISYN® extract samples examined by X-ray diffraction analysis demonstrated no appreciable crystallinity. CARRISYN® extract was essentially amorphous. The amorphous nature of CARRISYN® extract can be destroyed by deacetylation and slightly by air drying of a rehydrated form.

EXAMPLE 18

Thermogravimetric Analysis

This technique measures change in loss of weight with temperature. Both laboratory prepared and large scale manufactured CARRISYN® extract samples were analyzed by using a Mettler Thermogravimetric Analyzer TA 3000 ™ system. The system was composed of a TC 10A TA processor and a TG 50 thermobalance. The temperature range was ambient [25° C.] to 750° C.

CARRISYN® extract demonstrated a simple decomposition pattern inferring a possible simple structure. The decomposition profile differed from that of glucomannan from the Konjac plant. CARRISYN® extract lost surface and bound water between 50° C.-210° C. with the main peak at 95° C. The bulk of the decomposition took place between 210°-405° C. with a peak near 325° C. More decompositions occurred between 406° C.-735° C. The oxidizable carbons were eliminated from 630° C.-737° C. The residue of largely ash accounted for more than 10-20% of the total weight. Table 4 illustrates the thermogravimetric decomposition profile of several samples of CARRISYN ™.

TABLE 4

| Sample # | Sample (mg) | H$_2$O % | Decompositions % Total wt. | | | Oxidizable % | Residue % |
|---|---|---|---|---|---|---|---|
| | | | 1 | 2 | 3 | | |
| 606005 | 6.53 | 9.35 | 49.66 | 11.59 | 6.03 | 16.4 | 7.70 |
| 711009 | 5.60 | 6.55 | 40.08 | 11.49 | 5.50 | 19.09 | 18.74 |
| 430003 | 8.24 | 9.33 | 36.43 | 10.76 | 4.60 | 24.69 | 18.65 |
| 620007 | 10.17 | 10.25 | 38.21 | 10.27 | 3.62 | 25.68 | 17.83 |
| 701008 | 5.79 | 9.65 | 45.10 | 10.55 | 5.09 | 13.43 | 17.25 |
| 531004 | 4.96 | 8.92 | 48.94 | 11.14 | 6.38 | 11.98 | 13.98 |
| 613006 | 4.86 | 8.16 | 46.3 | 10.75 | 5.40 | 15.41 | 16.38 |
| Mex. 4 ply | 8.03 | 8.46 | 26.04 | 11.55 | 3.46 | 31.61 | 25.84 |
| Man. Batch 1 | | 9.22 | 58.2 | 12.70 | 4.70 | 3.52 | 10.74 |
| Man. Batch 2 | 7.96 | 12.81 | 37.63 | 10.16 | 6.84 | 15.28 | 18.97 |
| Acetyl. 531004 | 7.74 | 5.45 | 66.94 | 6.89 | 3.69 | 15.0 | 2.51 |
| Glucomannan from Konjac. | 30.6 | 9.82 | 11.32 | 60.83 | 0 | 17.4 | 0.668 |

It was observed that the decomposition profile was nearly the same, irrespective of the source of the aloe leaves from which the CARRISYN® extract sample was made. The profile was significantly different from glucomannan of the Konjac plant. The manufactured batch #1 did portray some differences. This was not surprising because it was produced by a markedly different process. The precursor gel was filtered clear through a diatomaceous earth filter before CARRISYN® extract was precipitated from the gel with alcohol.

EXAMPLE 19

Density

The density of CARRISYN® extract may vary depending on the amount of inorganic salts which co-precipitated with the CARRISYN® extract.

The density of CARRISYN® extract is also highly dependent on hydration. By adding additional water to the product prior to lyophilization, a fluffier, less dense product is produced. To maintain consistency the following samples were produced by a standard method using a ratio of 4:1 ethanol to water v/v during their manufacture, prior to freeze-drying.

Procedure

Dry CARRISYN® extract powder was added to a preweighed 10 ml graduated cylinder, then the cylinder was weighed again to determine the total amount of CARRISYN® extract added. All weights were measured on a Mettler ™ AE 163 analytical balance. The cylinder was then agitated on a Vortex-Genie ™ agitator for 10 seconds on the highest speed, then the volume of CARRISYN® extract was observed. The density was determined as mass (grams) per volume (milliliters) of the dry CARRISYN® extracts powder.

The results are shown in Table 5.

TABLE 5

| Batch | Density |
|---|---|
| #1 | 0.074 |
| #3 | 0.640 |
| #4 | 0.382 |
| #613006 | 0.158 |
| #701008 | 0.291 |
| #3B | 0.561 |
| #5B | 0.759 |
| #6B | 0.626 |
| #7B | 0.683 |
| #8B | 0.499 |
| Glucomannan | 0.596 |

One gram of dry CARRISYN® extract powder from Batch #5B was dissolved in 50 ml of deionized water. The solution was then lyophilized. The dry CARRISYN™ was a fluffy white powder having a density of 0.110. Thus, by redissolving the CARRISYN® extract from Batch #5B in 50 ml. of water and then lyophilizing the solution, the density of the dry powder went from 0.759 to 0.110.

EXAMPLE 20

Solubility of CARRISYN® Extract

CARRISYN® extract demonstrates varying solubility characteristics which depend largely on the source of the aloe leaf, the degree of processing such as filtration, ethanol precipitation and drying. Degrees of aqueous solubilities of different batches of CARRISYN® extract have been observed. The same concentration (wt/volume) of different CARRISYN® extract batches may produce aqueous solutions (sols) very much different in viscosities and inorganic salt content. Viscosity and inorganic salt content generally affect the extent of solubilization of a material.

The present study was done with CARRISYN® extract Manufactured Batch #1 and Batch #2. The two batches have some differences in both source, processing and some chemical composition. Solubilities in water and other media may differ. The solvents used were water, acetone, dimethylsulfoxide (DMSO), Tetrahydrofuran (THF), 0.9% sodium chloride and 0.1% sodium benezoate.

Method

A total of 18 polypropylene tubes were set up. Six for each CARRISYN® extract batch and the remaining six tubes were for solvent blanks.

Into each of the sample tubes, 0.04 grams of CARRISYN® extract was weighed and added. Ten milliliters (10 ml.) of the solvent was added producing a 0.4% (wt./volume) mixture. The mixture was subjected to agitation for 5 hours at room temperature. The suspension was transferred to centrifuge tubes and centrifuged for 50 minutes at 1,500 rpm. The solvent blanks were similarly treated.

The solutions were decanted from the solids. Both the solutions and the solids (deposits) were dried in an oven at low heat <50° C. until completely dried. The dried solids were weighed. The solvent flasks that showed deposits were also weighed. This weight was subtracted from the weight of the samples.

TABLE 6.

| Solvent | Batch No. | Decanted Solution (gm/100 ml.) | Deposit (gm/100 ml.) | Total (gm/100 ml) |
| --- | --- | --- | --- | --- |
| water(H$_2$O) | 1 | 0.338 | 0.080 | 0.418 |
| | 2 | 0.384 | 0.035 | 0.419 |
| acetone | 1 | 0.0 | 0.365 | 0.365 |
| | 2 | 0.0 | 0.353 | 0.353 |
| dimethylsulphoxide | 1 | 0.282 | 0.125 | 0.407 |
| | 2 | 0.202 | 0.208 | 0.410 |
| tetrahydrofuran | 1 | 0.04 | 0.358 | 0.398 |
| | 2 | 0.04 | 0.351 | 0.391 |
| 0.9% sodium chloride | 1 | 0.376 | 0.041 | 0.417 |
| | 2 | 0.418 | 0.019 | 0.437 |
| 0.1% sodium benzoate | 1 | 0.354 | 0.083 | 0.437 |
| | 2 | 0.342 | 0.026 | 0.368 |

Results

CARRISYN® extract was more soluble in water and aqueous solutions than any other solvent tested.

The concentration 0.4% (wt./volume) was chosen as a comprise between high viscosity in aqueous medium and very low solubility of CARRISYN® extract in other solvents. It is possible to get more CARRISYN® extract dissolved in water to about 0.5% (w/v).

EXAMPLE 21

Viscosity

Viscosity measurements were made using a Cannon-Fenske™ type viscometer (Model 150, Industrial Research Glassware Ltd., Union, NJ) at 40° C. Aqueous CARRISYN® extract 0.2% solutions (0.05% NaN$_3$) were loaded into a viscometer and allowed to warm for ten minutes in a water bath (Model SBG-1090, Blue M Electric Co., Blue Island, IL). The solution flow was then observed to the nearest 0.1 second according to the manufacturer's directions. The calibration factor was 0.04197 centistokes/sec. at 40° C.

The results are shown in Table 7.

TABLE 7

| Batch # | Viscosity (CentiStokes) |
| --- | --- |
| #1 | 6.10 |
| #3 | 1.18 |
| #4 | 5.09 |
| #613006 | 2.12 |
| #C701008 | 2.08 |
| #3B | 2.02 |
| #5B | 4.53 |
| #6B | 1.75 |
| #7B | 1.55 |
| #8B | 1.97 |

EXAMPLE 22

Calcium Concentrations

Although the function of calcium in *Aloe vera* activities is not completely established, the quality of *Aloe vera* gel is at times based on the calcium and magnesium content. Since CARRISYN® extract is the active substance in *Aloe vera* gel, the calcium content was monitored.

The total calcium in CARRISYN® extract was determined spectrophotometrically using a Calcium Rapid Stat Kit™ (Lancer Medical, St. Louis, MO). 50 μl samples of aqueous 0.2% CARRISYN® extract solutions (0.05% NaN$_3$) were added to 3.0 ml of reagent, and the blue calcium-methylthymol complex was observed at 612 nm using an IBM Model 9420 UV-Visible Spectrophotometer.

Bound calcium was determined by the following empirical procedure: 25 ml samples of aqueous 0.2% CARRISYN® solutions (0.05% NaN$_3$) were placed in dialysis bags and dialyzed against 10 liters of 18.6MΩ deionized water overnight at room temperature. The contents of the bags were then transferred to lyophilization jars and freeze-dried. The dry powders were weighed, then digested overnight in 20% nitric acid, 10% hydrochloric acid solution at 80° C. The samples were sent to Trac Laboratories in Denton, Texas for the determination of calcium by atomic absorption spectroscopy. Note: All containers in the above procedure were made of Nalgene or polypropylene, and had been extensively washed with 1.0 M HCl and deionized water (18.6MΩ).

The results are shown in Table 8.

TABLE 8.

| Batch | Total Calcium (% Dry CARRISYN ® Extract | Bound Calcium CARRISYN ® Extract | Weight (mg) of lyophilized solids |
|---|---|---|---|
| #1 | 3.7 | 0.042 | 31.7 |
| #3 | 10.15 | 0.066 | 12.9 |
| #4 | 2.15 | 0.048 | 32.0 |
| #613006 | 6.85 | 0.060 | 20.6 |
| #C701008 | 6.65 | 0.068 | 23.9 |
| #3B | 6.50 | 0.074 | 20.7 |
| #5B | 3.55 | 0.074 | 29.6 |
| Glucommannan | | negligible | |

EXAMPLE 23

Nuclear Magnetic Resonance Spectroscopy (NMR)

NMR is a powerful technique that is indispensable in molecular structure elucidation. NMR spectra are calibrated using reference standards (tetramethylsilane, etc.) for chemical shift. Because of the inherent low solubility and high viscosity of CARRISYN ® extract in some solvents generally used in NMR spectroscopy ($D_2O$, DMSO, Acetone-D, etc.) the technique has not been successful in CARRISYN ® extract solutions.

However, excellent spectra of CARRISYN ® extract as a solid, were obtained with a Cross Polarization-Magic Angle Spinning (CP-MAS) techniques. A solid phase CARRISYN ® extract C-13 NMR spectrum was obtained. The spectrum was produced by an IBM Spectrometer, with some special accessories attached to the IBM NMR spectrometer. Based on the spectrum, the C-13 NMR peaks of CARRISYN ® extract analyzed were located at 20.54, 60.39, 71.33, 100.75, 171.78 and 180.75 parts per million (ppm) chemical shift with tetramethylsilane (TMS) as an external reference standard.

Tentatively, these peaks are assigned as follows: 20.54 ppm (CH3COH) or (CH3CO2); 60.39 (CH3O, CH2OH); 71.35 for C-2, C-3, C-4 and C-5 carbons. This assignment is perhaps correct in view of the size of this particular peak. The peak at 100.75 ppm may be due to (C-1 glycosidic). The 171.78 peak is slightly lower than is expected for COOH but may be dependent on the orientation of the molecule. The last peak at 180.75 ppm is a carbonyl carbon (C=O). Some small peaks about 95 ppm corresponding to C-1 (reducing end) were also observed. Significantly absent are any peaks between 106-109 ppm which may indicate C-1 of furanosyl unit.

These assignments are consistent with the structure of a $\beta(1\rightarrow 4)$ mannan.

EXAMPLE 24

Infrared Spectroscopy

Infrared spectroscopy has been effective in the identification and characterization of CARRISYN ® extract. An IBM ™ IR/32 Fourier Transform Infrared spectrometer was used for this technique. The instrument is self calibrating to wave length by software and a He-Ne laser, which can be verified by a standard spectrum of polystyrene film. Optical alignment is occasionally required when the signal to noise ratio decreases.

CARRISYN ® extracted is ground to a powder and mixed with an infrared grade potassium bromide [KBr] powder. The mixture may be pressed into a transparent disc which is scanned over infrared light. A new technique has been developed of making transparent films of 0.2% [w/v] aqueous CARRISYN ® which demonstrates better spectrum resolution than KBr discs. When CARRISYN ® extracted was scanned from 4000-400 $cm^{-1}$, the following functional groups were observed in the spectrum: 3600-3200 $cm^{-1}$ due to the stretching frequency [O—H] hydrogen bonded and the related 1100-1050 $cm^{-1}$ bending vibration. The stretching vibration at 2950-2800 $cm^{-1}$ and the corresponding bending frequency 1470-1460 $cm^{-1}$ were C—H groups. The other observed major functional groups were: [1] The $COO^-$ unit whose asymetric and symmetric vibrations were located between 1600-1550 $cm^{-1}$ and 1450-1400 $cm^{-1}$, respectively.

[2] The ester groups [COOR] whose stretching vibration frequencies were observed between 1746-1735 $cm^{-1}$ and 1250-1240 $cm^{-1}$.

[3] The amide groups [CONH] whose Amide I stretch and Amide II bending vibration were located near 1650-1645 and 1550-1540 $cm^{-1}$, respectively. Table 9 is included here to illustrate approximate frequencies [wave numbers], the corresponding functional group and the vibration mode.

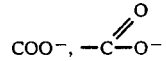

TABLE 9

| Peak # | Wavenumber ($cm^{-1}$) | Functional Group | Vibrational Mode |
|---|---|---|---|
| 1 | 1100-1035 | O—H, C—O—C | v (O—H) |
| 2 | 3430-3390 | O—H | v (O—H) |
| 3 | 2930-2800 | C—H | v (C—H) |
| 4 | 1470-1380 | C—H | σ (C—H) |
| 5 | 1600-1550 | $COO^-$, $-C(=O)-O^-$ | v (C=O) assy. |
| 6 | 1450-1400 | | v (C=O) sym |
| 7 | 1420-1410 | C—O | |
| 8 | 1650-1645 | CONH | v Amide I C=O |
| 9 | 1550-1540 | CONH | v Amide II |
| 10 | 1746-1735 | COOR | v (C=O) |
| 11 | 1250-1240 | COOR | v (C—O—C) |
| 12 | 980-950 | C—, O—CH2 | |

Table 10 is presented below to demonstrate how the peak absorption maximum of various CARRISYN ® extract samples match Table 9 peak assignments.

TABLE 10

| CARRISYN ® Extract 531004 [$cm^{-1}$] | CARRISYN ® Extract Hilltop [$cm^{-1}$] | CARRISYN ® Extract Batch #2 [$cm^{-1}$] |
|---|---|---|
| 1591.5 | 1068.7 | 1585.7 |
| 3414.4 | 1037.8 | 3400.9 |
| 1072.6 | 3420.2 | 1086.1 |
| 1246.2 | 1244.2 | 1425.6 |
| 1740.0 | 1734.2 | 1037.8 |
| 1431.4 | 1635.8 | 1244.2 |
| 603.8 | 1653.2 | 1740.0 |
| 2930.2 | 1375.4 | 605.7 |
| 806.3 | 472.6 | 679.0 |
| | 1419.8 | 2928.3 |
| | 1558.7 | 545.9 |
| | 605.7 | 956.8 |
| | 2924.4 | 806.3 |
| | | 879.6 |

Based on the infrared analysis, CARRISYN ® extract is perhaps a polydisperse heteropolysaccharide with some acid, ester [O-acyl/N-Acyl] functional group side chains. CARRISYN ® extract samples have been fully O-acetylated and also deacetylated. The carbonyl functional group and the C—O—C stretches of acetylated CARRISYN® extract samples were observed between 1748-1735 cm$^{-1}$ and 1246-1235 cm$^{-1}$, respectively. The carboxylate carbonyl stretches of deacetylated CARRISYN® extract sample were located between 1600-1550 cm$^{-1}$ and 1450-1400 cm$^{-1}$, respectively as follows:

TABLE 11

| CARRISYN® Extract 531004 cm$^{-1}$ | CARRISYN® Extract 531004 [Deacetylated] cm$^{-1}$ | CARRISYN® Extract 531004 [Acetylated] cm$^{-1}$ |
|---|---|---|
| 1591.5 | 1431.4 [1560-1339] | 1244.2 |
| 3414.4 | 3400.9 | 1741.9 |
| 1072.6 | 1032.0 | 1064.8 |
| 1246.2 | 1062.9 | 3460.7 |
| 1740.0 | 1091.8 | 1375.4 |
| 1431.4 | 875.8 | 1647.4 |
| 603.8 | 1147.8 | 1433.3 |
| 2930.2 | 1645.5 | 2932.2 |
| 806.3 | 2924.4 | 1541.3 |
|  | 814.1 | 956.8 |
|  | 615.4 | 603.8 |

When CARRISYN® extract was deacetylated, the absence of the ester C—O—C stretch frequency between 1248-1235 cm$^{-1}$ was observed. It was also noticed that the largest peak of the spectrum was centered at 1431 cm$^{-1}$. The degree of acetylation/deacetylation of CARRISYN® extract may be monitored by these two peaks. Actually, for this particular example, the peak at 1431 cm$^{-1}$ [1560-1339 cm$^{-1}$] was contaminated by an amide II peak since amide I could be observed at about 1646 cm$^{-1}$.

EXAMPLE 25

Biological Activity

It has been observed by both in vivo and in vitro experiments that CARRISYN® extract promotes the proliferation of fibroblast cells. Promotion by a factor of 2-3 over the control has occasionally been recorded. Table 12 illustrates fibroblast proliferation counts influenced by CARRISYN® extract at a concentration of 0.1% (w/v) over a 72 hour period.

TABLE 12

| Sample # | Conc. % (w/v) | 24 hrs. % | 48 hrs. % | 72 hrs. % |
|---|---|---|---|---|
| TCX Lab. 7/25/85 |  | 0.1 | 90.7 | 162.2 |
| 163.8 |  |  |  |  |
| Batch 1 (TCX) | 0.1 | 104.3 | 139.7 | 129.5 |
| Batch 2 | 0.1 | 72.1 | 123.2 | 144.9 |
| Batch 3 | 0.1 | 75.5 | 130.9 | 128.4 |
| Batch 4 | 0.1 | 102.3 | 131.2 | 135.1 |
| Batch 5 | 0.1 | 79.3 | 115.0 | 129.2 |
| Batch 6 | 0.1 | 57.7 | 130.9 | 113.3 |
| Batch 7 | 0.1 | 65.1 | 110.6 | 120.2 |
| Batch (Lab.) 5/83 | 0.1 | 81.1 | 138.3 | 169.7 |
| Man. Batch 1 B | 0.1 | 125.6 | 174.8 | 114.8 |
| Man. Batch 2 B | 0.1 | 103.5 | 175.3 | 118.6 |
| Man. Batch 3 B | 0.1 | 138.9 | 156.4 | 147.0 |
| Man. Batch 3 B(Hydrate) | 0.1 | 103.3 | 141.3 | 158.9 |
| Glucomannan(Konjac plant) | 0.1 | 103.3 | 69.9 | 108.6 |
| Control SCM | 0.1 | 100.0 | 100.0 | 100.0 |

These experiments were conducted to evaluate the cell response to different samples of CARRISYN® extract prepared under various conditions.

EXAMPLE 26

Acetyl Group Analysis

The amount of O-acetyl groups in a series of different CARRISYN® extract batches was determined. Prior to analysis, the samples had been dried overnight in a vacuum oven at 40° C. over P$_2$O$_5$. Solutions were then made of approximately 1 mg/ml in deionized water. The analytical procedure used was the same as that described by Hestrin (Shlomo Hestrin, J. Biol. Chem. (1949), 180, 249-261) involving the colorimetric observation of the ferric-acethydroxamic acid complex.

The results are as follows:

TABLE 13

| Sample | mMoles acetyl groups Per gram CARRISYN® Extract |
|---|---|
| 1 | 3.72 |
| 3 | 1.30 |
| 4 | 4.15 |
| 3B | 2.11 |
| 4B | 0.23 |
| 5B | 3.33 |
| 6B | 2.28 |
| 8B | 2.32 |
| 10B | 1.68 |
| 531004 | 2.97 |
| 613006 | 2.77 |
| 701008 | 2.61 |
| peracetylated(531004) | 5.69 |
| 8B >100K | 3.93 |
| 8B 10K <100K | 2.98 |
| 3B 3K <10K | 0.10 |
| 3B <3K | ND |
| methylated 8B | ND |

A table of relative activity values (fibroblast stimulation) and acetylation for eight 0.1% CARRISYN® extract solutions at 72 hours measured on the same day follows below.

TABLE 14

| Batch # | mMoles O-acetyl groups Per gram CARRISYN® Extract | % Activity |
|---|---|---|
| 613006 | 2.7700 | 136.0000 |
| 701008 | 2.6100 | 95.5000 |
| 1 | 3.7200 | 113.2000 |
| 3 | 1.3000 | 93.9000 |
| 4 | 4.1500 | 104.7000 |
| 3B | 2.1100 | 111.7000 |
| 4B | 0.2300 | 74.4000 |
| 5B | 3.3300 | 100.7000 |

The data suggest a trend that CARRISYN® extract activity is directly proportional to the amount of O-acetyl groups per gram of CARRISYN® extract. This was a surprising and unexpected result.

A table of viscosity value (in centistokes) and acetylation for nine CARRISYN® extract samples follows below:

TABLE 15

| Batch # | mMoles acetyl groups Per gram CARRISYN® Extract | Viscosity (CentiStokes) |
|---|---|---|
| #1 | 3.7200 | 6.1000 |
| #3 | 1.3000 | 1.1800 |
| #4 | 4.1500 | 5.0900 |
| #613006 | 2.7700 | 2.1200 |
| #701008 | 2.6100 | 2.0800 |
| #3B | 2.1100 | 2.0200 |
| #5B | 3.3300 | 4.5300 |
| #6B | 2.2800 | 1.7500 |
| #8B | 2.3200 | 1.9700 |

This data shows that viscosity is exponentially proportional to the degree of acetylation of CARRISYN® extract. Viscosity can be used as a quality control measure for CARRISYN® extract. From the above data the following line of best fit was determined:

Viscosity = $0.496 \times e$ $(0.604 \times mMoles\ acetyl\ groups/g.)$

EXAMPLE 27

The following experiments were conducted with aloe leaves from Hill Top Gardens, Harlingen, Texas. The leaves were processed by washing, cutting, filleting, grinding, homogenization (1500 psi) and filtration (pulp filter media). The entire processing was completed in less than one hour and 20 minutes.

PART I

At 9:10 a.m., 3 liters of gel and 12 liters of 190 proof undenatured ethanol were mixed vigorously in a 5 gallon polypropylene bottle. This process was carried out, in duplicate, for a total of 6 liters of gel and 24 liters of ethanol. Five liters of the mixture were quickly transferred into each of the 5 stainless steel pans labeled 1 hr., 2 hrs., 4 hrs., 8 hrs., and 10 hrs., respectively. Another pan was included for 24 hrs. study.

After 1 hour from the time alcohol was added for example, the sample labelled 1 hour was concentrated by siphoning out the alcohol followed by centrifugation. The solid was washed in fresh alcohol which was decanted after centrifugation. The solid precipitation was placed in a lyophilizer bottle, quickly frozen in liquid nitrogen and set to lyophilize. The process of removal of alcohol to the lyophilization step took an average of 50-60 minutes. Each labeled fraction was similarly treated.

TABLE 16

For Part 1 Study

| Sample # (hours) | Time | Time(put in lyophilizer) | Dry Weight (gram) | Yield (gram/Liter) | Percent Yield (W/V) |
|---|---|---|---|---|---|
| 1 | 10:10 a.m. | 11:15 a.m. | .7176 | .7176 | .0718 |
| 2 | 11:10 a.m. | 12:10 p.m. | .7643 | .7643 | .0764 |
| 4 | 1:10 p.m. | 2:15 p.m. | .7748 | .7748 | .0775 |
| 8 | 5:10 p.m. | 6:10 p.m. | .7903 | .7903 | .0790 |
| 10 | 7:10 p.m. | 7:40 p.m. | .8147 | .8147 | .0815 |
| 24 | 9:10 a.m. | 10:05 a.m. | .9373 | .9373 | .0937 |

PART II

Part II study was different from Part I by the fact that pure aloe gel was subjected to the time study. At the time X hours (X=0, 1, 2, 4, 8 and 10 hours respectively). Two liters of pure gel were mixed with 8 liters of 190 proof undenatured alcohol. The mixture was agitated and allowed to settle for 4 hours before the alcohol would be removed by siphoning and centrifugation. The solid precipitate was treated as previously described in Part I.

TABLE 17

For Part II Study

| Sample # (hrs) | 0 | 1 | 2 | 4 | 8 | 10 |
|---|---|---|---|---|---|---|
| Time | 9:10 am | 10:10 am | 11:10 am | 1:10 pm | 5:10 pm | 7:10 pm |
| Time(to Remove Alcohol | 1:10 pm | 2:10 pm | 3:10 pm | 5:10 pm | 9:10 pm | overnight |
| Time(hrs in Alcohol | 4 | 4 | 4 | 4 | 4 | — |
| Time (into | 2:20 pm | 3:10 pm | 4:10 pm | 6:15 pm | 9:35 pm | — |

TABLE 17-continued

For Part II Study

| Sample # (hrs) | 0 | 1 | 2 | 4 | 8 | 10 |
|---|---|---|---|---|---|---|
| Lyophilizer Dry Weight (gram) | 1.4894 | 1.4752 | 1.4083 | 1.3443 | 1.4957 | 1.3324 |
| Yield (gram/liter) gel | .7447 | .7376 | .7042 | .6722 | .7478 | .6662 |
| Yield Percent (W/V) | .0745 | .0738 | .0704 | .0672 | .0748 | .0666 |

TESTS ON TIME LAPSE STUDY CARRISYN® EXTRACT

Size Exclusion Chromatography (SEC)

The average molecular weight distribution of CARRISYN® extract was determined by size exclusion Chromatography (SEC). The liquid Chromatograph was a Hewlett Packard TM Model 1084 B featuring an HP 79875 A UV-VIS detector, an autosampler 79841 A and a Biorad TM Model 1770 refractive index detector. The column was a Beckman prepacked column 7.5×300 mm packed with spherogel-TSK 2000 sw; part no. 244282, serial no. 5K526. The mobile phase was 0.05% (w/v) sodium azide solution with a flow rate of 0.5 ml/min at a temperature of 30° C. dextran standards from Sigma Chemical Company, St. Louis, Missouri were used to establish the average molecular weight distribution as follows:

| Dextran # | Lot # | Ave. M.W. | Retention Time (mins.) |
|---|---|---|---|
| D-5376 | 24F-0298 | 2,000,000 | 11.21 |
| D-1390 | 13F-0427 | 71,200 | 11.49 |
| D-4133 | 114F-0335 | 40,600 | 11.84 |
| D-9260 | 53F-0240 | 9,000 | 17.71 |

Applying the same conditions for the CARRISYN® extract separation, three major peaks were observed as follows:

| HILLTOP (freeze dried) FILLET: | | | |
|---|---|---|---|
| Fraction # | Ret.(min) | % Total | % (3 Fractions) |
| 1 | 10.87 | 10.20 | 12.2 |
| 2 | 16.38 | 17.73 | 21.1 |
| 3 | 22.48 | 56.02 | 66.7 |
| HILLTOP INSTANT PROCESS (Fast): | | | |
| Fraction # | Ret.(min) | % Total | % (3 Fractions) |
| 1 | 11.85 | 43.14 | 46.8 |
| 2 | 16.57 | 19.74 | 21.4 |
| 3 | 22.05 | 29.24 | 31.7 |
| HILLTOP Part I (1 hour): | | | |
| Fraction # | Ret.(min) | % Total | % (3 Fractions) |
| 1 | 11.52 | 50.30 | 54.6 |
| 2 | 16.28 | 14.04 | 15.2 |
| 3 | 21.99 | 27.71 | 30.1 |
| HILLTOP Part 2 (4 hours): | | | |
| Fraction # | Ret.(min) | % Total | % (3 Fractions) |
| 1 | 11.79 | 56.42 | 58.3 |
| 2 | 16.33 | 15.30 | 15.8 |
| 3 | 21.98 | 25.07 | 25.9 |
| HILLTOP Part 1 (10 hours): | | | |

-continued

| Fraction # | Ret.(min) | % Total | % (3 Fractions) |
|---|---|---|---|
| 1 | 11.14 | 57.73 | 60.4 |
| 2 | 16.37 | 14.66 | 15.5 |
| 3 | 22.03 | 22.44 | 23.7 |

HILLTOP Part 1 (24 hours):

| Fraction # | Ret.(min) | % Total | % (3 Fractions) |
|---|---|---|---|
| 1 | 11.41 | 45.75 | 50.5 |
| 2 | 16.55 | 19.35 | 21.4 |
| 3 | 21.28 | 25.43 | 28.1 |

When CARRISYN® extract samples made earlier were separated under the same conditions as the above, three major fractions were also observed.

TCX MANUF. Batch #1

| Fraction # | Ret.(min) | % Total | % (3 Fractions) |
|---|---|---|---|
| 1 | 11.18 | 35.18 | 36.98 |
| 2 | 16.12 | 7.04 | 7.40 |
| 3 | 22.29 | 52.91 | 55.60 |

MEXICO Manuf. Batch #2

| Fraction # | Ret.(min) | % Total | % (3 Fractions) |
|---|---|---|---|
| 1 | 11.04 | 19.02 | 19.0 |
| 2 | 16.46 | 24.27 | 24.3 |
| 3 | 22.38 | 56.70 | 56.7 |

Based on the dextran standard, the average molecular weight distribution of the 3 fractions of CARRISYN® extract were as follows:

Fraction
1 > 80,000
2 ≧ 10,000
3 < 1,000

Only the average molecular weight distribution can be determined since dextrans and the polysaccharides of CARRISYN® extract may be physically and chemically different. For example, size separation may be influenced by other factors such as ionic charge, adsorption and/or partition between the solvents.

CALCIUM CONTENT OF CARRISYN® EXTRACT

Although, the function of calcium in aloe activities is not completely established, this parameter is still monitored in CARRISYN® extract. The calcium content of CARRISYN® extract was determined by The Lancer calcium Rapid Stat Kit which is generally used for the quantitative colorimetric determination of calcium in serum and urine. The deep blue calcium methylthymol blue complex formed is read at 612 nanometers. For this example, IBM UV/VIS spectrophotometer model 9420 was used to monitor the absorbance. Based on 3 point Calcium standard, the calcium content of CARRISYN® extract was determined as follows:

Part I

| Sample # (hours in alcohol) | % Calcium (w/w) |
|---|---|
| 0 | N/A |
| 1 | 4.58 |
| 2 | 5.03 |
| 4 | 5.06 |
| 8 | 5.06 |
| 10 | 5.39 |
| 24 | 5.40 |

Part II

| Sample # (hours before alcohol) | % Calcium (w/w) |
|---|---|
| 0 | 4.26 |

-continued

| | |
|---|---|
| 1 | 4.00 |
| 2 | 4.55 |
| 4 | 4.48 |
| 8 | 4.69 |
| 10 | 4.04 |

INFRARED ANALYSIS

Infrared (IR) Spectroscopy as an analytical technique is especially important in the analysis of CARRISYN® extract whose viscosity in aqueous medium presents problems in any analysis requiring a solution.

Infrared analysis was carried out on CARRISYN® extract to monitor the functional groups. The instrument used was an IBM ™ Fourier Transform-Infrared (FT-IR) spectrometer model 32. The system status was, resolution=4; number of scans=32; detector=DTGS.

Since CARRISYN® extract is a powder, it can be easily mixed with infrared grade potassium bromide (KBr) powder and the mixture pressed into a disc. The disc is then scanned. However, a new technique of making transparent films of 0.2% (w/v) aqueous CARRISYN® extract has been developed. The film gives a better infrared spectrum of CARRISYN® extract than the KBr disc technique. When CARRISYN® extract was scanned from 4000 cm$^{-1}$ to 400 cm$^{-1}$; the following characteristic absorption frequencies were observed:

TABLE 18

| Peak # | Wave # (cm$^{-1}$) | Functional Group | Vibrational Mode |
|---|---|---|---|
| 1 | 1100-1035 | O—H, C—O—C | σ (O—H) |
| 2 | 3430-3390 | O—H | ν (O—H) |
| 3 | 2930-2800 | C—H | ν (C—H) |
| 4 | 1470-1380 | C—H | σ (C—H) |
| 5 | 1600-1550 | COO$^-$, C(=O)(O$^-$) | ν (C=O) assym. |
| 6 | 1450-1400 | | ν (C=O) sym |
| 7 | 1420-1410 | C—O | |
| 8 | 1650-1645 | CONH | Amide I C=O |
| 9 | 1550-1540 | CONH | Amide II σ (N—H) |
| 10 | 1746-1735 | COOR | ν (C=O) |
| 11 | 1250-1240 | COOR | ν (C—O—C) |
| 12 | 980-950 | C—O O—CH$_2$ | |

With the above characteristic infrared frequencies, the absorption maxima of the frequencies in Part I and II studies were as follows:

TABLE 19

PART I AND II IR PEAK MAXIMUM WAVE #S (CM-1) arranged according to intensity

| | 1 hour | 4 hours | 8 hours | 10 hours | 24 hours |
|---|---|---|---|---|---|
| 1. | 1074.5 | 1068.7 | 1068.7 | 1587.6 | 1068.7 |
| 2. | 1039.8 | 1037.8 | 1037.8 | 3370.1 | 1037.8 |
| 3. | 3393.2 | 3412.5 | 3412.5 | 1076.4 | 3408.6 |
| 4. | 1589.5 | 1242.3 | 1244.2 | 1037.8 | 1242.3 |
| 5. | 1425.6 | 1740.0 | 1738.1 | 1421.7 | 1591.5 |
| 6. | 1244.2 | 1373.5 | 1375.4 | 1246.2 | 1375.4 |
| 7. | 1738.1 | 1637.8 | 1635.8 | 2042.9 | 1421.7 |
| 8. | 603.8 | 1423.6 | 1425.6 | 1738.1 | 1738.1 |
| 9. | 2926.4 | 603.8 | 601.9 | 603.8 | 669.4 |
| 10. | 2039.0 | 2924.4 | 2924.4 | 2928.3 | 2924.4 |
| 11. | 960.7 | 960.7 | 958.7 | 960.7 | 603.8 |

PART II

0 Hours*

TABLE 19-continued

| 1. | 1074.5 | 3397.1 | 1072.6 | 1068.7 | 1068.7 |
|---|---|---|---|---|---|
| 2. | 3393.2 | 1072.6 | 1037.8 | 3408.6 | 1037.8 |
| 3. | 1593.4 | 1593.4 | 3404.8 | 1244.2 | 3420.2 |
| 4. | 1244.2 | 1560.6 | 1244.2 | 1734.2 | 1244.2 |
| 5. | 1419.8 | 1244.2 | 1597.3 | 1635.8 | 1734.2 |
| 6. | 1734.2 | 1419.8 | 1558.7 | 1653.2 | 1635.8 |
| 7. | 2039.0 | 1736.2 | 1419.8 | 1375.4 | 1653.2 |
| 8. | 638.5 | 2924.4 | 1375.4 | 2922.5 | 1375.4 |
| 9. | 474.5 | 472.6 | 1740.0 | 472.6 | 472.6 |
| 10. | 2927.4 | 607.7 | 605.7 | 1558.7 | 1419.8 |
| 11. | 960.7 | 960.7 | 669.4 | 1419.8 | 1558.7 |
| 12. | 873.9 | 875.8 | 2924.4 | 1541.3 | 605.7 |
|  |  |  |  |  | 603.8 |
|  |  |  |  |  | 2924.4 |
|  |  |  |  |  | 541.3 |

From an earlier infrared scan of CARRISYN ® extract, deacetylated CARRISYN ® extract and acetylated CARRISYN ® extract, the carboxylate carbonyl bonds and the ester carbonyl frequencies were identified. The carbonyl functional group and the C—O—C stretches of the acetylated CARRISYN ® extract were located between 1748-1735 cm$^{-1}$ and 1246-1235 cm$^{-1}$ respectively. The caraboxylate carbonyl stretches of the deacetylated CARRISYN ® extract were observed between 1600-1550 cm$^{-1}$ and 1450-1400 cm$^{-1}$ respectively.

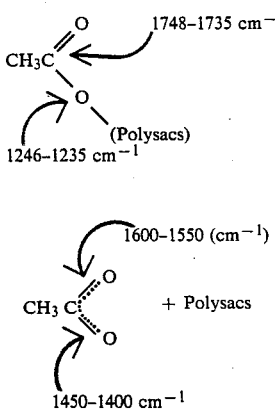

TABLE 20

| CARRISYN ® Extract 531 | CARRISYN ® Extract 531 (deacetylated) | CARRISYN ® Extract 531 (acetylated) |
|---|---|---|
| 1591.5 | 1431.4 | 1244.2 |
| 3414.4 | 3400.9 | 1741.9 |
| 1072.6 | 1032.0 | 1064.8 |
| 1246.2 | 1062.9 | 3460.7 |
| 1740.0 | 1091.8 | 1375.4 |
| 1431.4 | 875.8 | 1647.4 |
| 603.8 | 1147.8 | 1433.3 |
| 2930.2 | 1645.5 | 2932.2 |
| 806.3 | 2924.4 | 1541.3 |
| 958.7 | 814.1 | 956.8 |
| 879.6 | 615.4 | 603.8 |

When CARRISYN ® extract was deacetylated, the absence of the ester C—O—C stretch frequency between 1248-1235 cm$^{-1}$ was observed. It was noticed that the largest peak of the spectrum was centered at 1431 cm$^{-1}$. The degree of acetylation/deacetylation of CARRIYN ® extract may be monitored by these two peaks. Actually, for this particular example, the peak at 1431 cm$^{-1}$ (1560-1339 cm$^{-1}$) was contaminated by amide II peak since amide I could be observed at 1646 cm$^{-1}$.

However, Table 21 illustrates the absorption ratios of these two peaks for the Part I and Part II study.

TABLE 21

| Sample # (Hours) | 1450-1400 cm-1 Abs | 12480-1240 (cm-1) Abs | Abs. Ratio |
|---|---|---|---|
| PART I | | | |
| 1 | .585 | .584 | .998 |
| 2 | .607 | .600 | .988 |
| 4 | .289 | .487 | 1.685 |
| 8 | .289 | .450 | 1.557 |
| 10 | .387 | .326 | 0.842 |
| 24 | .248 | .308 | 1.242 |
| PART 2 | | | |
| 0 | .278 | .475 | 1.709 |
| 1 | .496 | .513 | 1.034 |
| 2 | N/A | N/A | N/A |
| 4 | .452 | .497 | 1.10 |
| 8 | .437 | .524 | 1.20 |
| 10 | .291 | .436 | 1.498 |

About 35 gallons of aloe vera gel were processed for the above characterization study. The process from washing through to filtration lasted approximately one hour and 20 minutes. This study demonstrated no noticeable degradation of the gel within this time period.

The alcohol precipitation step was shown to be an important factor in the quality of CARRISYN ® extract produced. While CARRISYN ® extract yield was increased by longer settling time in alcohol, the quality of the CARRISYN ® extract produced may not be ideal for cell proliferation. It is believed that a time of 4-5 hours in alcohol is optimum for a good yield without adverse degradation.

It was observed in the Part II study that CARRISYN ® extract yield is highest if alcohol precipitation is carried out immediately. Very little adverse effect on the cells or change in infrared spectrum was noticed if alcohol was added within 4 hours.

Infrared spectroscopy may offer the best technique to monitor the quality of CARRISYN ® extract produced. The infrared spectra give characteristic strong ester carbonyl absorption peaks while the deacetylated CARRISYN ® extract resulted in no such peaks. It is believed that the degree of deacetylation may be monitored by this technique. The only problem with this technique is that the presence of amides may influence the value of the carboxylate absorption peaks.

EXAMPLE 28

FIGS. 8-13 show infrared spectra for six different samples of CARRISYN ® extract obtained from the *Aloe barbadensis* Miller plant by the process of the invention. As may easily be seen, the spectrum for each sample shows between 5 and 7 well resolved peaks from a wavenumber of about 1750 to a wavenumber of about 1250. As discussed above in Example 24, these peaks are indicative of the following functional groups: RCOO—, R—NHCOCH$_3$ and R—OOCCH$_3$. It is these functional groups which are believed to give CARRISYN ® extract its activity. Thus, FIGS. 8-13 demonstrate that a consistent CARRISYN ® extract product is produced from the leaves of the *Aloe barbadensis* Miller plant by the process of the present invention.

EXAMPLE 29

Figure 14:
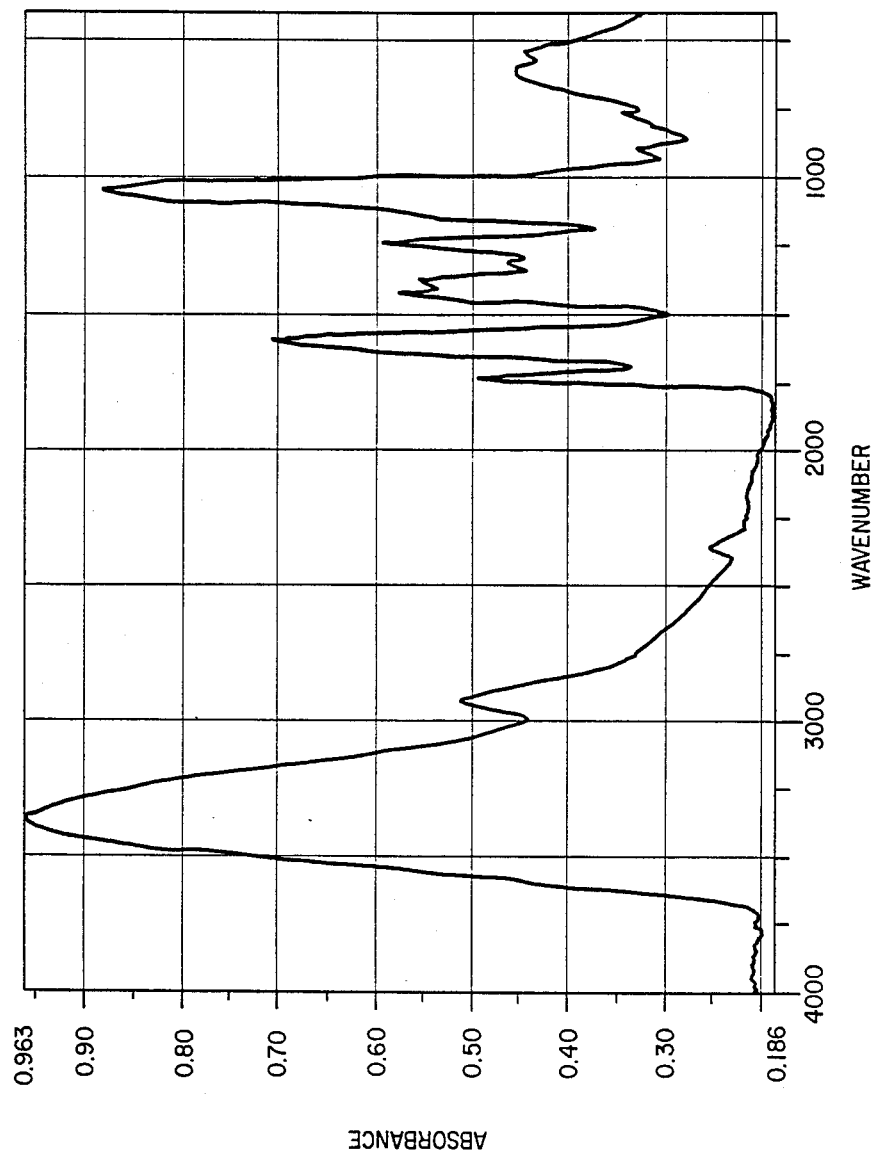
FIG. 14 shows data for raw aloe vera gel taken from an *Aloe vera* juice.

FIG. 14 shows an infrared spectrum for raw *Aloe vera* gel that was cast into a film. This spectrum also shows between 5 and 7 well resolved peaks from a wavenumber of about 1750 to a wavenumber of about 1250. Thus, FIG. 14 provides evidence that CARRISYN ® extract is present in the raw gel from the *Aloe vera* plant.

EXAMPLE 30

Figure 15:
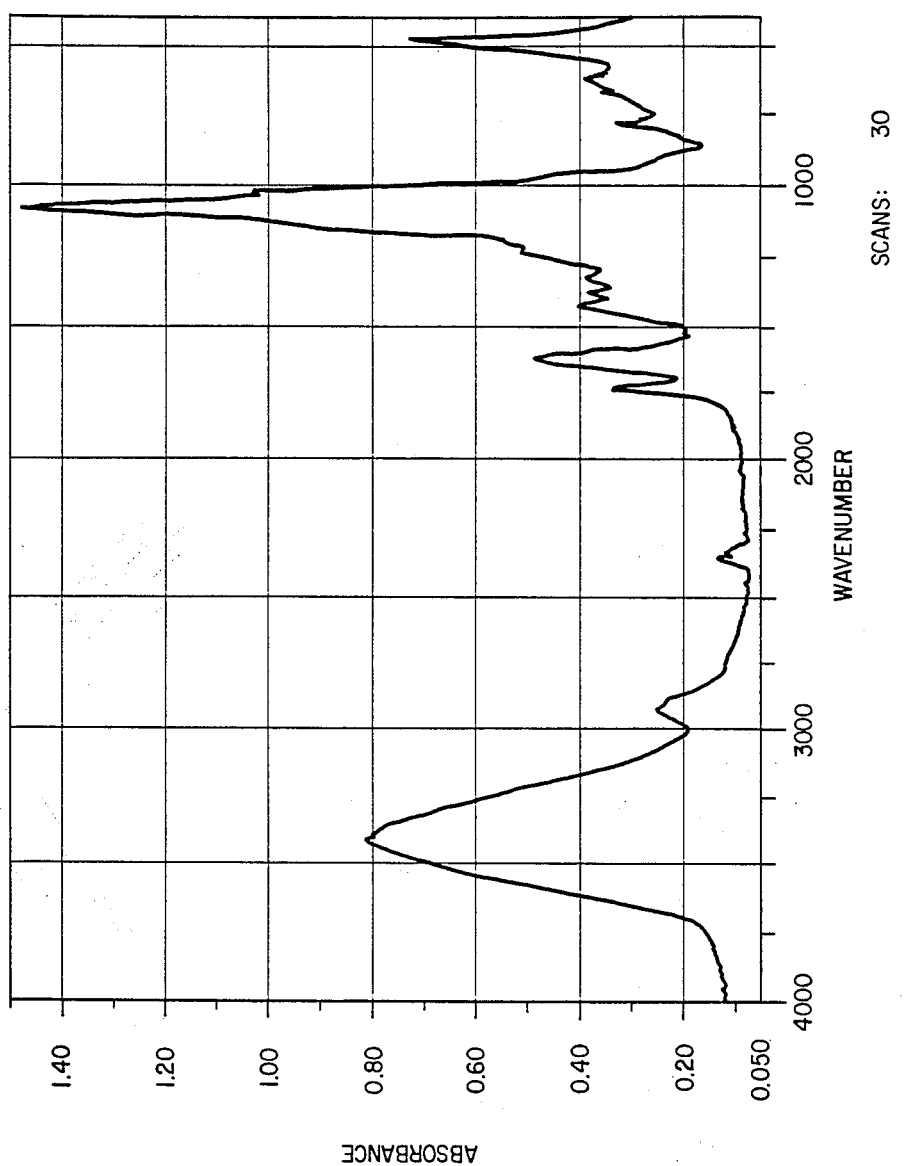
FIG. 15 shows the absorbance data for the active ingredient CARRISYN®.

FIG. 15 shows an infrared spectrum for a sample of CARRISYN ® extract. As will be noted, the characteristic well-resolved peaks between a wavenumber of 1750 and a wavenumber of 1250 are almost absent. It is believed that this sample of CARRISYN ® extract was precipitated from *Aloe vera* gel or juice with reused alcohol which somehow reduced the precipitation of CARRISYN ® extract.

EXAMPLE —

Figure 16:
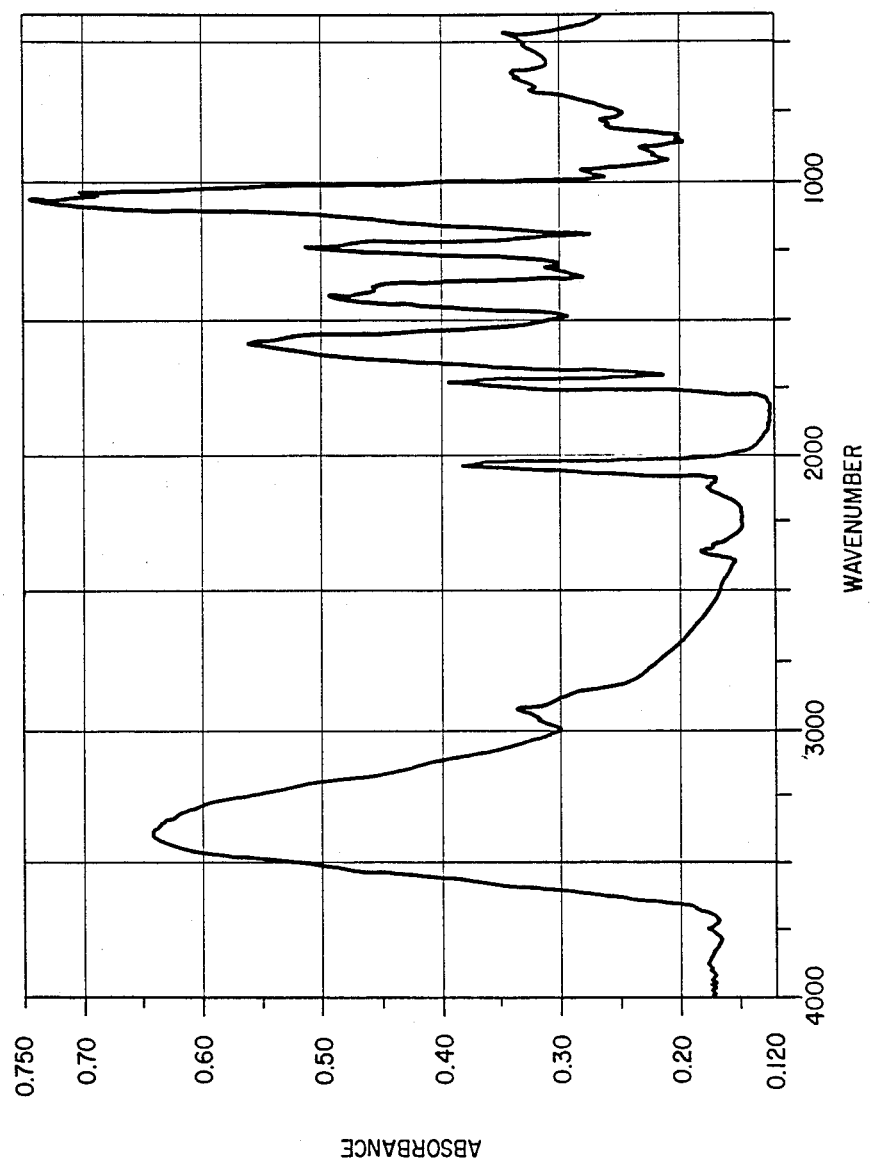
FIGS. 16–17 show infrared spectra for a sample of CARRISYN® extract with a one hour and a ten hour time period between the time the aloe gel was removed from the leaf and the time the aloe juice was extracted with alcohol.
Figure 17:
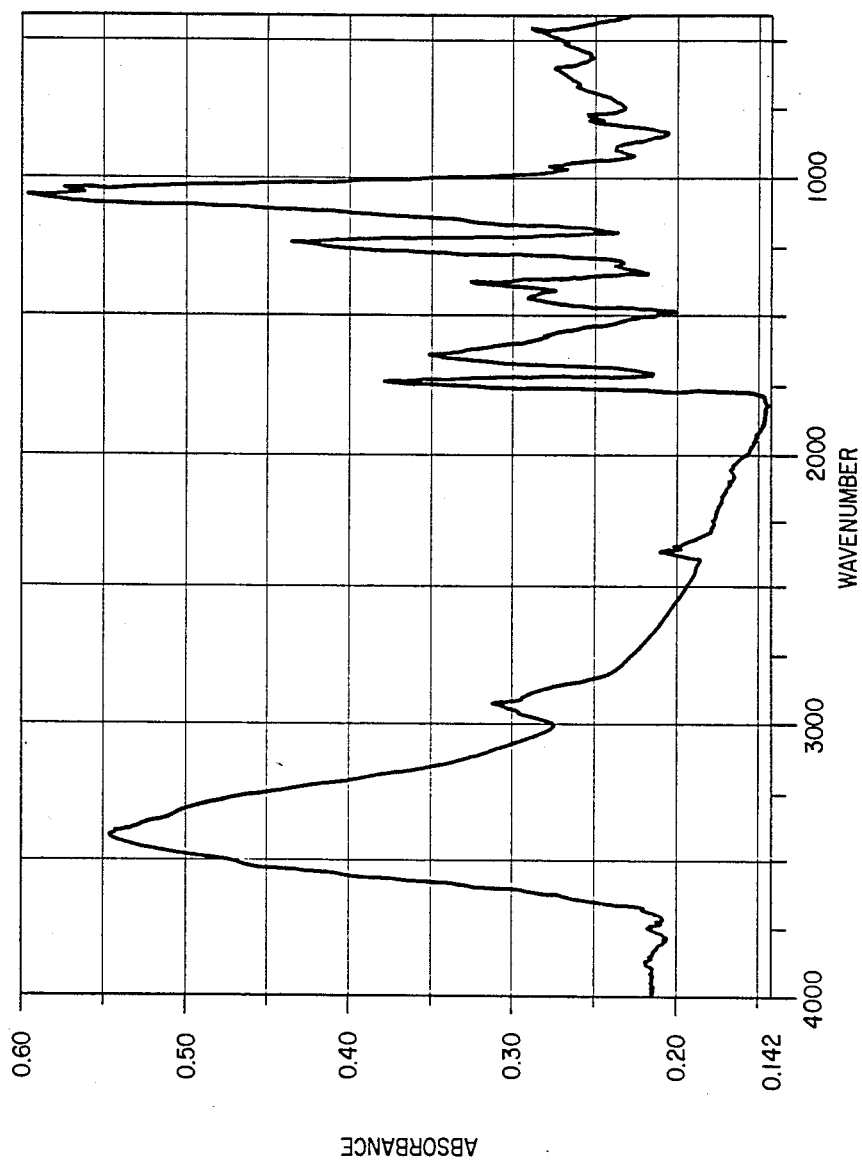

FIGS. 16-17 demonstrate the importance of extracting CARRISYN ® extract from Aloe juice with alcohol as quickly as is practicable after preparation of the Aloe juice. FIG. 16 is a spectrum of a CARRISYN ® extract sample that was extracted with alcohol from Aloe juice one hour after the Aloe juice was prepared. FIG. 17 is a spectrum of a CARRISYN ® extract sample that was extracted with alcohol from Aloe juice ten hours after the Aloe juice was prepared. The characteristic well-resolved peaks between a wavenumber of 1750 and a wavenumber of 1250 show a significantly higher absorbance level in the spectrum of FIG. 16 compared to the spectrum of FIG. 17. Thus, better quality CARRISYN ® extract appears to be produced the sooner CARRISYN ® extract is extracted with alcohol from Aloe juice.

EXAMPLE 32

Figure 18:
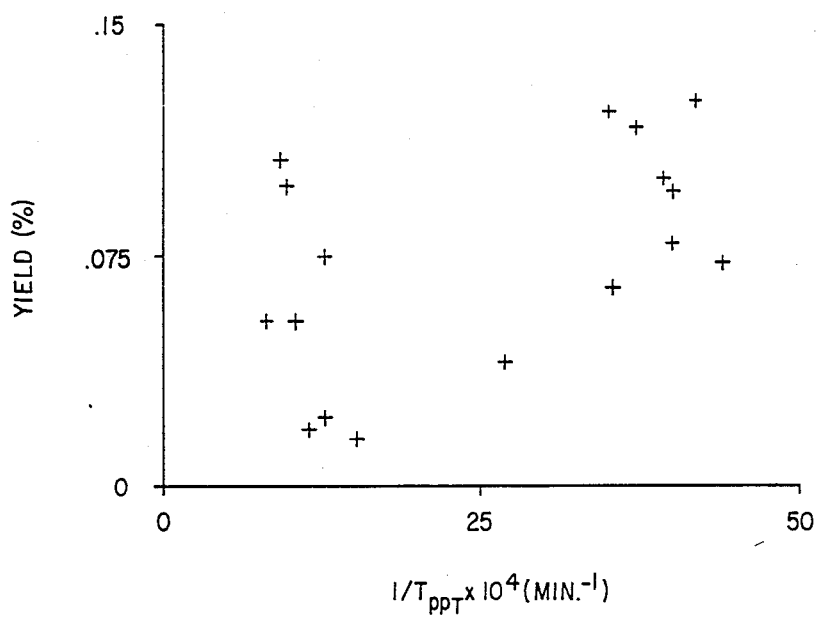
FIG. 18 shows a plot of CARRISYN® extract yield versus reciprocal time of gel in alcohol (precipitation process).
Figure 19:
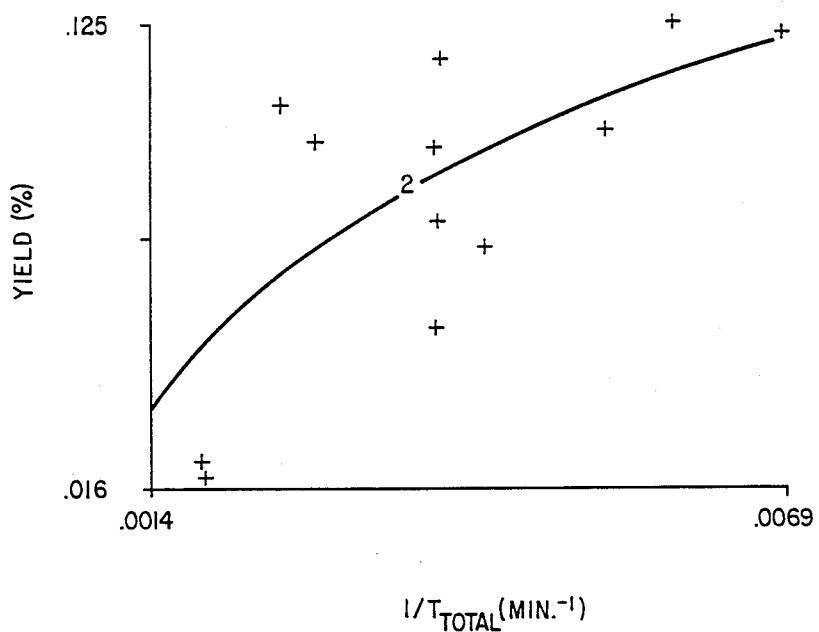
FIG. 19 shows a plot of CARRISYN® extract yield versus reciprocal total process time before precipitation.
Figure 20:
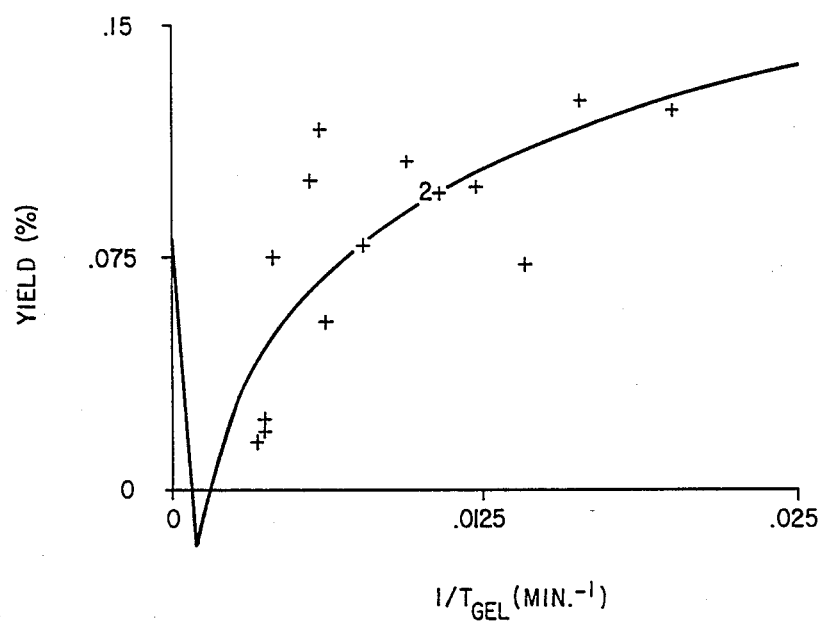
FIG. 20 shows a plot of CARRISYN® extract yield versus reciprocal time of homogenization and filtration.

FIGS. 18-20 were constructed from the data listed in Table 22 below.

TABLE 22

TIME INVOLVED FOR VARIOUS PROCESSES DURING THE PRODUCTION OF SEVERAL MANUFACTURED CARRISYN ® EXTRACT BATCHES

| Batch | Date Of Manufacture | Leaf Processing Time(min) | Homogenization Time(min) | Filtration Time (min) | Alcohol Addition Time (min) |
|---|---|---|---|---|---|
| 1 | 8/6/85 | 75 | 8 | 152 | 15 |
| 2 | 8/23/85 | 270 | 15 | 90 | 6 |
| 3 | 9/18/85 | 404 | 21 | 225 | 60 |
| 4 | 9/20/85 | 242 | 29 | 240 | 60 |
| 5 | 9/23/85 | 209 | 27 | 245 | 60 |
| 6 | 9/26/85 | 375 | 30 | 255 | 60 |
| 7 | 10/1/85 | 200 | 15 | 66 | 60 |
| 1B | 11/25/85 | 72 | 15 | 14 | — |
| 2B | 12/3/85 | 41 | 20 | 12 | — |
| 3B | 12/17/85 | 73 | 18 | 149 | — |
| 4B | 1/7/86 | 137 | 28 | 364 | 15 |
| 5B | 1/10/86 | 146 | 30 | 63 | 10 |
| 6B | 1/24/86 | 113 | 25 | 105 | — |
| 7B | 2/5/86 | 91 | 25 | 25 | 13 |
| 8B | 2/18/86 | 143 | 26 | 44 | 13 |
| 9B | 2/26/86 | 103 | 32 | 29 | 15 |
| 10B | 3/18/86 | 119 | 75 | 104 | 15 |

| Batch | Precipitation Time (min) | $1/T_{ppt} \times 10^4$ (min) | Total Time[1] Before Precipitation | $1/T_{total} \times 10^3$ (min) |
|---|---|---|---|---|
| 1 | 1210 | 8.26 | 255 | 3.92 |
| 2 | 1095 | 9.13 | 384 | 2.60 |
| 3 | 790 | 12.7 | 700 | 1.43 |
| 4 | 790 | 12.7 | 535 | 1.87 |
| 5 | 870 | 11.5 | 526 | 1.90 |
| 6 | 660 | 15.2 | 695 | 1.44 |
| 7 | 1035 | 9.66 | 345 | 2.90 |
| 1B | 283 | 35.3 | 117 | 8.54 |
| 2B | 375 | 26.7 | 76 | 13.16 |
| 3B | 270 | 37.0 | 252 | 3.97 |
| 4B | 960 | 10.4 | 542 | 1.85 |
| 5B | 250 | 40.0 | 255 | 3.92 |
| 6B | 250 | 40.0 | 253 | 3.95 |
| 7B | 285 | 35.0 | 144 | 6.94 |
| 8B | 227 | 44.1 | 230 | 4.35 |
| 9B | 240 | 41.7 | 167 | 5.99 |
| 10B | 255 | 39.2 | 185 | 5.41 |

| Batch | Total Time[2] For Homogenization & Filtration | $1/T_{gel} \times 10^3$ (min) | Yield (GRAMS) | % Yield (w/v) |
|---|---|---|---|---|
| 1 | 160 | 6.3 | 36.7 | 0.054% |
| 2 | 105 | 9.5 | 80.0 | 0.106% |
| 3 | 246 | 4.1 | 71.1 | 0.075% |
| 4 | 269 | 3.7 | 22.0 | 0.023% |
| 5 | 272 | 3.7 | 17.8 | 0.018% |
| 6 | 285 | 3.5 | 15.3 | 0.016% |
| 7 | 81 | 12.3 | 88.7 | 0.098%. |
| 1B | 29 | 34.5 | 34.3 | 0.065% |
| 2B | 32 | 31.3 | 13.8 | 0.041% |
| 3B | 167 | 6.0 | 177.3 | 0.117% |
| 4B | 392 | 2.6 | 81.8 | 0.054% |
| 5B | 93 | 10.8 | 145.0 | 0.096% |
| 6B | 130 | 7.7 | 120.3 | 0.074% |
| 7B | 50 | 20.0 | 184.9 | 0.122% |
| 8B | 70 | 14.3 | 109.8 | 0.073% |
| 9B | 61 | 16.4 | 188.7 | 0.125% |
| 10B | 179 | 5.6 | 151.5 | 0.100% |

[1]Total time from the cut on the first Aloe leaf until the first drop of alcohol is added to the resulting gel.
[2]The total time for homogenization and filtration of the gel only.

As shown in FIG. 18, Carrisyn TM yield does not appear to be related to the time the gel is in alcohol. As shown in FIG. 19, CARRISYN ® extract yield is inversely proportional to the total process time before precipitation. As shown in FIG. 20, CARRISYN ® extract yield is inversely proportional to the time of homogenization and filtration. Thus, for highest CARRISYN ® extract yields, the total process time before precipitation, more specifically the the time of homogenization and filtration, should be minimized to the extent possible.

EXAMPLE 33

Figure 21:
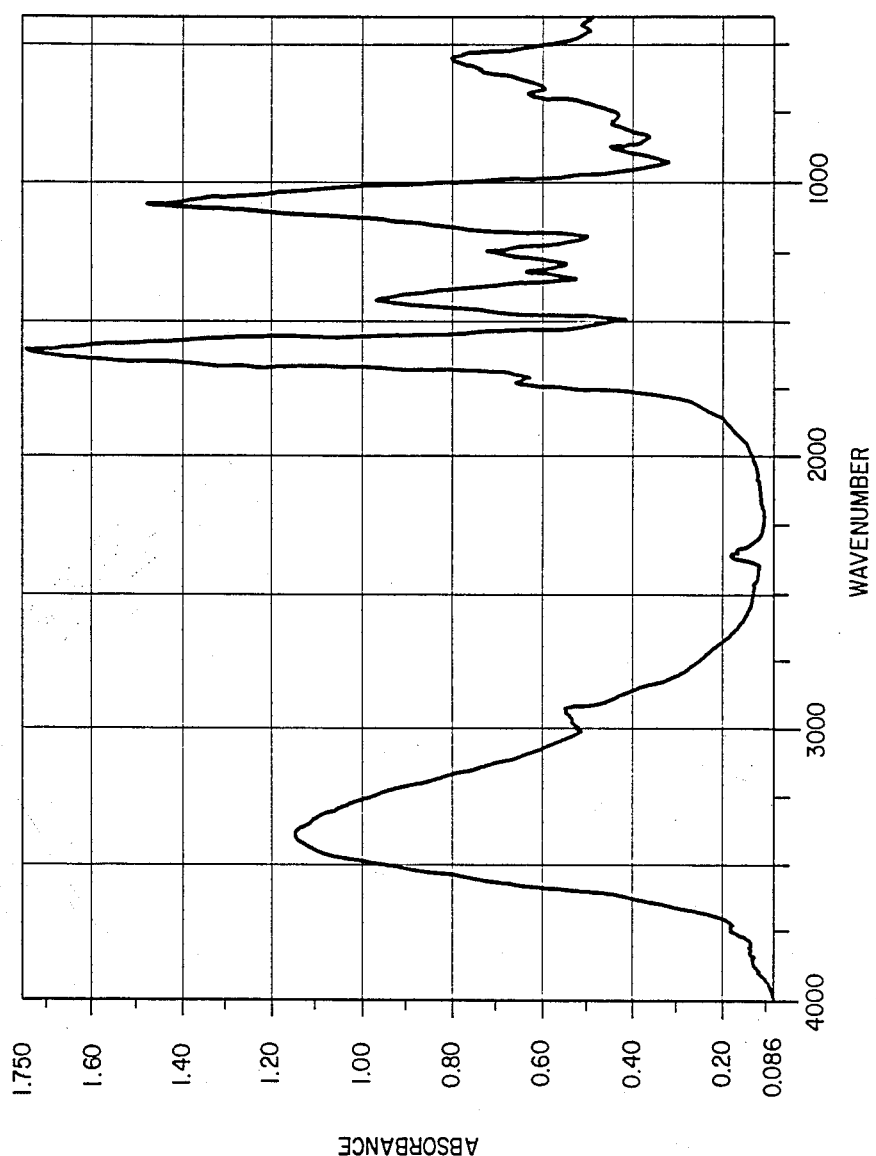
FIG. 21 shows an infrared spectrum of the alcohol precipitation product of the juice from *Aloe ferox*. The *Aloe ferox* sample was in the form of a potassium bromide powder.

FIG. 21 shows an infrared spectrum for the alcohol precipitation product of the juice from *Aloe ferox*. This spectrum shows several well resolved peaks from a wavenumber of about 1750 to a wavenumber of about 1250. Thus, the alcohol precipitation product of the juice from *Aloe ferox* may have similar activity as CARRISYN ® extract.

EXAMPLE 34

Figure 22:
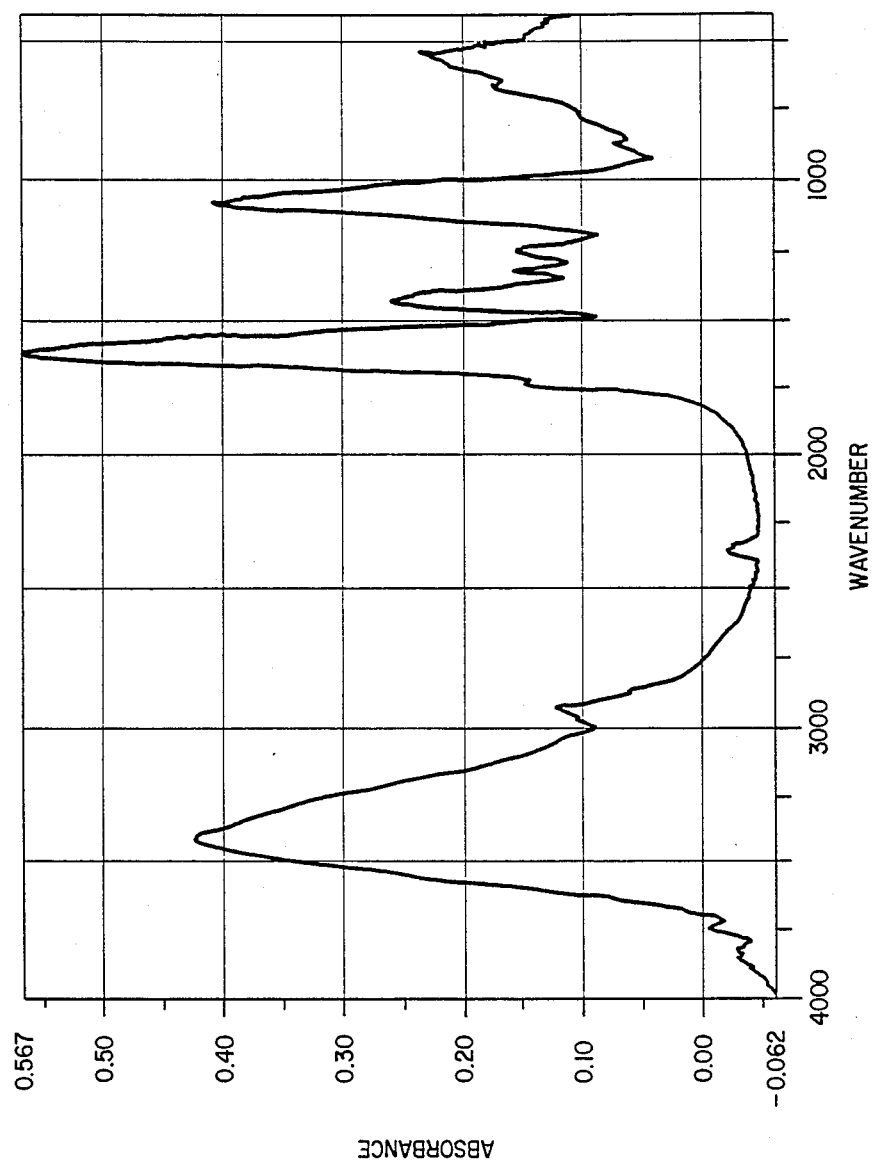
FIG. 22 shows an infrared spectrum of the alcohol precipitation product of the juice from *Aloe africana*. The *Aloe africana* sample was in the form of a potassium bromide powder.

FIG. 22 shows an infrared spectrum for the alcohol precipitation product of the juice from *Aloe africana*. This spectrum shows several well resolved peaks from a wavenumber of about 1750 to a wavenumber of about 1250. Thus, the alcohol precipitation product of the juice from *Aloe africana* may have similar activity as CARRISYN ® extract.

EXAMPLE 35

Figure 23:
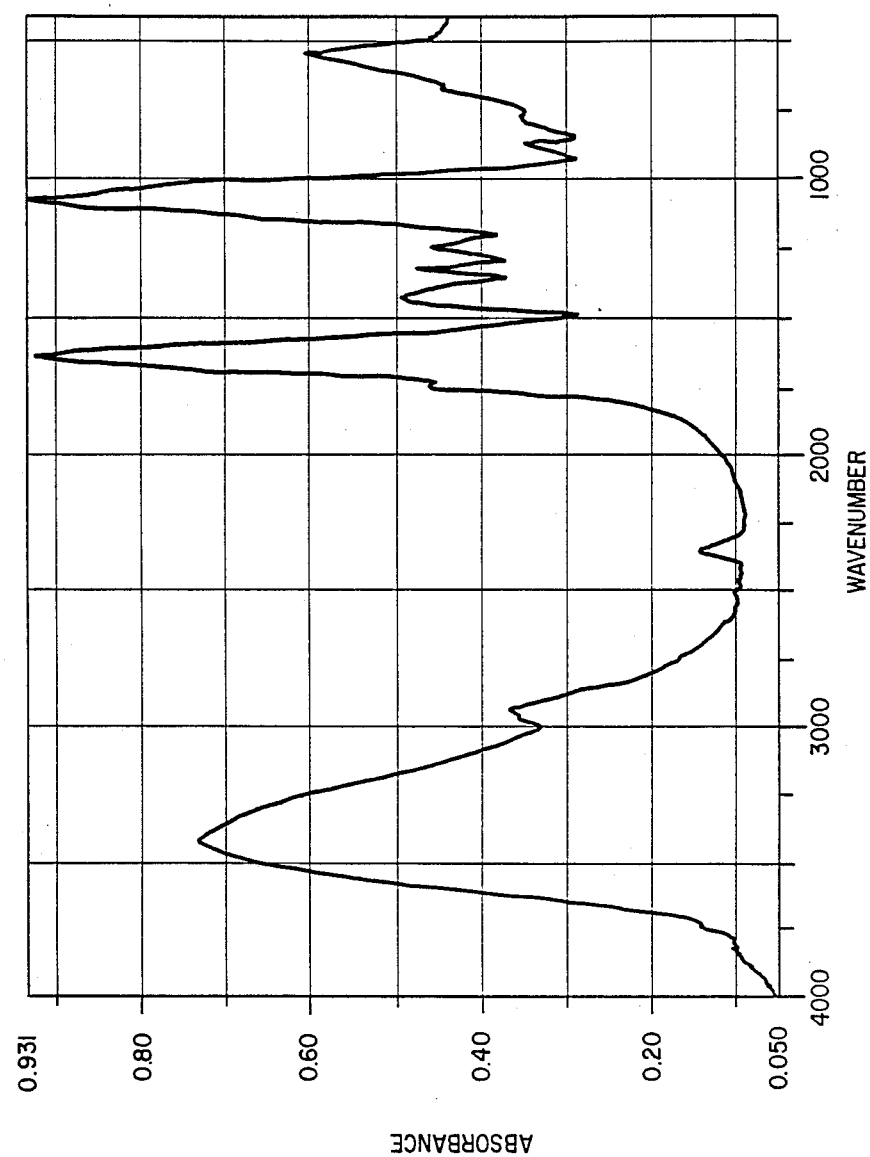
FIG. 23 shows an infrared spectrum of the alcohol precipitation product of the juice from *Africana ferox*. The *Aloe ferox* sample was in the form of a KBR powder.

FIG. 23 shows an infrared spectrum for the alcohol precipitation product of the juice from *Africana ferox*, an hybrid of *Aloe ferox* and *Aloe africana*. This spectrum shows several well resolved peaks from a wavenumber of about 1750 to a wavenumber of about 1250. Thus, the alcohol precipitation product of the juice from *African*

*ferox* may have similar activity as CARRISYN® extract.

EXAMPLE 36

Figure 24:
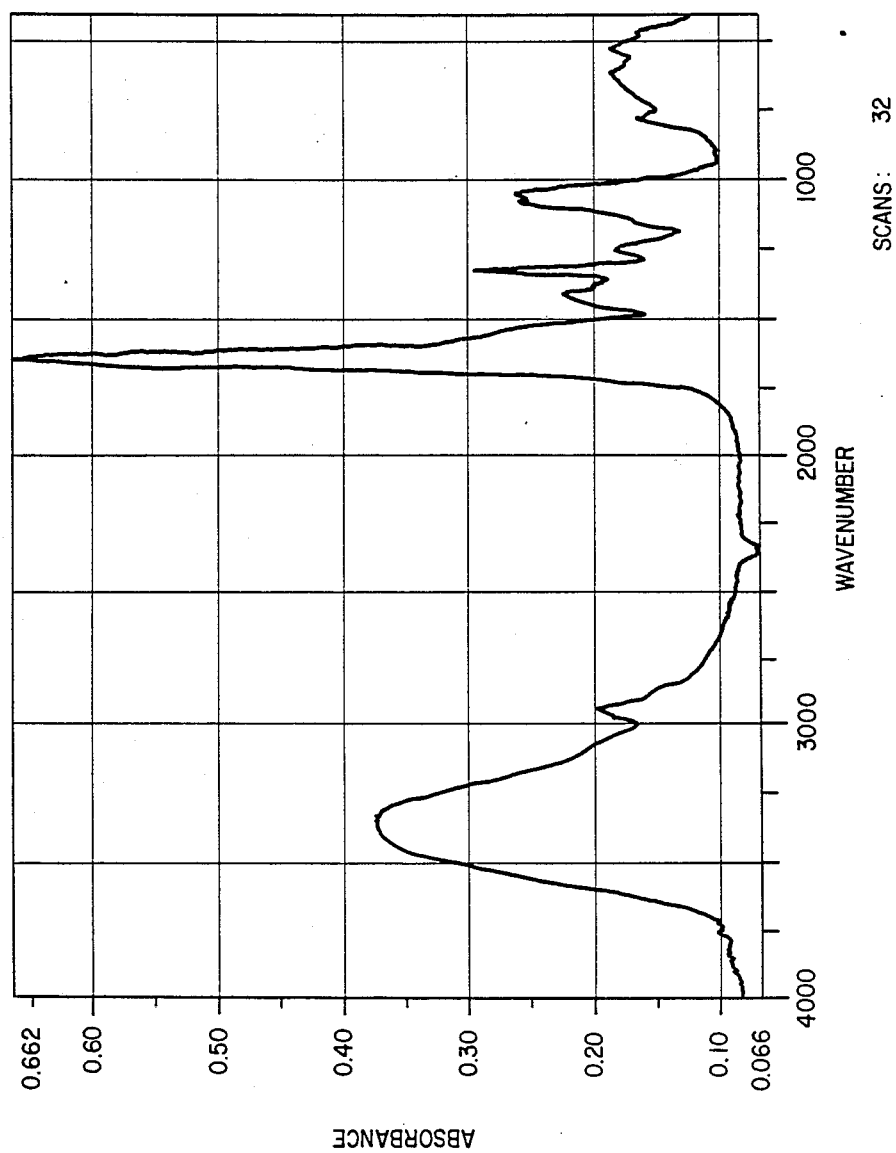
FIG. 24 shows an infrared spectrum of the alcohol precipitation product of the juice from *Aloe dichotoma*. The *Aloe dichotoma* sample was in the form of 1% KBR powder.
Figure 25:
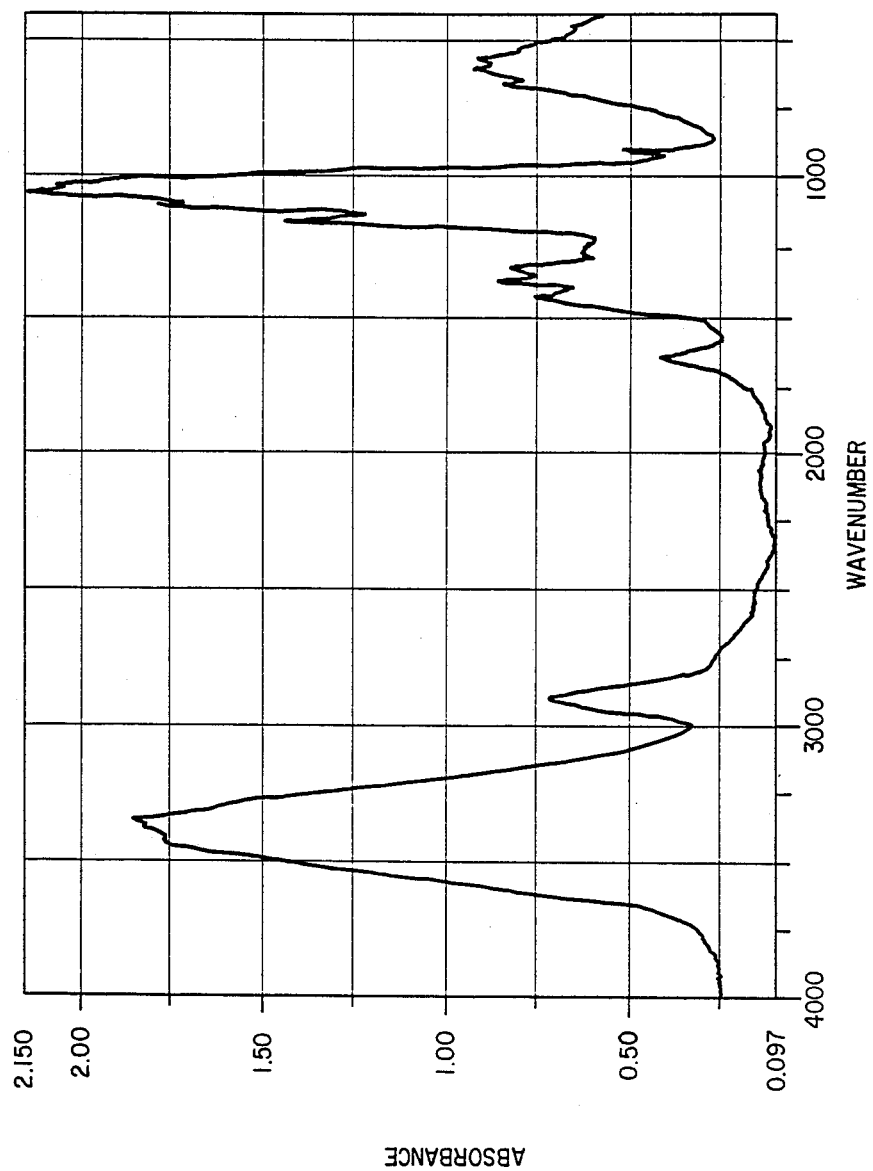
FIG. 25 shows an infrared spectrum of cellulose.
Figure 26:
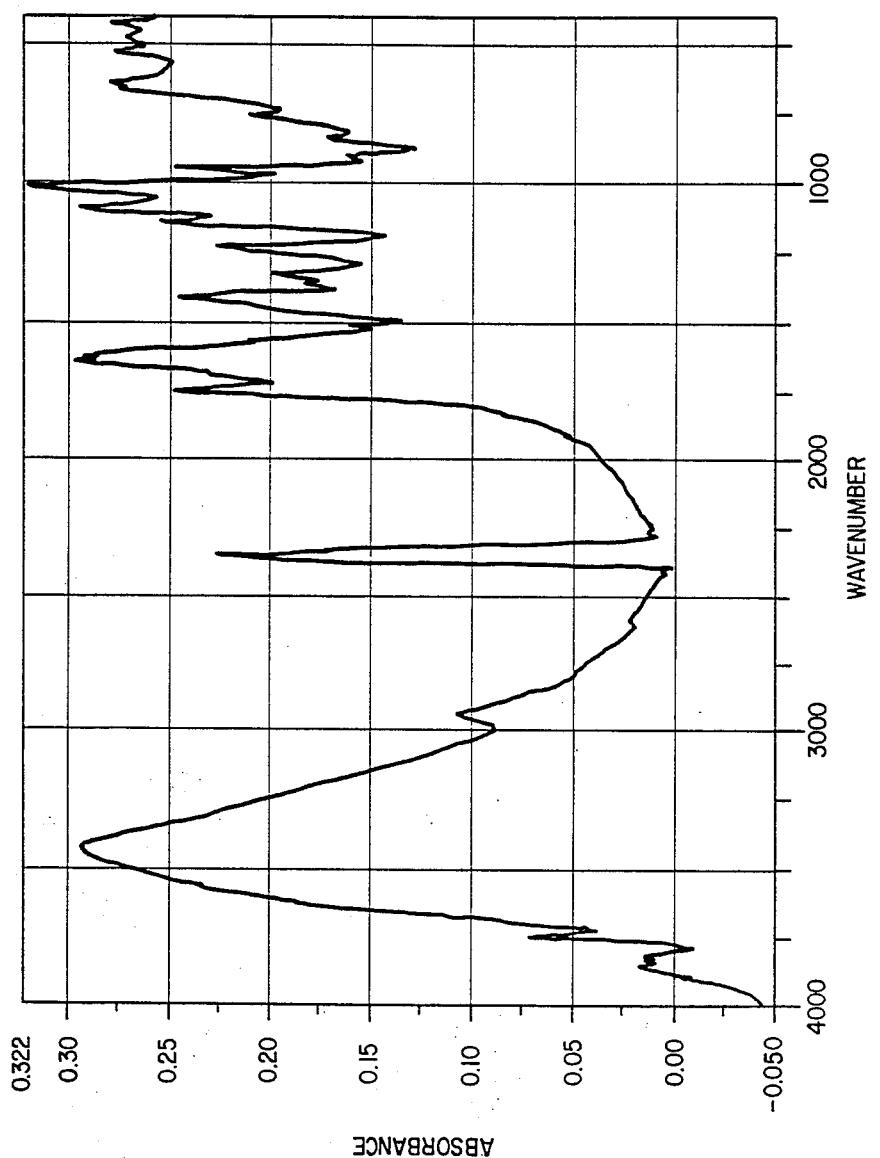
FIG. 26 shows an infrared spectrum of polygalacturonic acid. The polygalacturonic acid sample was in the form of a powder.
Figure 27:
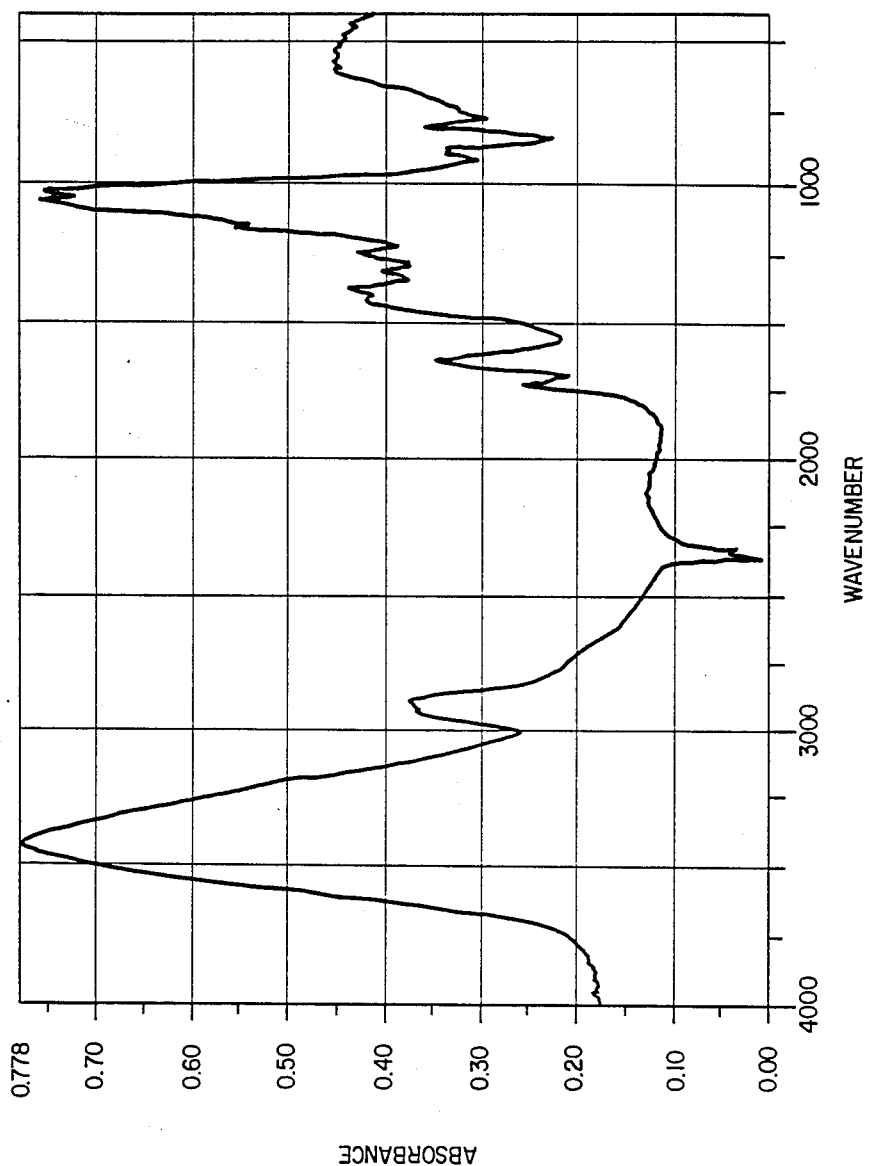
FIG. 27 shows an infrared spectrum of glucomannan from the Konjac plant. The glucomannan Konjac sample was in the form of powder in KBR.
Figure 28:
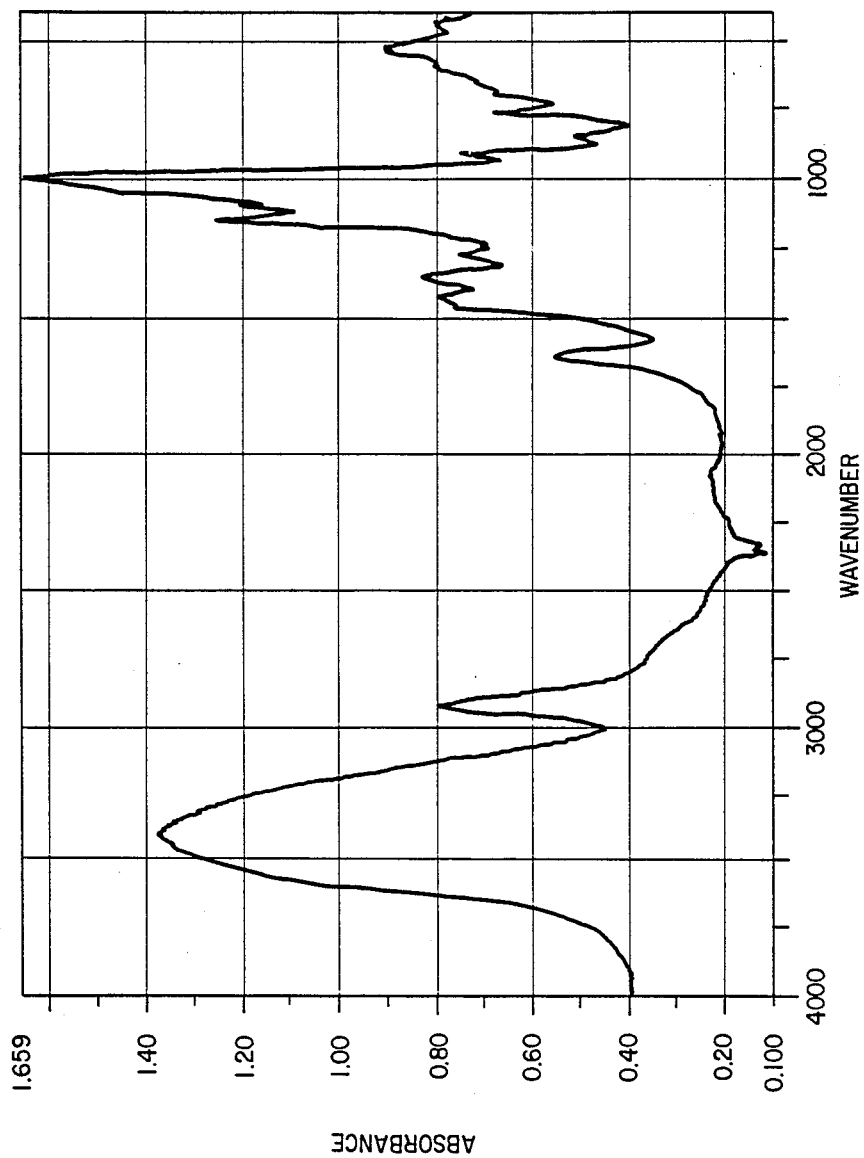
FIG. 28 shows an infrared spectrum of dextran.
Figure 29:
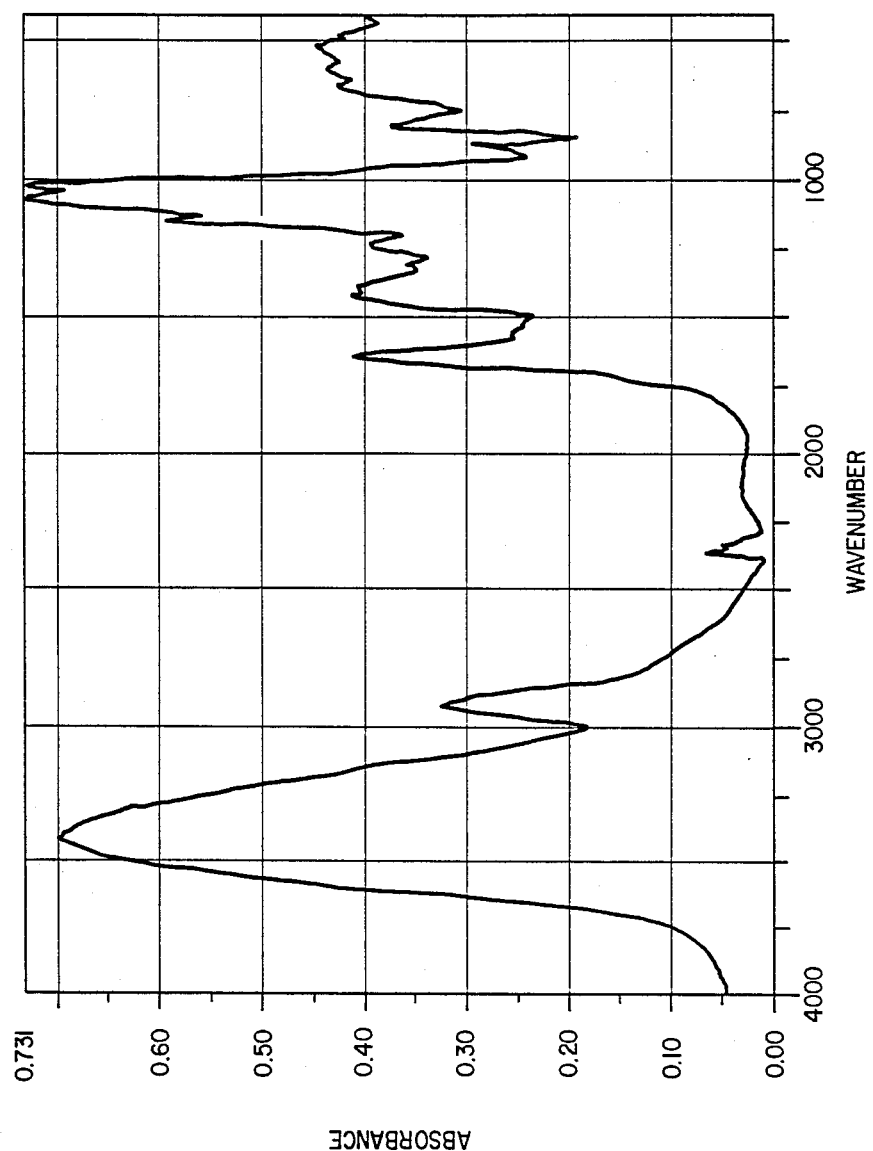
FIG. 29 shows an infrared spectrum of guar gum. The gum guar Lot #101F-0279 of Sigma Chemical Company sample was in the form of powder in KBR.

FIG. 24 shows an infrared spectrum for the alcohol precipitation product of the juice from *Aloe dichotoma*. This spectrum shows some peaks from a wavenumber of about 1750 to a wavenumber of about 1250. The alcohol precipitation product of the juice from *Aloe dichotoma* may have some similar activity as CARRISYN® extract.

EXAMPLE 37

FIGS. 25-29 show infrared spectra for cellulose, polygalacturonic acid, glucomannan from the Konjac plant, dextran and guar gum, respectively. These spectra show some peaks from a wavenumber of about 1750 to a wavenumber of about 1250 but are not the sharp well-resolved peaks of CARRISYN® extract as in FIG. 8. Thus, it is not believed that cellulose, polygalacturonic acid, glucomannan from the Konjac plant, dextran or guar gum would have the same activity as CARRISYN® extract.

EXAMPLE 38

Modification of rheological characteristics of CARRISYN® extract:

The modifications of CARRISYN® extract discussed below may affect one or more of the following rheological characteristics of CARRISYN® extract: absorption, penetration, specificity, solubility, viscosity, stability, activity, or the target tissue. These modifications are important in drug targeting. Infrared spectra of the following modified forms of CARRISYN® extract have been produced. It is inferred that modified forms of CARRISYN® extract may posses similar biological activity as unmodified CARRISYN® extract.

A. Hydrogen Peroxide Treatment of CARRISYN® Extract 1.00 g. of CARRISYN® extract (light pink-brown color, Lot #8B) was placed in a 1 L round bottom flask containing 500 ml of deionized water and a 1" stir bar. The mixture was stirred at ambient temperature for 30 minutes, and then in a cold room (4° C.) for 30 minutes to give a slightly viscous, heterogeneous mixture containing some undissolved CARRISYN® extract. To this vigorously stirred mixture was added dropwise at 4° C., 5 ml of 30% $H_2O_2$ solution (Mallinckrodt, AR grade, #5240). There were no observed changes or gas evolution. The mixture was stirred gently at 4° C. for 16 hours. No physical change was observed.

Solid sodium bisulfite (granular, Baker, #1-3556) (4.588 g., 1.0 equivalent with respect to $H_2O_2$) was dissolved in 30 ml $H_2O$. The resultant clear solution was added dropwise in 20 minutes to the stirring reaction mixture. During the addition, the reaction pH was monitored by pH paper and kept at pH 7±0.5 using sodium bicarbonate solution (1M, Fisher, #S-233). After complete addition, the mixture was stirred for 1 hour at ambient temperature, then concentrated on a rotary evaporator under reduced pressure at 35°-40° C. to a volume of approximately 80 ml. This concentrate was placed in pre-washed dialysis tubing (approximately 30 cm long, dry cylinder diameter 28.6 mm, Spectrapor Medical Indust., Inc. Los Angeles, CA #132633, 2000 MW cutoff) and dialyzed against deionized water in a 6 L Erlenmeyer flask at 4° C. for 24 hours with water changes every six hours. The tubing was opened and the contents freeze-dried under vacuum for 12 hours to give 420 mg. of an off-white powder.

B. Sodium Periodate Cleavage* of CARRISYN® Extract 1.00 g. of CARRISYN® extract (light pink-brown color, Lot #8B) was placed in a 1 L round bottom flask containing 500 ml of deionized water and a 1" stir bar. The mixture was stirred at ambient temperature for 30 minutes, then in a cold room (4° C.) for 30 minutes to give a slightly viscuous, heterogeneous mixture with some undissolved CARRISYN®extract. To this was added a solution of sodium periodate (99% Aldrich Chem. Co., #21,004-8; 59 mg, 5 mol % based on an average MW of 180/monomer) in 10 ml deionized water with vigorous stirring over 15 minutes. The mixture was stirred at 4° C. for 15 hours. The solution became homogeneous and developed a light pink color. The pH was monitored with pH paper and kept at pH 7±0.5.

Fifty (50) ml of ethylene glycol was added (three equivalents with respect to $NaIO_4$) and was stirred at room temperature for three hours to destroy unreacted $NaIO_4$. Solid $NaBH_4$ (630 mg, Aldrich Chem. Co., #19, 807-2, 98+%) was added in small portions with vigorous stirring over 30 minutes. Upon complete addition, the mixture was stirred at ambient temperature for 3 hours. Excess $NaBH_4$ was quenched with 20 ml acetone (distilled, 99.9+% HPLC grade, Aldrich Chemical Co., #27,072-5) at room temperature for 2 hours. The pH was 22 8, so it was adjusted to pH 7 with 50% aqueous HOAc solution (Fisher Chemical Co., HOAc reagent grade). The acetone was evaporated and the solution was concentrated on a rotary evaporator under reduced pressure at 35°-40° C. to approximately 80 ml. The residue was transferred to dialysis tubing (approximately 30 cm long, dry cylinder diameter 28.6 mm, Spectrapor Medical Indust. Inc., Los Angeles, CA #132633, 2000 MW cutoff) that had been pre-washed with deionized water. The residue was dialyzed against deionized water in a 6 L Erlenmeyer flask for 24 hours with water changes every six hours.

The tubing contents was removed and freeze dried for twelve hours under vacuum to give 470 mg of a light brown powder.

*Experimental procedure taken in part from: J. M. Boffitt "Periodate Oxidation of Carbohydrate" in *Adv. Carbohydrate Chemistry* 11:1–41(1956).

C. Phosphorylation* of CARRISYN® Extract

To a solution of sodium dihydrogen phosphate monohydrate (Matheson Coleman and Bell, CB742, 577 mg) and disodium hydrogen phosphate heptahydrate (Fisher Sci., S-373, Lot #855049; 837 mg) in 30 ml of deionized water was added 1.00 g of CARRISYN® extract (light pink-brown colored powder, Lot #8B). The heterogeneous mixture was stirred at 35° C. for 30 minutes to give a pink-light brown paste. The water was evaporated on a rotary evaporator under reduced pressure at approximately 40° C. The residue was further dried at 0.1 mm Hg pressure in an oil pump for 3 hours. The hard solid was powdered with a glass rod and placed in a 1 L round bottom flask and then placed in a preheated oil bath at 155° C. A slow stream of argon (prepurified) was passed over the sample which was stirred with a mechanical stirrer and a Teflon ™ paddle. After three hours, the mixture was cooled to ambient temperature, slurried in 50 ml deionized H₂O and placed in dialysis tubing (30 cm long, dry cylinder diameter 28.6 mm, Spectrapor Medical Indust. Inc., Los Angeles, CA #132633, 2000 MW cutoff) which was prewashed with deionized H₂O. The mixture was dialyzed against deionized H₂O in a 6 L Erlenmeyer flask for 24 hours with H₂O changes every six hours in a cold room (4° C.).

The tubing contents at approximately pH 7 were removed and freeze dried for 12 hours under vacuum to give 865 mg of a brown solid.

*Experimental procedure taken in part from: E. F. Paschall "Phosphation with Inorganic Phosphate Salts" in Methods in Carbohydrate Chemistry Vol. IV, pp. 294–296, 1964; R. L. Whistler, Ed., Academic Press, New York. For alternative procedure see, G A Towle and R. L. Whistler, *Methods Carbohydrate Chem.* 6, 408(1972);

D. Partial Methylation* of CARRISYN ® Extract 1.00 g of CARRISYN® extract (light pink-brown color, Lot #8B) was powdered in a mortar and pestle, and then suspended in 75 ml acetone (Fisher Sci., A-13, Lot #856136, distilled). With vigorous stirring, a 4.4 ml 30% NaOH solution made by dissolving NaOH pellets (Mallinckrodt AR grade, 7708, Lot KVHS) in deionized water and 2.2 ml dimethylsulfate (Fisher) were added simultaneously. The reagents were added in 4 equal portions at 15 minute intervals. After complete addition, the mixture was stirred for 15 minutes then evaporated on a rotary evaporator at reduced pressure. The residue was slurried in 50 ml of deionized H₂O and transferred to dialysis tubing (30 cm long, dry cylinder diameter 28.6 mm, Spectrapor Medical indust. Inc., Los Angeles, CA #132633, 2000 MW cutoff) which had been pre-washed with deionized water. The residue was dialyzed against 5% NaHCO₃ solution (NaHCO₃ powder, Fisher, S-233, Lot #722534) in a 6 L Erlenmeyer flask at 4° C. for 24 hours with a solution change every 6 hours. The residue was then dialyzed against deionized H₂O at 4° C. for 36 hours in a 6 L Erlenmeyer flask with a H₂O change every 6 hrs.

The tubing contents at approximately pH 7 were removed and freeze dried for 12 hours under vacuum to give 759 mg. of a light brown powder.

*Experimental procedure taken in part from: E. L. Hirst and E. Percival. "Methylation of Polysaccharides and Fractionation of the Methylated Products" in *Methods in Carbohydrate Chemistry*, Vol. V, pp. 287–296, 1965; R. L. Whistler, Ed., Academic Press, New York. Also, see, W. N. Haworth, *J. Chem. Soc. 107:* 8–16 (1915).

E. Carboxymethylation* of CARRISYN ® Extract 1.00 g of CARRISYN® extract (light pink-brown colored solid, Lot #8B) was powdered in a mortar and pestle, and then suspended in 15 ml of isopropyl alcohol (ACS reagent grade, Aldrich Chem. Co. #19,076-4). With vigorous stirring, 0.5 g NaOH (Mallinckrodt AR grade, 7708, Lot #7708 KVHS) in 1 ml deionized H₂O was added dropwise over 5 minutes and was followed immediately by 140 mg of bromoacetic acid (Eastman Kodak ™ Co. #964) in 1 ml of deionized H₂O. This mixture was stirred at room temperature under an argon stream for 80 minutes. The organic solvent was removed under reduced pressure on a rotary evaporator, in a bath temperature of 30° C. The resultant brown paste was diluted with 30 ml of deionized H₂O and the mixture was neutralized to pH 7 using 20% aqueous acetic acid (prepared from Fisher glacial acetic acid, ACS reagent grade, A-38). The product was transferred to dialysis tubing (30 cm. long, dry cylinder diameter 28.6 mm, Spectrapor Medical Indust. Inc., Los Angeles, CA #132633, 2000 MW cutoff) which was pre-washed with deionized H₂O. The product was dialyzed against deionized H₂O in a 6 L Erlenmeyer flask for 24 hrs. with H₂O changes every 6 hrs. in a cold room (4° C.).

The tubing contents were removed and freeze dried for 12 hours under vacuum to give 609 mg of a brown, brittle solid.

The tubing contents were removed and freeze dried for 12 hours under vacuum to give 609 mg of a brown, brittle solid.

*Experimental procedures taken in part from: Hans Vink. *Die Makromolekulare Chemie* 122:271–274 (1969).

F. Sulfation* of CARRISYN ® Extract

To a 0° C. suspension of sulfur trioxid-trimethylamine complex (aldrich Chem. Co., 13,587-9, white powder) in 50 ml of dimethylformamide (Baker Analyzed reagent grade, 3-9221) was added all at once 1.00 g of CARRISYN ® extract (light pink-brown colored solid, Lot #8B, powdered in mortar/pestle) with vigorous stirring. After approximately 5 min., the mixture became very thick and difficult to stir. The mixture was maintained at 0° C. with stirring for 24 hours, and diluted with 50 ml deionized H₂O and transferred to dialysis tubing (30 cm long, dry cylinder diameter 28.6 mm, Spectrapor Medical Indust. Inc., Los Angeles, CA #132633, 2000 MW cutoff) which had been pre-washed with deionized H₂O. The mixture was dialyzed against 10% aqueous NaHCO₃ solution (prepared from solid NaHCO₃, Fisher Sci. Co., ACS certified, S-233) in a 6 L Erlenmeyer flask at 4° C. for 24 hrs., then against deionized H₂O at 0°–4° C. for 48 hrs. with H₂O changes every 6 hrs.

The tubing contents were removed and freeze dried for 12 hrs. under vacuum to give 575 mg of a hard brown solid.

*Experimental procedure taken in part from: R. L. Whistler and W. W. Spencer in "Sulfation by Triethylamine Sulfur Trioxide Complex". *Methods in Carbohydrate Chemistry*, Vol. IV, pp. 297–298, 1964; R. L. Whistler, Ed., Academic Press, New York. For alternative procedure see, R. L. Whistler, *Methods Carbohydrate Chem.* VI, pp. 426–429, 1972.

G. CARRISYN ® Extract Crosslinking with Epichlorohydrin 1.00 g of CARRISYN ® extract (light pink-brown colored solid, Lot #8B) was powdered in a mortar and pestle, then suspended in 200 ml of deionized H₂O. With vigorous stirring, epichlorohydrin (0.40 gm, Aldrich Chem. Co., 99%, gold label, Cat. #24,069-9) was added as a neat liquid followed by a solution of NaOH (Mallinckrodt AR grade, 7708, Lot #7708 KVHS 0.5 gm) in 2.5 ml of deionized/degassed H₂O. The mixture was heated at 60° C. for 80 min, then cooled to ambient temperature. The pH was adjusted to 7 with 20% aqueous acetic acid (prepared from Fisher glacial acetic acid, ACS reagent grade, A-38). The reaction mixture was transferred to dialysis tubing (30 cm long, dry cylinder diameter 28.6 mm., Spectrapor Medical Indust. Inc., Los Angeles, CA #132633, 2000 MW cutoff) which had been pre-washed with deionized H₂O. The reaction mixture was dialyzed against deionized H₂O in a 6 L Erlenmeyer flask for 24 hours with H₂O changes every six hours in a cold room at 4° C.

The tubing contents were removed and freeze dried for 12 hours under vacuum to give 485 mg of a light brown solid.

H. Formalin Crosslinked CARRISYN ® Extract 1.00 g of CARRISYN ® extract (light pink-brown solid, Lot #8B) was powdered in a mortar and pestle, then suspended in 200 ml of deionized H₂O. To this suspension was added 3 ml of 37% formalin solution (Baker Analyzed Reagent grade, Lot #33674, Manuf. #2106, 37% formaldehyde) followed by 0.5 g NaOH (Mallinckrodt AR grade, 7708, Lot #7708 KVHS) in 2.5 ml deionized $H_2O$. The mixture was stirred vigorously at 60° C. for 80 minutes. The mixture was cooled to room temperature, the pH was adjusted to 7 with 20% aqueous acetic acid (prepared from Fisher glacial acetic acid, ACS reagent grade, A-38), and the reaction mixture was transferred to dialysis tubing (30 cm. long, dry cylinder diameter 28.6 mm, Spectrapor Medical Indust. Inc., Los Angeles, CA #132633, 2000 MW cutoff). The mixture was dialyzed at 4° C. in a 6 L Erlenmeyer flask against deionized $H_2O$ with $H_2O$ changes every 6 hours.

The tubing contents were removed and freeze dried for 12 hours under vacuum to give 518 mg of a white/brown and brittle solid.

EXAMPLE 39

Comparison of Common Topical Agents for Wound Treatment

Cytotoxicity for Human Fibroblasts in Culture

Cultures of human fibroblasts were used to determine the cytotoxicity of several topical agents that are commonly used for wound cleansing. The objective was to compare a wound gel containing CARRISYN ® extract with several standard cleansing agents that have different modes of action. These standard cleaning agents are designed to reduce bacterial damage and tissue breakdown following breach of the epidermal barrier. Release of radiolabeled chromium and uptake of trypan blue dye were used to measure cytotoxicity. The cultured fibroblasts were not damaged by concentrations of CARRISYN ® extract as high as 0.5%. In contrast, povidoneiodine (Betadine ®), trypsin and balsam of Peru (Granulex TM), chlorhexidine (Hibiclens TM), or hydrogen peroxide released $^{51}Cr$ from labeled cells. Betadine ®, Hibiclens TM and Granulex TM also enhanced staining with trypan blue, but treatment with Carrisyn TM did not. Based upon these in vitro studies, CARRISYN ® extract appears to be safe for topical application and wound treatment.

Cell cultures. Human skin fibroblasts were grown from explants of newborn foreskins and from samples of adult skin collected from the lower abdomen at Caesarean section. The tissue was cleaned of fat and subcutaneous connective tissue, minced into 2 $mm^3$ particles and placed in small (25 $cm^2$) culture flasks. Culture medium, consisting of Minimum Essential Medium TM (MEM) (Inland Laboratories) supplemented with 5% fetal calf serum (Hazelton), 200 mM glutamine and 1% antibiotic, was added, and the cultures were maintained at 37° C. in an atmosphere of 5% $CO_2$.

A mixture of keratinocytes and fibroblasts grew from the edges of the tissue within a few days. The keratinocytes failed to divide, but within 16–21 days the fibroblasts proliferated to form monolayers of elongated cells with a characteristic swirled pattern. All cultures were passaged at least three times before use and were used for up to 10–15 passages.

Topical agents. Several products that are commonly used to treat wounds and decubiti were added directly to standardized cultures of human fibroblasts in order to measure cytotoxicity in an in vitro system. Povidone-iodine solution (Betadine ®), hydrogen peroxide, Granulex TM and chlorhexidine (Hibiclens TM) are commonly used cleansing agents with different mechanisms of action. These compounds (0.001–0.5%) were compared with CARRISYN ® extract for cytotoxic effects on cultured fibroblasts.

Treatment of cells. Cells from confluent monolayers were detached with 0.25% trypsin following a brief exposure (5–10 min) to Pucks-EDTA solution. The suspended cells were centrifuged to a pellet, washed once with fresh medium, and resuspended in MEM supplemental with glutamine, antibiotics and 1% fetal calf serum. Cell number was determined in an electronic cell counter (Coulter TM Electronics, Hialeah, FL) and adjusted by dilution as required for individual experiments. The cells were labeled with $^{51}Cr$ (1 $\mu Ci/ml$) and plated in 24 well multiwell plates at a density of $10^5$ per well. The plates were returned to the incubator for 18 hours. At the start of each experiment, radioactive media were removed by suction, and each well was washed 4 times with fresh MEM plus 1% fetal calf serum. MEM alone or MEM containing various dilutions of the test products was added to replicate wells, and the plates were incubated for 1–30 minutes longer. At the end of the incubation period, the media were collected and reserved for measurement of released radioactivity. The cells in each well were lysed by addition of 0.5 ml of Triton X-100 (1%) with 0.1M NaOH, and samples of the lysates were taken for measurements of radioactivity.

Measurement of cytotoxicity. Cytotoxicity was quantitated by release of radioactive chromium from labeled fibroblasts incubated with the various different chemical agents. The percent release was calculated by dividing the amount of radioactivity in the supernatant media by the total radioactivity in both media and cells.

An alternate assessment of cytotoxicity was provided by staining with trypan blue. The cells were incubated with each of the test agents for 15 minutes. Trypan blue (1%) was added to each well and incubation was continued for 5 minutes longer. The samples were inspected by light microscopy and photographed through a Nikon TM 35 mm camera attached to a Nikon TM inverted phase microscope. Cytotoxicity was estimated by determining the percentage of cells stained with trypan blue in comparison with control (untreated) cells. The results of this determination are shown in Table 23 below.

TABLE 23

Cytotoxicity of Topical Preparations As Determined by Trypan Blue Staining

| Product | Conc. | Inc. Time | Percent Staining |
|---|---|---|---|
| Betadine ® | 0.01% | 15 min. | 100 |
| Hibiclens TM | 0.01% | 15 min. | 100 |
| Granulex TM | 0.01% | 15 min. | 100 |
| CARRISYN ® extract | 0.01% | 15 min. | 5 |
| Media Alone | — | 15 min. | 1 |

Cultured cells were incubated with each of the agents or with media alone for 15 minutes, trypan blue (1%) was applied, and after 5 minutes the number of stained nuclei were counted and expressed as percent of the total cell nuclei within the visual field.

Figure 30:
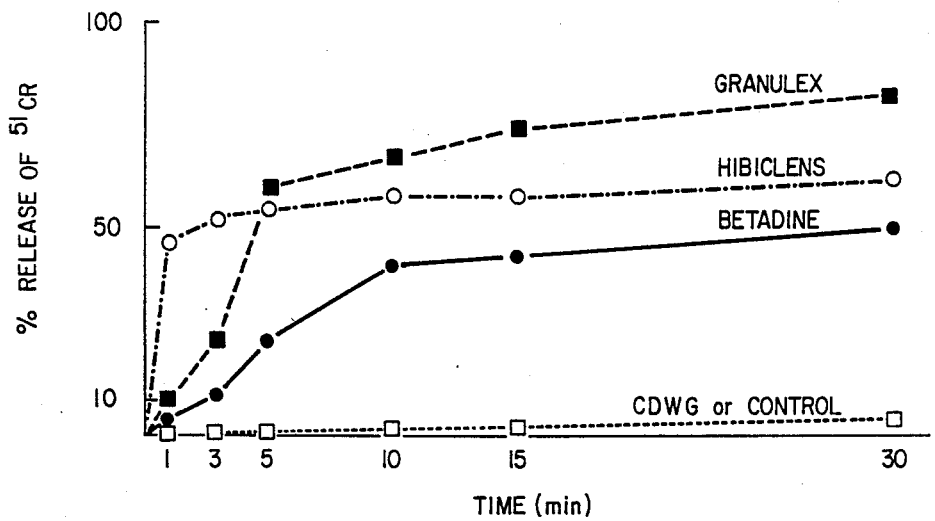
FIG. 30 shows time course of $^{51}$Cr release by topical agents. Cultures of human fibroblasts were incubated for various times with 0.05% Granulex™, Hibiclens™, Betadine® or CARRISYN® extract (CDWG) and the percent of the total radioactivity released was determined. Data are means of 3–5 separate determinations at each time point. Control cells (treated with media alone) released 3–5% of the total $^{51}$Cr during 30 minutes.

Time course of cell injury. Direct cell injury by the topical agents occurred rapidly and was reflected by increased release of $^{51}Cr$ from the cells. Cultured fibroblasts that were treated with medium alone or with 10% fetal calf serum released no more than 5% of the total chromium label during incubation for 5–60 minutes. In contrast, cells treated with 0.05% Betadine, Granulex TM or Hibiclens TM released between 55 and 62% of the total label within 5 minutes. Incubation for 10 or 15 minutes slightly increased the amount released for all of these agents, but longer incubation (30 minutes) did not further increase release of radioactivity. Cells treated with CARRISYN® extract (CDWG) (0.05%) released no more than 5% of the total label during incubation for as long as 30 minutes. (FIG. 30).

Figure 31:
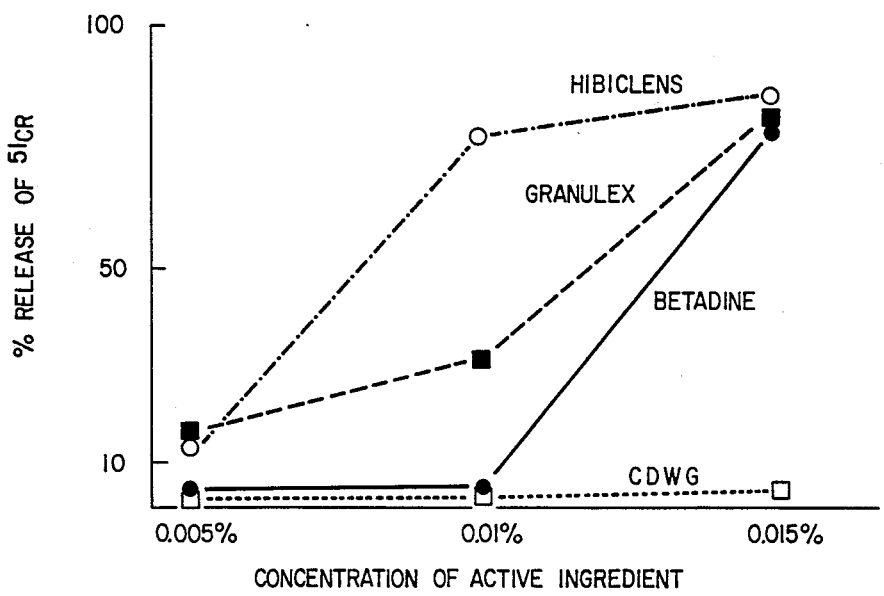
FIGS. 31 shows influence of concentration on cell injury. Cultured fibroblasts were incubated with varying concentrations of Hibiclens™, Granulex™, Betadine® or CARRISYN® extract (CDWG) for 15 minutes at 37° C. The percentage of $^{51}$Cr released was determined for each concentration. Control release (from untreated cells) ranged from 1–5%. Data are means of 3–5 separate determinations.

Influence of concentration on cell injury. The various agents were tested for cytotoxicity in concentrations ranging from 0.005 to 0.05%. As shown in FIG. 31, Granulex ™ and Hibiclens ™ (0.01%) released approximately 25% and 70% of the total chromium label from fibroblasts. Release by the lowest concentrations of Betadine ® (0.005 and 0.01%) was no more than that by medium alone, but cells exposed to 0.015% Betadine ® released more than 70% of their total radioactivity. CARRISYN ® extract in concentrations up to 0.5% released no more than medium alone.

Similar results were obtained when trypan blue staining was used to assess cell injury. As shown in the table, incubation for 15 minutes with 0.01% Betadine ®, Hibiclens ™ or Granulex ™ killed 100% of the cells. Incubation with CARRISYN ® extract at the same concentration killed only 5%. Hydrogen peroxide at a concentration of 0.01% badly damaged the cells as judged by changes in morphology, but trypan blue staining by this agent could not be measured because of its decolorizing effects.

Figure 32:
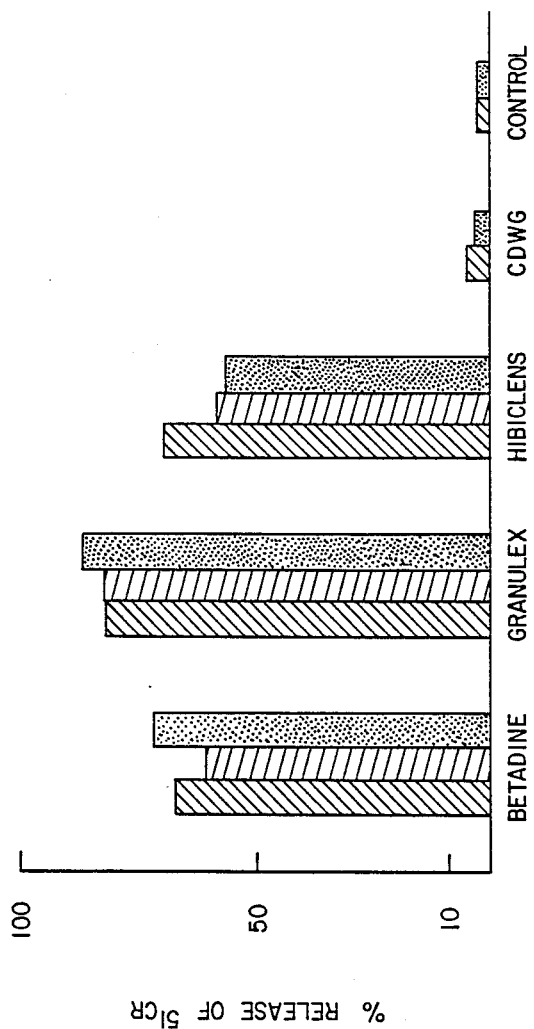
FIG. 32 shows release of chromium: effect of CDWG and serum. Cells were incubated in medium alone (dark bars) or in medium containing CARRISYN® extract (0.5%) (hatched bars) or medium with 10% fetal calf serum (strippled bars) for 15 minutes. Betadine®, Granulex™ or Hibiclens™ (0.15%) were added and the incubation was continued for 15 minutes longer. Data are means of 3–4 separate experiments.

Effects of combined agents. In some experiments CARRISYN ® extract was added to fibroblast cultures before addition of other topical agents to determine if it had a protective effect. The cytotoxic effect was measured in media alone and in media that contained 10% fetal calf serum. FIG. 32 shows that although CARRISYN ® extract alone did not damage the cells, it did not alter the amount of $^{51}$Cr released by either Hibiclens ™ or Betadine ® during a 15 minute incubation period. Similarly, inclusion of fetal calf serum in the incubation medium did not alter the cytotoxic effects of these agents.

EXAMPLE 40

An 83 year old female patient, TB, developed an ulcer, 25 mm in diameter, on the lateral margin of the left foot. The ulcer had been present for several months, and had failed to respond to several treatment regimens.

The wound was treated with the product of Example 3 and the product of Example 7 using a t.i.d. treatment schedule. The clean wound was soaked for 15 minutes with the product of Example 3. Excessive product was absorbed from the wound with a dry sterile 4×4 gauze.

The product of Example 7 was then applied in a quantity sufficient to cover the wound and to prevent wound dehydration between dressing changes.

The progression of wound healing was measured by interval photographs and planimetry of the wound defect. The progression of wound closure is shown in Table 24.

TABLE 24

| PROGRESSION OF WOUND HEALING | | |
| --- | --- | --- |
| Day | Wound Area (Sq. In.) | Percentage of Healing |
| 1 | 1.24 | 0.00 |
| 28 | 0.51 | 58.87 |
| 77 | 0.29 | 76.61 |
| 83 | 0.12 | 90.32 |
| 97 | 0.00 | 100.00 |

The epidermal defect was substantially closed in 12 weeks with complete closure occuring in 14 weeks.

EXAMPLE 41

A 32 year old patient was presented with a history of ulcerative colitis for "many years". During an active episode, she had been unresponsive to a daily regimen of 40 mg Prednisone, 3 grams Asulfidine, 50 mg 6-mercaptopurine, and Flagyl¼. She continued to have a painful abdomen and 4-8 bloody bowel movements per day. She was placed on hyperalimentation. Endoscopic findings revealed severe ascending colon ulcerations with mild hepatic to transverse ulcerations. The patient was placed on 50 mg of CARRISYN ® extract q.i.d. in addition to her other medications and sent home. In one week, her symptoms were virtually gone. The abdomen was mildly tender and endoscopy revealed a healed and mildly congested mucosa. The patient was slowly taken off other medications and the clinical picture continued to improve. The patient is currently maintained on CARRISYN ® extract as the sole medication at this time. Physical exam and symptoms are recorded as totally normal.

Five additional cases with similar responses to ulcerative colitis and Crohn's disease, have been seen. One patient ran out of CARRISYN ® extract capsules. In four weeks, mild symptoms began to recur (there was increased stool with mild abdominal discomfort), and she returned for a supply of medication. In three days, she was back to total normal bowel symptomatology.

EXAMPLE 42

A number of AIDS patients have received prolonged high doses of CARRISYN ® extract without toxicity or side-effects. A rise in T-4 and T-8 lymphocyte ratios and an increase in absolute T-4 counts was seen in these AIDS patience with a reduction and elimination of clinical symptoms, as well as a reduction in opportunistic infections. It is suggested that CARRISYN ® extract had an anti-viral or immune modulation effect in patients.

A stimulation to the lymphocytes of these patients has been observed which suggests that CARRISYN ® extract may be involved in immune modulation.

EXAMPLE 43

Tic douloureux, or neuralgia of the fifth cranial nerve, is characterized by attacks of severe, unbearable pain over one or more branches of the trigeminal nerve. The pain usually is transient, and attacks may be precipitated by touching some area of the face—the so-called trigger zone.

The cause and cure of this painful disease are unknown. Several attempts to treat the disorder have met with little or no success. Various treatments have included analgesics, phenytoin, peripheral avulsion of the involved nerve branch as it leaves the skull, and injection of 98 percent alcohol into the gasserian ganglion.

A more drastic treatment—sectioning the sensory root of the nerve proximal to the ganglion—leaves the patient permanently without sensation in the area supplied by the sectioned nerve. Another recent treatment attempt uses carbamazepine and phenoliophendylate injections. However, these injections can be complicated by painful numbness and serious side effects.

None of the previously cited treatments is desirable.

A 43 year old woman was diagnosed as having tic douloureux. The affected area included the first and third divisions of the trigeminal nerve on the right side.

The patient could trigger the pain by brushing or combing her hair on the right side. She had been treated unsuccessfully with diazepam (Valium TM), antihistamines, analgesics, propranolol hydrochloride (Inderal TM), and phenobarbital. The patient said she had not had a pain-free day since the onset of the disease.

The proposed therapy involved drinking 1 to 2 oz. of the product of Example 2 daily for three months. After that period, the therapy would be evaluated.

The patient's pain diminished significantly within two weeks of initiating therapy. She said she felt well for a few weeks. However, she then went on a two week trip, during which she did not drink the product of Example 2. The symptoms and pain returned during the trip. After she resumed the medication, however, the pain disappeared within a few days. For the next few weeks, she again felt well.

After drinking the juice daily for more than six months without interruption, she reports that she can brush and comb her hair without triggering the pain. Her appearance has improved, and she says she feels better than ever before.

EXAMPLE 44

The Effect of Alcohol Concentration on CARRISYN ®Extract Yield

Procedure

Hilltop leaves (15.9 lbs.) were washed, filleted and ground in a Waring TM blender, then filtered through eight layers of cotton cloth. The gel was then transferred to four 11 quart, stainless steel pans, and cold USP grade ethyl alcohol was added to each in two, three, four and five to one ratios by volume. The amounts can be summarized as follows:

| Ratio (ethanol:aloe gel) | Amt. of Gel | Amt. of Ethyl Alcohol |
|---|---|---|
| 2:1 | 500 ml | 1000 ml |
| 3:1 | 500 ml | 1500 ml |
| 4:1 | 1670 ml | 6680 ml |
| 5:1 | 500 ml | 2500 ml |

The precipitates were allowed to settle out for four hours, then the remaining alcohol-gel solutions were carefully decanted and saved in separate containers. The precipitates were centrifuged for 10 minutes at 2,800 rpm using a IEC Centra-7 TM centrifuge, washed with alcohol, then centrifuged again under the same conditions. The pellets were transferred to 600 ml jars, frozen in liquid nitrogen, and lyophilized overnight.

An additional volume of alcohol was added to the supernatant from the 2:1 ratio and allowed to settle overnight at room temperature. The remaining supernatants were also left at room temperature and allowed to settle out overnight.

The following day, the precipitates were collected from the supernates as previously described, with the exception of the pellet from the 2:1 ratio that had been precipitated with an additional volume of alcohol. In this case, approximately 5–10 ml of water was added as the pellet was transferred to the lyophilization jar.

RESULTS

The results of the initial, four hour alcohol precipitations can be summarized as follows:

| Ratio (ethanol:aloe gel) | Yield(g) | % Yield(g. CARRISYN ® extract/g. gel) |
|---|---|---|
| 2:1 | .0518 | .010 |
| 3:1 | .3847 | .077 |
| 4:1 | 1.945 | .116 |
| 5:1 | .6675 | .134 |

After addition of another volume of ethyl alcohol, the 2:1 supernate produced another 178 mg of CARRISYN ® extract. Just by settling overnight, the 3:1 and 4:1 ratio supernates yielded another 89 and 105 mg, respectively. The 5:1 ratio yielded only negligible precipitation after the initial isolation, and was thus not reharvested.

In the case of the second precipitation from the 2:1 ratio (3:1), 5–10 ml of water were used to rinse out the centrifuge bucket before lyophilization. This produced a white, fluffy CARRISYN ® extract of low density that differed greatly from the denser, gray colored CARRISYN ® extract samples that the other samples produced.

SUMMARY

CARRISYN ® extract is predominantly a mannan as evidenced by Example 13 which shows that CARRISYN ® extract consists of about 80% mannose. The mannose monomers of the mannan are connected largely by a $\beta(1\rightarrow 4)$ linkage as evidenced by Example 14. The results from elemental analyses, IR, NMR and acetyl group analysis show that there are O-acetyl, N-acetyl and carboxylate functional groups on CARRISYN ® extract.

The time it takes to process CARRISYN ® extract prior to precipitation has been shown to be important on the overall quality and yield of the CARRISYN ® extract. The longer the gel is allowed to stand before CARRISYN ® extract is precipitated, the longer the enzyme in the gel have to work on CARRISYN ® extract and cleave the functional groups and glycosidic bonds ($\beta(1\rightarrow 4)$) thus, reducing or eliminating its activity.

The following structure was deduced from all of the above experimental results and evidence:

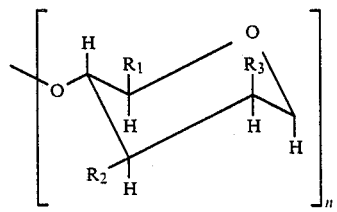

wherein
$R_1$=—CH$_2$OH, —COO$^-$, or —CH$_2$OOCCH$_3$;
$R_2$=—OH, —OOCCH$_3$, or —NHCCH$_3$;
$R_3$=—OH, —OOCCH$_3$, or —NHCOCH$_3$; and
n=2 to about 50,000.

The predominantly mannan chain may include other substituted simple pentose or hexose monomers.

The production, isolation and characterization of CARRISYN ® extract involved novel and unobvious procedures and techniques. As evidenced by the prior work of others in this field, which prior work was incorrect or inaccurate for one reason or another, CARRISYN ® extract is novel and unobvious from the prior attempts of others to isolate and characterize the active substance in Aloe.

What is claimed is:

1. A process for producing a substantially anthraquinone-free aloe gel from a leaf of the aloe plant, comprising:
   (a) washing an aloe leaf in a bacteriacidal solution to remove substantially all surface dirt and bacteria;
   (b) removing at least a first end portion from said washed leaf;
   (c) draining, preserving and collecting anthraquinone rich sap from said cut and washed leaf; and
   (d) removing rind from said leaf to produce a substantially anthraquinone free gel.

2. A process for producing substantially anthraquinone-free aloe gel from a leaf of the aloe plant, comprising:
   (a) crushing a leaf of an aloe plant; and
   (b) dialyzing the crushed leaf chemically to remove and separate a substantially anthraquinone-free aloe gel from remaining fractions of the crushed leaf.

3. A process for producing substantially anthraquinone-free aloe gel from a leaf of the aloe plant according to claim 2, wherein prior to crushing said leaf, said leaf is washed in a bacteriacidal solution to remove substantiall all surface dirt and bacteria.

4. A process for producing substantially anthraquinone-free juice from a leaf of the aloe plant comprising:
   (a) washing an aloe leaf in a bacteriacidal solution substantially to remove surface dirt and bacteria;
   (b) removing a first end portion and a second end portion from said washed leaf;
   (c) draining, preserving and collecting anthraquinone rich sap from said washed and cut leaf;
   (d) removing rind from said leaf to produce a substantially anthraquinone-free aloe gel fillet; and
   (e) grinding and homogenizing said substantially anthraquinone-free aloe gel fillet to produce substantially anthraquinone-free aloe juice.

5. A process for producing substantially anthraquinone-free aloe juice according to claim 4, further comprising, filtering said aloe juice to remove fibrous material.

6. A process for producing substantially anthraquinone-free aloe juice according to claim 4 further comprising, adding at least one member selected from the group consisting of preservative, flavorant, excipient, carrier and colorant to said aloe gel fillet or said aloe juice.

7. A process for producing substantially anthraquinone-free aloe juice according to claim 5, wherein said preservative is selected from the group consisting of methyl paraben, propyl paraben, and butyl paraben.

8. A process for producing substantially anthraquinone-free aloe juice according to claim 5, wherein said juice is irradiated, freeze-dried, sonic sterilized or pasteurized whereby said juice is preserved.

9. A process for producing substantially anthraquinone-free aloe juice according to claim 5, further comprising the step of:
filtering said aloe juice by ultrafiltration osmotically to adjust and size by molecular weight said aloe juice.

10. A process for producing substantially anthraquinone-free aloe juice according to claim 4, further comprising the step of:
washing said substantially anthraquinone-free aloe gel fillet in a tumbler washer prior to grinding said fillet.

11. A product produced by the process of claim 4.
12. A product produced by the process of claim 5.
13. A product produced by the process of claim 6.
14. A product produced by the process of claim 7.
15. A product produced by the process of claim 8.
16. A product produced by the process of claim 9.

17. A process for extracting the active chemical substance in the aloe plant from a leaf of the aloe plant, comprising steps of:
   (a) obtaining aloe juice having solubilized matter;
   (b) adding a water soluble, lower aliphatic polar solvent to the aloe juice to precipitate the active chemical substance and thereby to form a heterogeneous solution;
   (c) removing the water soluble, lower aliphatic polar solvent and the solubilized matter from the heterogeneous solution to isolate the precipitated active chemical substance; and
   (d) drying the precipitated active chemical substance.

18. A process for extracting the active chemical substance in the aloe plant from a leaf of the aloe plant according to claim 17, wherein said aloe juice is obtained by:
   (a) washing an aloe leaf in a bacteriacidal solution to remove substantally all surface dirt and bacteria;
   (b) removing at least a first end portion from said washed leaf;
   (c) draining, preserving and collecting anthraquinone rich sap from said cut and washed leaf;
   (d) removing rind from said leaf to produce a substantially anthraquinone-free gel fillet; and
   (e) grinding and homogenizing said substantially anthraquinone-free aloe gel fillet to produce substantially anthraquinone-free aloe juice having solubilized matter.

19. A process for extracting the active chemical substance in the aloe plant according to claim 18, wherein said precipitate is irradiated, whereby said active chemical substance is sterilized and preserved.

20. A process for extracting the active chemical substance in the aloe plant according to claim 18, wherein four volumes of said water soluble, lower aliphatic polar solvent are added to one volume of aloe juice to precipitate said active chemical substance.

21. A process for extracting the active chemical substance in the aloe plant according to claim 18, wherein said water soluble, lower aliphatic polar solvent is selected from the group consisting of methanol, ethanol and propanol.

22. A process for extracting the active chemical substance in the aloe plant according to claim 21, wherein said water soluble, lower aliphatic polar solvent is ethanol.

23. A process for extracting the active chemical substance in the aloe plant according to claim 18, wherein said active chemical substance is precipitated from said water soluble, lower aliphatic polar solvent and aloe juice for approximately four hours before said water soluble, lower aliphatic polar solvent is removed.

24. A process for extracting the active chemical substance in the aloe plant according to claim 18, wherein said precipitated active chemical substance is dried by lyophilization.

25. A process for extracting the active chemical substance in the aloe plant from a leaf of the aloe plant according to claim 17, wherein said aloe juice is obtained by:
 (a) washing an aloe leaf in a bacteriacidal solution to remove substantially all surface dirt and bacteria;
 (b) crushing the washed aloe leaf;
 (c) dialyzing the crushed leaf chemically to remove and separate a substantially anthraquinone-free gel from remaining fractions of the crushed leaf; and
 (d) grinding and homogenizing said substantially anthraquinone-free aloe gel to produce substantially anthraquinone-free aloe juice having solubilized matter.

26. A process for extracting the active chemical substance in the aloe plant from a leaf of the aloe plant according to claim 17, wherein said aloe juice is obtained by:
 (a) washing an aloe leaf in a bacteriacidal solution to remove substantially all surface dirt and bacteria;
 (b) crushing the washed aloe leaf; and
 (c) grinding and homogenizing said crushed aloe leaf to produce aloe juice having solubilized matter.

27. A process for extracting the active chemical substance in the aloe plant from a leaf of the aloe plant according to claim 17, wherein said aloe juice is obtained by:
 (a) washing an aloe leaf in a bacteriacidal solution to remove surface dirt and bacteria;
 (b) grinding said washed aloe leaf;
 (c) filtering said ground aloe leaf to remove fibrous material; and
 (d) homogenizing said ground aloe leaf to produce an anthraquinone-rich aloe juice having solubilized matter.

28. A process for extracting the active chemical substance in the aloe plant from a leaf of the aloe plant according to claim 17, wherein said aloe juice is obtained by:
 (a) crushing a leaf of an aloe plant to extrude aloe juice having solubilized matter.

29. A process for extracting the active chemical substance in the aloe plant from a leaf of the aloe plant according to claim 17, wherein said aloe juice is obtained by:
 (a) washing an aloe leaf in a bacteriacidal solution to remove substantially all surface dirt and bacteria;
 (b) removing rind from said leaf to produce an aloe gel fillet; and
 (c) grinding and homogenizing said aloe gel fillet to produce aloe juice having solubilized matter.

30. A product produced by the process of claim 17.
31. A product produced by the process of claim 18.
32. A product produced by the process of claim 25.
33. A product produced by the process of claim 26.
34. A product produced by the process of claim 27.
35. A product produced by the process of claim 28.
36. A product produced by the process of claim 29.
37. A product produced by the process of claim 19.
38. A product produced by the process of claim 20.
39. A product produced by the process of claim 21.
40. A product produced by the process of claim 22.
41. A product produced by the process of claim 23.
42. A product produced by the process of claim 24.

43. A process for extracting the active chemical substance in the aloe plant from a leaf of the aloe plant according to claim 17, wherein said aloe juice is obtained by:
 (a) removing rind from said leaf to produce an aloe gel fillet;
 (b) grinding and homogenizing said aloe gel fillet to produce aloe juice having solubilized matter; and
 (c) filtering said aloe juice to remove fibrous material.

44. A process for extracting the active chemical substance in the aloe plant from a leaf of the aloe plant according to claim 43, wherein immediately prior to said filtering step, said ground and homogenized aloe juice is dialyzed chemically to remove and separate a substantially anthraquinone-free aloe juice.

45. A composition of matter for a topical wound gel, comprising:
 (a) 0.1 to 100 wt. % substantially anthraquinone-free aloe juice,
 (b) 0 to 2 wt. % allantoin,
 (c) 0 to 6 wt. % panthenol,
 (d) one or more excipients or carriers.

46. A composition of matter for drinking, comprising:
 (a) 0.1 to 100 wt % substantially anthraquinone-free aloe juice,
 (b) a food preservative
 (c) citric acid; and
 (d) vitamin E.

47. A base formulation for the production of Aloe vera containing topical products, comprising:
 (a) one or more preservatives; and
 (b) a substantially anthraquinone-free aloe juice.

48. The formulation of claim 47, wherein the preservatives are potassium sorbate and methylparaben.

49. A base formulation for the production of Aloe vera containing topical products, comprising:
 (a) methylparaben;
 (b) potassium sorbate; and
 (c) a substantially anthraquinone-free aloe juice,
wherein the weight ratio of methylparaben to potassium sorbate is about 1.79:1.

50. A moisture-resistant ointment emulsion formulation for topical administration, having an aqueous component phase and an oil component phase, comprising:
 (A) for the aqueous phase:
  (1) a substantially anthraquinone-free aloe juice;
  (2) an agent to reduce skin surface tension and to permit adsorption on the skin of said aloe juice;
  (3) an active agent to promote healing of the skin;
  (4) one or more preservatives for the water phase; and a
  (5) pH adjuster for the aqueous phase; and
 (B) for the oil phase:
  (1) one or more oil barrier agents to prevent the removal of the aqueous phase from the skin by contact of the skin by an aqueous-containing solution;
  (2) one or more thickness for the oil phase;
  (3) a mixing agent for the oil phase;
  (4) a skin softener;
  (5) an oil base for the oil phase; and
  (6) a preservative.

51. The moisture-resistant ointment of claim 50, wherein the oil phase additionally comprises:
 (a) a agent to promote skin cell metabolism;
 (b) a protein for wound healing; and
 (c) a fragrance.

52. The moisture-resistant ointment of claim 50, wherein:
(A) in the aqueous phase:
  (1) the agent to reduce skin surface tension and to permit adsorption on the skin of the aloe juice is propylene gylcol;
  (2) the active agent to promote healing of the skin is allantoin;
  (3) the preservatives for the aqueous phase are imidazolidinyl urea, methylparaben, and sorbitol; and
  (4) the pH adjuster for the aqueous phase is phosphoric acid; and
(B) in the oil phase:
  (1) the barrier agents are glyceryl stearate and stearyl stearate, and dimethicone;
  (2) the thickeners for the oil phase are dioctyl adipate, octyl stearate and octyl palmitate;
  (3) the mixing agent is cetyl alcohol;
  (4) the skin softener is lanolin;
  (5) the oil base for the oil phase is mineral oil; and
  (6) the preservative is propylparaben;

53. The moisture-resistant ointment of claim 51, wherein in the oil phase:
(a) the agent to promote skin cell metabolism is Vitamin E;
(b) the protein for wound healing is cocamidopropyldimonium hydroxypropylamino collagen.

54. A moisture-resistant emulsion formulation for topical administration having an aqueous component phase and an oil component phase, comprising:
(A) for the aqueous phase:
  (1) a substantially anthraquinone-free aloe juice;
  (2) propylene glycol;
  (3) allantoin;
  (4) methylparaben;
  (5) imidazolidinyl urea;
  (6) sorbitol; and
  (7) phosphoric acid; and
(B) for the oil phase:
  (1) glyceryl sterate;
  (2) stearyl stearate;
  (3) dioctyl adipate and octyl sterate and octyl palmitate;
  (4) palmitamidopropyl dimethylamine;
  (5) cetyl alcohol;
  (6) lanolin;
  (7) mineral oil;
  (8) dimethicone; and
  (9) propylparaben,
wherein:
  (1) in the aqueous phase, the weight ratio of propylene glycol to allantoin to methylparaben to imidazolidinyl urea to sorbitol to phosphoric acid is 17:1:0.75:0.002:1:1; and
  (2) in the oil phase, the weight ratio of glyceryl stearate to stearyl stearate to dioctyl adipate and octyl stearate and octyl palmitate to palmitamidopropyl dimethylamine to cetyl alcohol to lanolin to mineral oil to dimethicone to propylparaben is about 36:9:9.3.5:3.5:3.5:3.5:1:0.3.

55. The moisture-resistant emulsion formulation of claim 54 wherein the oil phase additionally comprises Vitamin E and cocamidopropyldimonium hydroxypropylamino collagen, and wherein the ratio of Vitamin E to cocamidopropyldimonium hydroxypropylamino collagen is 1:1.

56. An aloe-based counter-irritant formulation having a water phase and an oil phase for treatment of soft-tissue skin injury, comprising:
(A) A carrier slurry for the water phase, comprising a water-miscible thickener;
(B) A water phase, comprising:
  (1) a substantially anthraquinone-free aloe juice;
  (2) an agent to reduce surface tension and to permit adsorption on the skin of the aloe juice;
  (3) a surfactant-emulsifier and pH adjuster;
  (4) an active agent to promote healing of the skin;
  (5) a thickener for the water phase; and
  (6) one or more preservatives;
(C) An oil phase, comprising:
  (1) an extended wear vehicle for an oil base;
  (2) an oil base;
  (3) one or more thickeners for the oil phase;
  (4) a mixing agent;
  (5) one or more active counter-irritant agents;
  (6) one or more preservatives; and
  (7) an anti-inflammatory agent.

57. The counter-irritant formulation of claim 56, wherein
(A) The water miscible thickener is a water-soluble resin used to form gels consisting of cross-linked, high molecular weight acrylic acid polymers;
(B) In the water phase,
  (1) the agent to reduce surface tension and to permit adsorption on the skin of the aloe juice is propylene glycol;
  (2) the surfactant-emulsifier and pH adjuster is triethanolamine;
  (3) the active agent to promote healing of the skin is allantoin;
  (4) the thickener for the water phase is an acrylic acid polymer; and
  (5) the preservatives comprise potassium sorbate, methylparaben, and urea; and
(C) In the oil phase,
  (1) the extended wear vehicle for the oil base is petroleum USP (white);
  (2) the oil base comprises Carnation (white) mineral oil, mineral oil, lanolin alcohol, and acetylated lanolin alcohol;
  (3) the thickeners for the oil phase comprise stearic acid, glyceryl stearate, dioctyl adipate, octyl stearate, octyl palmitate, white oleic acid, and stearyl stearate;
  (4) the mixing agent is cetyl alcohol;
  (5) the counter-irritant agents are eucalyptus oil, methyl salicylate, camphor, and methol;
  (6) the preservatives are propylparaben and butylparaben;
  (7) the anti-inflammatory agent is histamine dihydrochloride.

58. An aloe-based counter-irritant formulation having a water phase and an oil phase for treatment of soft-tissue skin injury, comprising:
(A) A carrier slurry for the water phase, comprising one or more cross-linked, high molecular acrylic acid polymers;
(B) A water phase, comprising:
  (1) a substantially anthraquinone-free aloe juice;
  (2) propylene glycol;
  (3) triethanolamine;
  (4) allantoin;
  (5) methylparaben;
  (6) potassium sorbate and urea;

(C) An oil phase, comprising:
  (1) petroleum USP (white);
  (2) Carnation (white) mineral oil;
  (3) mineral oil;
  (4) lanolin alcohol;
  (5) acetylated lanolin alcohol;
  (6) stearic acid;
  (7) glyceryl stearate;
  (8) dioctyl adipate;
  (9) octyl stearate;
  (10) octyl palmitate;
  (11) white oleic acid;
  (12) stearyl stearate;
  (13) propylparaben;
  (14) butylparaben;
  (15) cetyl alcohol;
  (16) eucalyptus oil;
  (17) methylsalicylate;
  (18) camphor;
  (19) menthol; and
  (20) histamine dihydrochloride
wherein the ratio of acrylic acid polymer to propylene glycol to triethanolamine to allantoin to methylparaben to potassium sorbate to urea to petroleum USP (white) to Carnation (white) mineral oil to mineral oil and lanolin alcohol to acetylated lanolin alcohol to stearic acid to glyceryl stearate to dioctyl adipate and octyl stearate and octyl palmitate to white oleic acid to stearyl stearate to propylparaben to butylparaben to cetyl alcohol to eucalyptus oil to methylsalicylate to camphor to menthol to histamine dihydrochloride is about 4:49.5:8.9:0.59:1:0.5:19.8:7.5:6.9:6.9:21.4:9.4:9.4:1:1:1:1:-7.5:19.8:0.123:19.8:19.8:0.5.

59. A composition of matter for a topical wound gel, comprising:
  (a) 0.1% up to about 100 wt. % substantially anthraquinone-free aloe juice;
  (b) less than 2 wt. % allantoin;
  (c) less than 6 wt. % panthenol;
  (d) a water-miscible thickener;
  (e) a nutrient;
  (f) one or more surfactant-emulsifiers and pH adjusters; and
  (g) one or more preservatives.

60. A composition of matter for a topical wound gel, comprising:
  (a) a water-soluble, hydrophilic aliphatic polymer resin consisting of cross-linked, high-molecular weight acrylic acid polymers;
  (b) a substantially anthraquinone-free aloe juice;
  (c) panthenol;
  (d) allantoin;
  (e) L-glutamic acid;
  (f) imidazolidinyl urea, potassium sorbate and sodium benzoate; and
  (g) triethanolamine.

61. A composition of matter for a topical wound gel, comprising:
  (a) a water-soluble, hydrophilic aliphatic polymer resin consisting of cross-linked, high-molecular weight acrylic acid polymers;
  (b) a substantially anthraquinone-free aloe juice;
  (c) panthenol;
  (d) allantoin;
  (e) L-glutamic acid;
  (f) imidazolidinyl urea, potassium sorbate and sodium benzoate; and
  (g) triethanolamine,
wherein the weight ratio of the hydrophilic aliphatic polymer to the substantially anthraquinone-free aloe juice to the panthenol to the allantoin to the L-glutamic acid to the imidazolidinyl urea to the potassium sorbate to the sodium benzoate to the triethanolamine is approximately 0.7:95.45: 2.0:0.6:0.3:0.1:0.05:0.1:0.7.

62. A composition of matter for drinking, comprising:
  (a) less than 100 wt. % substantially anthraquinone-free aloe juice;
  (b) sodium benzoate and potassium sorbate;
  (c) citric acid;
  (d) Vitamin E;
  (e) glycine;
  (f) vanilla; and
  (g) cinnamon oil.

63. A composition of matter for drinking, comprising:
  (a) less than 100 wt. % substantially anthraquinone-free aloe juice;
  (b) sodium benzoate and potassium sorbate;
  (c) citric acid;
  (d) Vitamin E;
  (e) glycine;
  (f) vanilla; and
  (g) cinnamon oil,
wherein the weight ratio of substantially anthraquinone-free aloe juice to sodium benzoate to potassium sorbate to citric acid to Vitamin E to glycine to vanilla to the cinnamon oil is approximately 989.011:0.986:0.493:1.085:0.261:7.829:0.316:0.019.

* * * * *